(12) United States Patent
Seo et al.

(10) Patent No.: US 11,456,427 B2
(45) Date of Patent: Sep. 27, 2022

(54) ORGANIC LIGHT EMITTING DIODE AND ORGANIC LIGHT EMITTING DEVICE HAVING THE SAME

(71) Applicant: LG Display Co., Ltd, Seoul (KR)

(72) Inventors: Bo-Min Seo, Paju-si (KR); Jeong-Eun Baek, Paju-si (KR); Dae-Wi Yoon, Paju-si (KR); Mi-Sang Yoo, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 414 days.

(21) Appl. No.: 16/711,035

(22) Filed: Dec. 11, 2019

(65) Prior Publication Data
US 2020/0194689 A1 Jun. 18, 2020

(30) Foreign Application Priority Data
Dec. 13, 2018 (KR) .................... 10-2018-0161122

(51) Int. Cl.
*H01L 51/00* (2006.01)

(52) U.S. Cl.
CPC ...... *H01L 51/0074* (2013.01); *H01L 51/0067* (2013.01); *H01L 51/0072* (2013.01); *H01L 51/0073* (2013.01)

(58) Field of Classification Search
None
See application file for complete search history.

(56) References Cited

U.S. PATENT DOCUMENTS

| 8,460,950 B2 * | 6/2013 | Ono | H01L 51/5012 438/22 |
| 10,290,824 B2 * | 5/2019 | Nakanotani | H01L 51/50 |
| 11,183,670 B2 * | 11/2021 | Li | C07F 15/006 |
| 2006/0066225 A1 * | 3/2006 | Kishino | C09K 11/06 313/506 |

(Continued)

FOREIGN PATENT DOCUMENTS

| CN | 102858911 A | 1/2013 |
| CN | 104725297 A | 6/2015 |

(Continued)

OTHER PUBLICATIONS

Karunathilaka et al. "Suppression of external quantum efficiency rolloff in organic light emitting diodes by scavenging triplet excitons." Nature communications 11.1 (2020): 1-9. (Year: 2020).*

(Continued)

*Primary Examiner* — Robert S Loewe
(74) *Attorney, Agent, or Firm* — Birch, Stewart, Kolasch & Birch, LLP

(57) ABSTRACT

An organic light emitting diode including at least one emitting material layer, which includes a host and a dopant and at least one exciton energy control layer disposed adjacently to the at least one emitting material layer and an organic light emitting device having the same is disclosed. The at least one exciton energy control layer includes an organic compound that has excited state singlet and triplet energy levels lower than excited state singlet and triplet energy levels of the host. The organic light emitting diode can enhance its luminous efficiency and its luminous lifetime by incorporating one or more exciton energy control layers.

40 Claims, 19 Drawing Sheets

(56) References Cited

U.S. PATENT DOCUMENTS

| | | | |
|---|---|---|---|
| 2006/0175958 A1* | 8/2006 | Gerhard | C09B 57/00 |
| | | | 313/504 |
| 2006/0232194 A1* | 10/2006 | Tung | H01L 51/5004 |
| | | | 313/506 |
| 2006/0273714 A1* | 12/2006 | Forrest | H01L 51/5044 |
| | | | 313/506 |
| 2006/0279203 A1* | 12/2006 | Forrest | H01L 51/50 |
| | | | 313/503 |
| 2008/0284318 A1* | 11/2008 | Deaton | H01L 51/5044 |
| | | | 313/504 |
| 2008/0286610 A1* | 11/2008 | Deaton | H01L 51/5016 |
| | | | 428/411.1 |
| 2012/0241725 A1* | 9/2012 | Sawabe | H01L 51/5004 |
| | | | 257/40 |
| 2014/0175388 A1* | 6/2014 | Lin | H01L 51/504 |
| | | | 438/46 |
| 2018/0323014 A1* | 11/2018 | Wang | H01L 51/0059 |
| 2019/0036033 A1* | 1/2019 | Nakanotani | H01L 51/0067 |
| 2019/0067589 A1* | 2/2019 | Yoon | H01L 51/0054 |
| 2019/0135797 A1 | 5/2019 | Gao et al. | |
| 2019/0214579 A1* | 7/2019 | Seda | H01L 51/0058 |
| 2021/0083196 A1* | 3/2021 | Galan | C07D 251/24 |

FOREIGN PATENT DOCUMENTS

| | | |
|---|---|---|
| CN | 108864068 A | 11/2018 |
| KR | 10-2007-0102021 A | 10/2007 |
| KR | 10-2017-0033892 A | 3/2017 |
| KR | 10-2018-0035528 A | 4/2018 |
| TW | 201434802 A | 9/2014 |
| TW | 201537801 A | 10/2015 |
| WO | WO 2014/166586 A1 | 10/2014 |
| WO | WO 2014/194971 A1 | 12/2014 |

OTHER PUBLICATIONS

Deaton, Joseph C., et al. "The blue aluminum and gallium chelates for OLEDs." Inorganica Chimica Acta 361.4 (2008): 1020-1035. (Year: 2008).*

* cited by examiner

ORGANIC LIGHT EMITTING DIODE AND ORGANIC LIGHT EMITTING DEVICE HAVING THE SAME

CROSS-REFERENCE TO RELATED APPLICATIONS

This application claims the priority benefit under 35 U.S.C. § 119(a) of Korean Patent Application No. 10-2018-0161122, filed in the Republic of Korea on Dec. 13, 2018, which is incorporated herein by reference in its entirety into the present application.

BACKGROUND

Technical Field

The present disclosure relates to an organic light emitting diode, and more specifically, to an organic light emitting diode having enhanced luminous efficiency and life span and an organic light emitting device having the same.

Description of the Related Art

Among the flat display devices used widely at present, organic light emitting diodes (OLEDs) are rapidly replacing liquid crystal display devices (LCDs). In the OLED, when electrical charges are injected into an emission layer between an electron injection electrode (i.e., cathode) and a hole injection electrode (i.e., anode), electrical charges are combined to be paired, and then emit light as the combined electrical charges are disappeared.

The OLED can be formed as a thin film having a thickness less than 2000 Å and can be implement unidirectional or bidirectional images as electrode configurations. In addition, OLEDs can be formed on a flexible transparent substrate such as a plastic substrate so that OLED can implement a flexible or foldable display with ease. Moreover, the OLED can be driven at a lower voltage of 10 V or less. Besides, the OLED has relatively lower power consumption for driving compared to plasma display panels and inorganic electroluminescent devices, and the color purity of the OLED is very high.

Since only singlet excitons in the common fluorescent material according to the related art can be involved in luminous process, luminous efficiency of the common fluorescent material is low. On the contrary, the phosphorescent material of the related art in which triplet excitons as well as singlet excitons participate in the luminous process show high luminous efficiency compared to the common fluorescent material. However, since a metal complex as a representative phosphorescent material has a short luminous lifetime, its commercial applications have been limited.

BRIEF SUMMARY

Accordingly, the present disclosure is directed to an organic light emitting diode and an organic light emitting device including the organic light emitting diode that can reduce one or more of the problems due to the limitations and disadvantages of the related art.

An object of the present disclosure is to provide an organic light emitting diode that can enhance its luminous efficiency and its luminous lifetime and an organic light emitting device including the organic light emitting diode.

Additional features and advantages of the disclosure will be set forth in the description which follows, and in part will be apparent from the description, or can be learned by practice of the disclosure. The objectives and other advantages of the disclosure will be realized and attained by the structure particularly pointed out in the written description and claims hereof as well as the appended drawings.

According to an aspect, the present disclosure provides an organic light emitting diode that comprises a first electrode and a second electrode facing each other; and an at least one emitting unit disposed between the first and second electrodes and including an emitting material layer, wherein the emitting material layer includes a first emitting material layer including a first host and a first dopant, and a first exciton energy control layer disposed between the first electrode and the first emitting material layer or between the first emitting material layer and the second electrode, wherein the first exciton energy control layer includes a first organic compound, and wherein each of an excited state singlet energy level and an excited state triplet energy level of the first organic compound is lower than each of an excited state singlet energy level and an excited state triplet energy level of the first host, respectively.

In other words, it may be said that each of an excited state singlet energy level and an excited state triplet energy level of the first organic compound is lower than each of an excited state singlet energy level and an excited state triplet energy level of the first host, respectively when the excited state singlet energy level of the first organic compound is lower than the excited state singlet level of the first host and the excited state triplet energy level of the first organic compound is lower than the excited state triplet energy level of the first host. In other words, it may be said that it may further be the case that both the excited state singlet energy level and the excited state triplet energy level of the first organic compound are lower than both the excited state singlet energy level and the excited state triplet energy level of the first host.

According to another aspect, the present disclosure provides an organic light emitting device that comprises a substrate and an OLED disposed over the substrate, as described above.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Reference will now be made in detail to aspects of the disclosure, examples of which are illustrated in the accompanying drawings.

[Organic Light Emitting Device]

Figure 1:
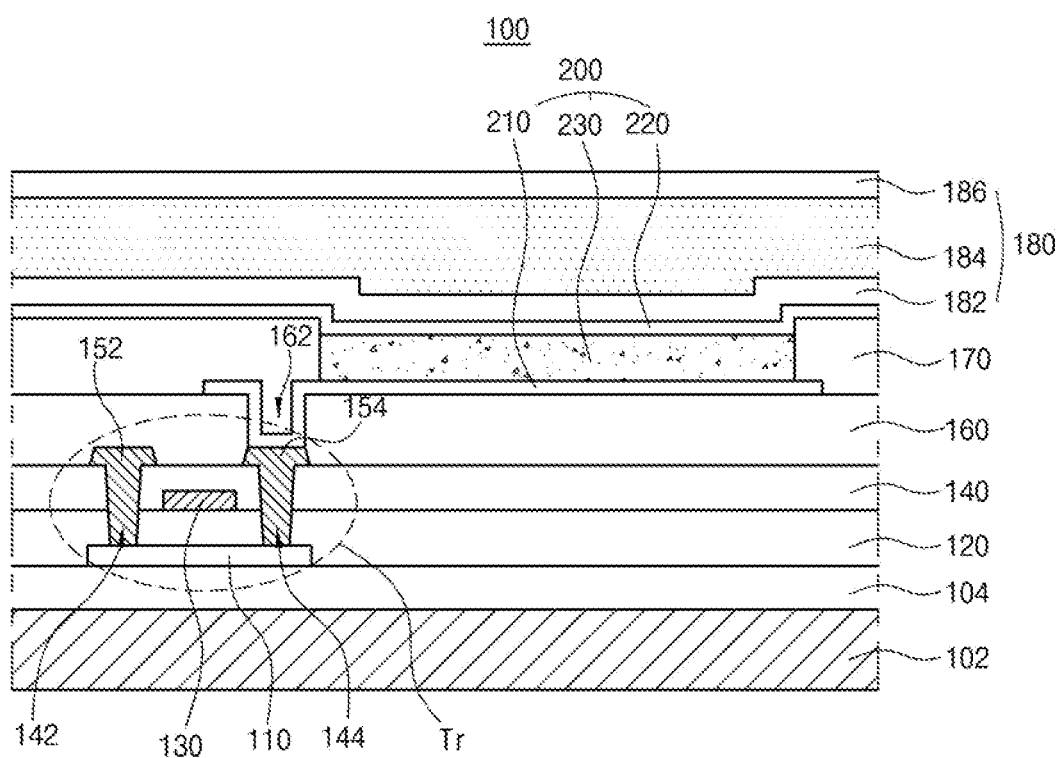
FIG. 1 is a schematic cross-sectional view illustrating an organic light emitting display device of the present disclosure.

An organic light emitting diode of the present disclosure includes at least one exciton energy control layer, which includes an organic compound without doping, disposed adjacent to at least one emitting material layer so as to enhance its luminous efficiency and luminous lifetime. The organic light emitting diode of the present disclosure can be applied to an organic light emitting device such as an organic light emitting display device and an organic light emitting illumination device. A display device including the organic light emitting diode will be explained. FIG. 1 is a schematic cross-sectional view of an organic light emitting display device of the present disclosure. All components of the organic light emitting display device according to all embodiments of the present disclosure are operatively coupled and configured.

In other words, it may be said that two electrodes are facing each other when the surface of either electrode that is closest to the other electrode are substantially parallel to each other and overlapping such that perpendicular line from said surface of one of the electrodes passes through said surface of the other electrode As illustrated in FIG. 1, the organic light emitting display device 100 includes a substrate 102, a thin-film transistor Tr on the substrate 102, and an organic light emitting diode 200 connected to the thin film transistor Tr.

The substrate 102 can include, but is not limited to, glass, thin flexible material and/or polymer plastics. For example, the flexible material can be selected from the group, but is not limited to, polyimide (PI), polyethersulfone (PES), polyethylenenaphthalate (PEN), polyethylene terephthalate (PET), polycarbonate (PC) and combination thereof. The substrate 102, over which the thin film transistor Tr and the organic light emitting diode 200 are arranged, forms an array substrate.

A buffer layer 104 can be disposed over the substrate 102, and the thin film transistor Tr is disposed over the buffer layer 104. The buffer layer 104 can be omitted.

A semiconductor layer 110 is disposed over the buffer layer 104. In one exemplary embodiment, the semiconductor layer 110 can include, but are not limited to, oxide semiconductor materials. In this case, a light-shield pattern can be disposed under the semiconductor layer 110, and the light-shield pattern can prevent light from being incident toward the semiconductor layer 110, and thereby, preventing the semiconductor layer 110 from being deteriorated by the light. Alternatively, the semiconductor layer 110 can include, but are not limited to, polycrystalline silicon. In this case, opposite edges of the semiconductor layer 110 can be doped with impurities.

A gate insulating layer 120 formed of an insulating material is disposed on the semiconductor layer 110. The gate insulating layer 120 can include, but are not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 can be patterned identically as the gate electrode 130.

An interlayer insulating layer 140 formed of an insulating material is disposed on the gate electrode 130 with covering over an entire surface of the substrate 102. The interlayer insulating layer 140 can include, but are not limited to, an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over opposite sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, which are formed of a conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr can have an inverted staggered structure in which a gate electrode is disposed under a semiconductor layer and a source and drain electrodes are disposed over the semiconductor layer. In this case, the semiconductor layer can comprise amorphous silicon.

In FIG. 1, a gate line and a data line, which cross each other to define a pixel region, and a switching element, which is connected to the gate line and the data line is, can be further formed in the pixel region. The switching element is connected to the thin film transistor Tr, which is a driving element. Besides, a power line is spaced apart in parallel from the gate line or the data line, and the thin film transistor Tr can further include a storage capacitor configured to constantly keep a voltage of the gate electrode for one frame.

In addition, the organic light emitting display device 100 can include a color filter for absorbing a part of the light emitted from the organic light emitting diode 200. For example, the color filter can absorb a light of specific wavelength such as red (R), green (G) or blue (B). In this case, the organic light emitting display device 100 can implement full-color through the color filter.

For example, when the organic light emitting display device 100 is a bottom-emission type, the color filter can be disposed on the interlayer insulating layer 140 with corresponding to the organic light emitting diode 200. Alternatively, when the organic light emitting display device 100 is a top-emission type, the color filter can be disposed over the organic light emitting diode 200, that is, a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 144, it can be spaced apart from the second semiconductor layer contact hole 144.

The organic light emitting diode 200 includes a first electrode 210 that is disposed on the passivation layer 160 and connected to the drain electrode 154 of the thin film transistor Tr. The organic light emitting diode 200 further includes an emitting unit 230 as an emission layer and a second electrode 220 each of which is disposed sequentially on the first electrode 210.

The first electrode 210 is disposed in each pixel region. The first electrode 210 can be an anode and include a conductive material having a relatively high work function value. For example, the first electrode 210 can include, but are not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary embodiment, when the organic light emitting display device 100 is a top-emission type, a reflective electrode or a reflective layer can be disposed under the first electrode 210. For example, the reflective electrode or the reflective layer can include, but are not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

An emitting unit 230 is disposed on the first electrode 210. In one exemplary embodiment, the emitting unit 230 can have a mono-layered structure of an emitting material layer. As an example, the emitting material layer can include at least one emitting material layer having a host and a dopant and at least one exciton energy control layer disposed adjacently to the at least one emitting material layer.

Alternatively, the emitting unit 230 can have a multi-layered structure of a hole injection layer, a hole transport layer, an electron blocking layer, an emitting material layer, a hole blocking layer, an electron transport layer and/or an electron injection layer (See, FIGS. 2, 6, 8, 11, 13, 15, 17 and 19). In one embodiment, the organic light emitting diode 200 can have one emitting unit 230. Alternatively, the organic light emitting diode 200 can have multiple emitting units 230 to form a tandem structure.

The second electrode 220 is disposed over the substrate 102 above which the emitting unit 230 is disposed. The second electrode 220 can be disposed over a whole display area and can include a conductive material with a relatively low work function value compared to the first electrode 210. The second electrode 220 can be a cathode. For example, the second electrode 220 can include, but are not limited to, aluminum (Al), magnesium (Mg), calcium (Ca), silver (Ag), alloy thereof or combination thereof such as aluminum-magnesium alloy (Al—Mg).

In addition, an encapsulation film 180 can be disposed over the second electrode 220 in order to prevent outer moisture from penetrating into the organic light emitting diode 200. The encapsulation film 180 can have, but are not limited to, a laminated structure of a first inorganic insulating film 182, an organic insulating film 184 and a second inorganic insulating film 186.

Organic Light Emitting Diode

Figure 2:
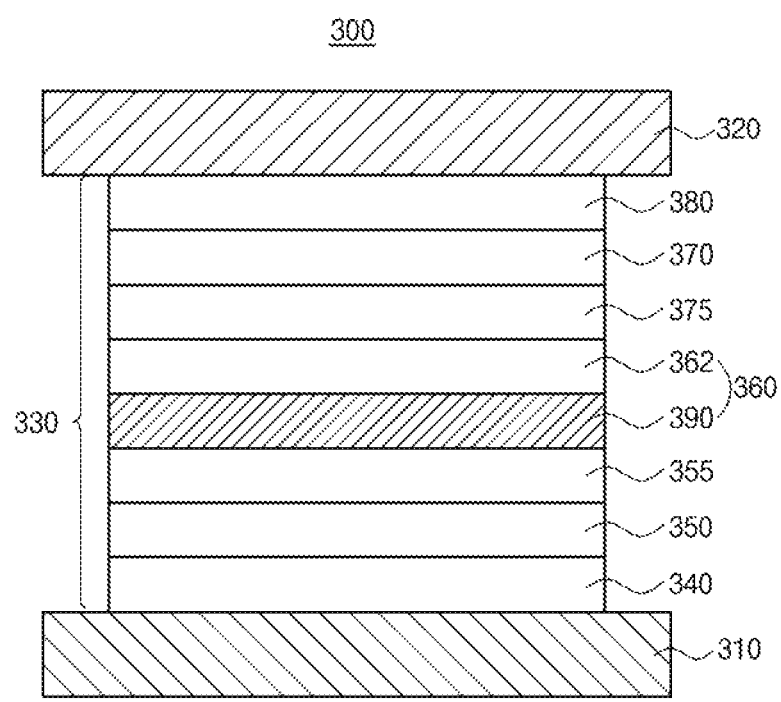
FIG. 2 is a schematic cross-sectional view illustrating an organic light emitting diode in accordance with an exemplary embodiment of the present disclosure.

An organic light emitting diode of the present disclosure introduces at least one exciton energy control layer, which includes or consists of an organic compound, disposed adjacently at least one emitting material layer so that the OLED can enhance its luminous efficiency and maximize its luminous lifetime. FIG. 2 is a schematic cross-sectional view illustrating an organic light emitting diode in accordance with an exemplary embodiment of the present disclosure. As illustrated in FIG. 2, the organic light emitting diode (OLED) 300 in accordance with the first embodiment of the present disclosure includes first and second electrodes 310 and 320 facing each other and an emitting unit 330 as an emission layer disposed between the first and second electrodes 310 and 320. In one exemplary embodiment, the emitting unit 330 include a hole injection layer HIL 340, a hole transport layer HTL 350, an emitting material layer EML 360, an electron transport layer ETL 370 and an electron injection layer EIL 380 each of which is laminated sequentially from the first electrode 310. Alternatively, the emitting unit 330 can further comprise a first exciton blocking layer, i.e. an electron blocking layer (EBL) 355 disposed between the HTL 350 and the EML 360 and/or a second exciton blocking layer, i.e. a hole blocking layer (HBL) 375 disposed between the EML 360 and the ETL 370.

The first electrode 310 can be an anode that provides a hole into the EML 360. The first electrode 310 can include, but are not limited to, a conductive material having a relatively high work function value, for example, a transparent conductive oxide (TCO). In an exemplary embodiment, the first electrode 310 can include, but are not limited to, ITO, IZO, ITZO, SnO, ZnO, ICO, AZO, and the like.

The second electrode 320 can be a cathode that provides an electron into the EML 360. The second electrode 320 can include, but are not limited to, a conductive material having a relatively low work function values, i.e., a highly reflective material such as Al, Mg, Ca, Ag, alloy thereof, combination thereof, and the like. As an example, each of the first and second electrodes 310 and 320 can be laminated with a thickness of, but are not limited to, about 30 to about 300 nm.

The HIL 340 is disposed between the first electrode 310 and the HTL 350 and improves an interface property between the inorganic first electrode 310 and the organic HTL 350. In one exemplary embodiment, the HIL 340 can include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino)triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3"-h]quinoxaline-2,3,6,7,10,11-hexacarbonitrile; HAT-CN), 1,3,5-tris[4-(diphenylamino)phenyl]benzene (TDAPB), poly(3,4-ethylenedioxythiophene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 340 can be omitted in compliance with a structure of the OLED 300. Of these compounds, HAT-CN is preferred in the HIL 340.

The HTL 350 is disposed adjacently to the EML 360 between the first electrode 310 and the EML 360. In one exemplary embodiment, the HTL 350 can include, but are not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis(phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), 3,5-di(9H-carbazol-9-yl)-N,N-diphenyl aniline (DCDPA), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine. Of these compounds, NPB is preferred in the HTL 350.

In one exemplary embodiment, each of the HIL 340 and the HTL 350 can be laminated with a thickness of, but are not limited to, about 5 to about 200 nm, and preferably about 5 to about 100 nm.

The EML 360 includes a first emitting material layer (EML1) 362 and an exciton energy control layer (EEL) 390 disposed adjacently to the EML1 362. The EML1 362 includes a host and a dopant. The EEL 390 can be disposed between the EBL 355 and the EML1 362 or between the EML1 362 and the HBL 375. The EEL 390 include an organic compound having a predetermined energy level. As an example, the EEL 390 consists of the organic compound. The configuration and energy levels of the EML 360, including the EEL 390, will be explained in more detail below.

The ETL 370 and the EIL 380 are laminated sequentially between the EML 360 and the second electrode 320. The ETL 370 can include a material having high electron mobility so as to provide electrons stably with the EML 360 by fast electron transportation.

In one exemplary embodiment, the ETL 370 can include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 370 can include, but are not limited to, tris-(8-hydroxyquinoline aluminum) ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenyl-benzimidazol-2-yl)benzene (TPBi), Bis(2-methyl-8-quinolinato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenanthroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl) 1,3,5-triazine (TmPPPyTz), Poly[9,9-bis(3'-(N,N-dimethyl)-N-ethylammonium)-propyl]-2,7-fluorene]-alt-2,7-(9,9-dioctylfluorene)] (PFNBr), tris(phenylquinoxaline) (TPQ), diphenyl-4-triphenylsilyl-phenylphosphine oxide (TSPO1) and/or 2-[4-(9,10-di-2-naphthalenyl-2-anthracenyl)phenyl]-1-phenyl-1H-benzimidazole. Of these compounds, 2-[4-(9,10-di-2-naphthalenyl-2-anthracenyl)phenyl]-1-phenyl-1H-benzimidazole is preferred in the ETL 370.

The EIL 380 is disposed between the second electrode 320 and the ETL 370, and can improve physical properties of the second electrode 320 and therefore, can enhance the life span of the OLED 300. In one exemplary embodiment, the EIL 380 can include, but are not limited to, an alkali halide such as LiF, CsF, NaF, $BaF_2$ and the like, and/or an organic metal compound such as lithium benzoate, sodium stearate, and the like.

As an example, each of the ETL 370 and the EIL 380 can be laminated with a thickness of, but are not limited to, about 10 to about 200 nm, and preferably about 10 to about 100 nm.

When holes are transferred to the second electrode 320 via the EML 360 and/or electrons are transferred to the first electrode 310 via the EML 360, the luminous lifetime and the luminous efficiency of the OLED 300 can be reduced. In order to prevent those phenomena, the OLED 300 in accordance with this embodiment of the present disclosure has at least one exciton blocking layer disposed adjacently to the EML 360.

For example, the OLED 300 of the exemplary embodiment includes the EBL 355 between the HTL 350 and the EML 360 so as to control and prevent electron transfers. In one exemplary embodiment, the EBL 355 can include, but are not limited to, TCTA, Tris[4-(diethylamino)phenyl] amine, N-(biphneyl-4-yl)-9,9-dimethyl-N-(4-(9-phenyl-9H- carbazol-3-yl)phenyl)-9H-fluorene-2-amine, TAPC, MTDATA, 1,3-bis(carbazol-9-yl)benzene (mCP), 3,3'-bis(N-carbazolyl)-1,1'-biphenyl (mCBP), CuPc, N,N'-bis[4-(bis(3-methylphenyl)amino)phenyl]-N,N'-diphenyl-[1,1'-biphenyl]-4,4'-diamine (DNTPD), TDAPB, DCDPA, 2,8-bis(9-phenyl-9H-carbazol-3-yl)dibenzo[b,d]thiophene and/or 3,6-bis(N-carbazolyl)-N-phenyl-carbazole, Of these compounds, TCTA is preferred in the EBL 355.

In addition, the OLED 300 further includes the HBL 375 as a second exciton blocking layer between the EML 360 and the ETL 370 so that holes cannot be transferred from the EML 360 to the ETL 370. In one exemplary embodiment, the HBL 375 can include, but are not limited to, oxadiazole-based compounds, triazole-based compounds, phenanthroline-based compounds, benzoxazole-based compounds, benzothiazole-based compounds, benzimidazole-based compounds, and triazine-based compounds.

For example, the HBL 375 can include a compound having a relatively low HOMO energy level compared to the emitting material in EML 360. The HBL 375 can include, but are not limited to, BCP, BAlq, Alq$_3$, PBD, spiro-PBD, Liq, Bis-4,5-(3,5-di-3-pyridylphenyl)-2-methylpyrimidine (B3PYMPM), DPEPO, 9-(6-(9H-carbazol-9-yl)pyridine-3-yl)-9H-3,9'-bicarbazole, TSPO1 and combination thereof.

As schematically described above, the EML 360 in the OLED 300 includes the EML1 362 including the host and the dopant and EEL 390 including an organic compound and disposed adjacently to the EML1 362. As used herein, an organic compound used in the EELs without doping will be referred as "organic compounds" or "exciton dopant (ED)" in order to distinguish the dopant which is used together with the host.

In one exemplary embodiment, each of the dopant in the EML1 362 and the organic compound in the EEL 390 can be a delayed fluorescent material, respectively. As the EML 360 includes the delayed fluorescent material as the dopant and the organic compound, the OLED 300 can enhance its luminous efficiency, lower its driving voltage and improve its luminous lifetime.

An Organic Light Emitting Diode (OLED) emits light as holes injected from the anode and electrons injected from the cathode are combined to form excitons in EML and then unstable excited state excitons return to a stable ground state. Theoretically, when electrons meet holes to form exciton, a singlet exciton of a paired spin and a triplet exciton of an unpaired spin are produced by a ratio of 1:3 by spin arrangements. Only the singlet exciton among the excitons can be involved in emission process in case of fluorescent materials. Accordingly, the OLED can exhibit luminous efficiency by maximum 5% in case of using the common fluorescent material.

In contrast, phosphorescent materials use different luminous mechanism of converting both singlet excitons and triplet exciton into light. The phosphorescent materials can convert singlet excitons into triplet excitons through inter-system crossing (ISC). Therefore, it is possible to enhance luminous efficiency in case of applying the phosphorescent materials that use both the singlet excitons and the triplet excitons during the luminous process compared to the fluorescent materials. However, related art blue phosphorescent materials exhibits too low color purity to apply with the display device and exhibit very short luminous lifetime, and therefore, they have not been used in commercial display devices.

A delayed fluorescent material, which can solve the limitations accompanied by the related art fluorescent dopants and the phosphorescent dopants, has been developed recently. Representative delayed fluorescent material is a thermally-activated delayed fluorescent (TADF) material. Since the delayed fluorescent material generally has both an electron donor moiety and an electron acceptor moiety within its molecular structure, it can be converted to an intramolecular charge transfer (ICT) state. In case of using the delayed fluorescent material as a dopant, it is possible to use both the excitons of singlet energy level $S_1$ and the excitons of triplet energy level $T_1$ during the emission process.

Figure 3:
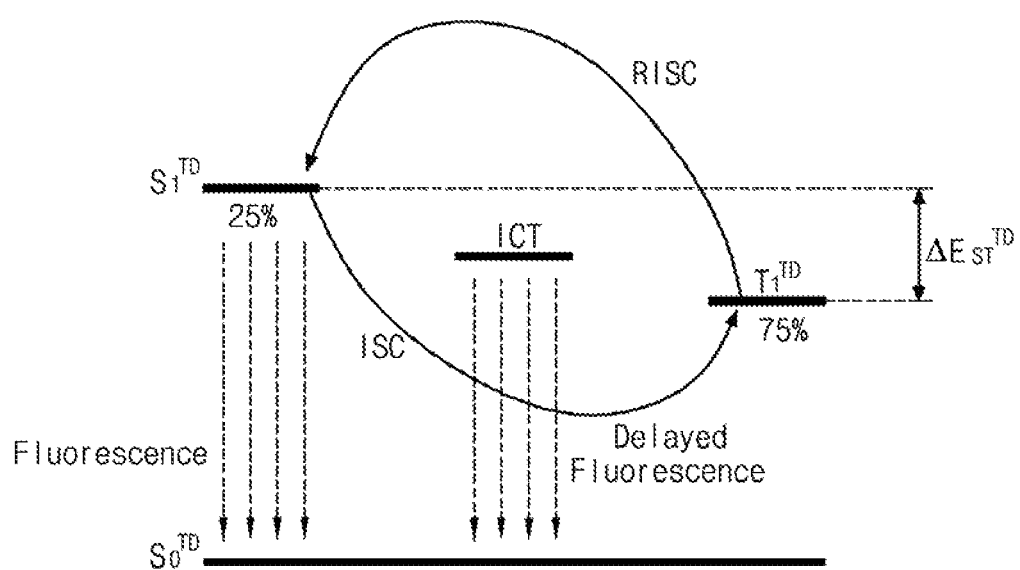
FIG. 3 is a schematic diagram illustrating a luminous mechanism of a delayed fluorescent material.

The luminous mechanism of the delayed fluorescent material will be explained with referring to FIG. 3, which is a schematic diagram illustrating a luminous mechanism of the delayed fluorescent material in an EML in accordance with an exemplary embodiment of the present disclosure. As illustrated in FIG. 3, the exciton of singlet energy level $S_1^{TD}$ emits light as fluorescence. The exciton of triplet energy level $T_1^{TD}$ is a CT state which can be converted to an intermediate energy level state, i.e. ICT state. Since the ICT state have both singlet and triplet characteristics, the triplet exciton at ICT state can be converted to singlet exciton by reverse intersystem crossing (RISC), and then the converted singlet exciton can be transferred to a ground state $S_0$. Since the excitons of singlet energy level $S_1^{TD}$ as well as the excitons of triplet energy level $T_1^{TD}$ in the delayed fluorescent material is involved in the emission process, the delayed fluorescent material can improve luminous efficiency such as internal quantum efficiency.

Because both the HOMO and the LUMO are widely distributed over the whole molecule within the related art fluorescent material, it is not possible to inter-convert between the singlet energy level and the triplet energy level within it (selection rule). In contrast, since the delayed fluorescent material, which can be converted to ICT state, has little orbital overlaps between HOMO and LUMO, there is little interaction between the HOMO state molecular orbital and the LUMO state molecular orbital in the state where dipole moment is polarized within the delayed fluorescent material. As a result, the changes of spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, it exists as a polarized state having a large dipole moment within the molecule. As the interaction between HOMO molecular orbital and LUMO molecular orbital becomes little in the state where the dipole moment is polarized, both the triplet energy level excitons and the singlet energy level excitons can be converted to ICT state. Accordingly, the excitons of triplet energy level $T_1$ as well as the excitons of singlet energy level $S_1$ can be involved in the emission process.

In case of driving the diode that includes the delayed fluorescent material, 25% excitons of singlet energy level $S_1^{TD}$ and 75% excitons of triplet energy level $T_1^{TD}$ are converted to ICT state by heat or electrical field, and then the converted excitons transfer to the ground state $S_0$ with luminescence. Therefore, the delayed fluorescent material can have 100% internal quantum efficiency in theory.

The delayed fluorescent material must has an energy level bandgap $\Delta E_{ST}^{TD}$ equal to or less than about 0.3 eV, for example, from about 0.05 to about 0.3 eV, between the singlet energy level $S_1^{TD}$ and the triplet energy level $T_1^{TD}$ so that exciton energy in both the singlet energy level and the triplet energy level can be transferred to the ICT state. The material having little energy level bandgap between the singlet energy level $S_1^{TD}$ and the triplet energy level $T_1^{TD}$ can exhibit common fluorescence in which the excitons of singlet energy level $S_1^{TD}$ can be drop to the ground state $S_0$, as well as delayed fluorescence with Reverse Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be transferred to the ground state $S_0$.

Figure 4:
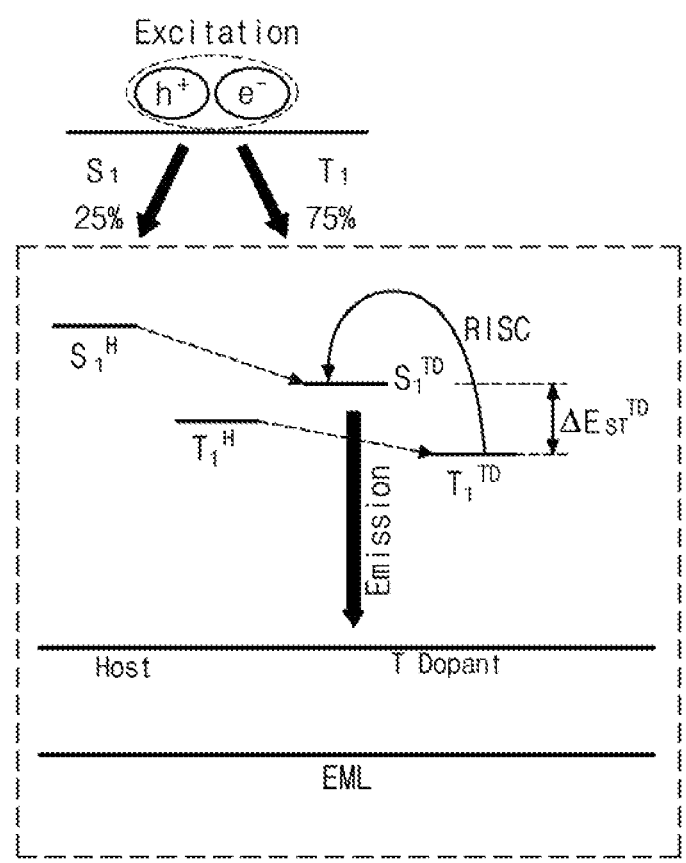
FIG. 4 is a schematic diagram illustrating luminous mechanism by energy level bandgap among luminous materials in accordance with the related art.

The delayed fluorescent material can realize identical quantum efficiency as the related art phosphorescent material including heavy metal because the delayed fluorescent material can obtain luminous efficiency up to 100% in theory. However, when the EML includes only the host and the delayed fluorescent material, there can be the following disadvantages. FIG. 4 is a schematic diagram illustrating luminous mechanism by energy level bandgap among luminous materials in accordance with the related art As illustrated in FIG. 4, each of exciton energy at an excited state singlet energy level $S_1^H$ and exciton energy at an excited stat triplet energy level $T_1^H$ of the host is transferred to each of an excited state singlet energy level $S_1^{TD}$ and an excited state triplet energy level $T_1^{TD}$ of the delayed fluorescent material in the same EML by Dexter energy transfer mechanism, which transfer exciton energies depending upon wave function overlaps among adjacent molecules by inter-molecular electron exchanges and exciton diffusions, respectively. The exciton energy at the excited state triplet energy level $T_1^{TD}$ of the dopant as the delayed fluorescent material is converted to the excited state singlet energy level $S_1^{TD}$ by RISC mechanism, and then the converted exciton energy at the excited state singlet energy level $S_1^{TD}$ is transferred to the ground state as a delayed fluorescence.

However, the rate of converting the exciton energy at the triplet energy level $T_1^{TD}$ to the singlet energy level $S_1^{TD}$ by RISC is relatively slow compared to the rate of transferring exciton energy from excited state singlet and triplet energy levels $S_1^H$ and $T_1^H$ of the host to excited state singlet and triplet energy levels $S1^{TD}$ and $T_1^{TD}$ of the delayed fluorescent material. As a result, a part of exciton energy at the excited state singlet and triplet energy levels $S_1^H$ and $T_1^H$ of the host is not transferred to the delayed fluorescent material. In this case, exciton quenching occurs due to the interaction between the host excitons, which is accumulated at the host without being transferred to the delayed fluorescent materials, and the peripheral polaron, and lifetime of an OLED is reduced by electro-oxidation and photo-oxidation.

Figure 5:
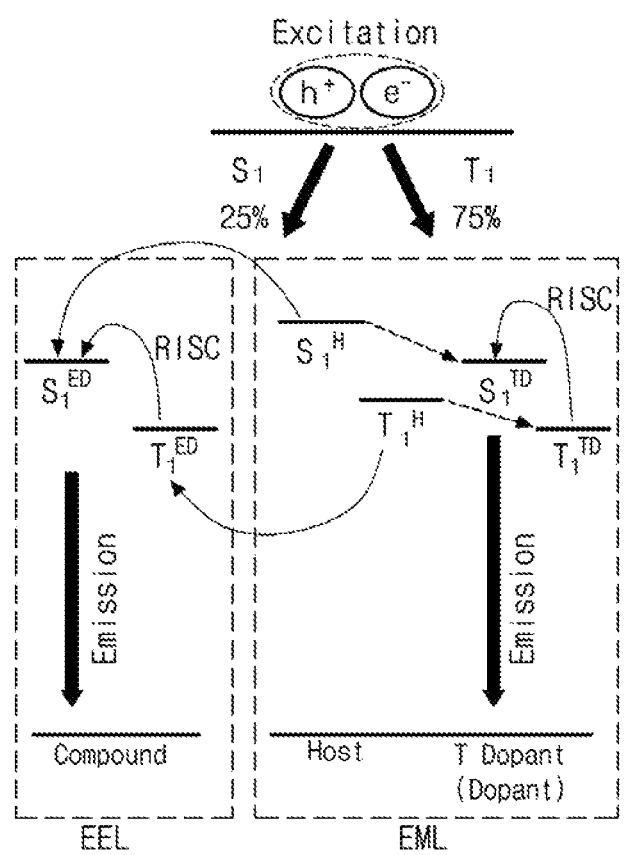
FIG. 5 is a schematic diagram illustrating luminous mechanism by energy level bandgap among luminous materials in accordance with an exemplary embodiment of the present disclosure.

On the contrary, the OLED 300 introduces the exciton energy control layer (EEL) so as to enhance its luminous efficiency and its luminous lifetime. FIG. 5 is a schematic diagram illustrating luminous mechanism by energy level bandgap among luminous materials in accordance with an exemplary embodiment of the present disclosure.

The host for implementing a delayed fluorescence should have predetermined energy levels so that the triplet exciton at the dopant can be involved in the luminous process without quenching as a non-emission. Each of an excited state singlet energy level $S_1^H$ and an excited state triplet energy level $T_1^H$ of the host in the EML1 362 should be higher than each of an excited state singlet energy level $S_1^{TD}$ and an excited state triplet energy level $T_1^{TD}$ of the dopant (T dopant) as a delayed fluorescent material, respectively. As an example, the excited state triplet energy level $T_1^H$ of the host can be higher than the excited state triplet energy level $T_1^{TD}$ of the dopant by at least about 0.2 eV.

As an example, when each of the excited state singlet energy level $S_1^H$ and the excited state triplet energy level $T_1^H$ of the host is not higher enough than each of the excited state singlet energy level $S_1^{TD}$ and the excited state triplet energy levels $T_1^{TD}$ of the dopant, which can be a delayed fluorescent material, the excitons of the singlet energy level $S_1^{TD}$ of the dopant can be reversely transferred to the excited state singlet energy level $S_1^H$ of the host, or the excitons of the triplet energy level $T_1^{TD}$ of the dopant can be reversely transferred to the excited state triplet energy level $T_1^H$ of the host.

When the excitons of the triplet energy level $T_1^{TD}$ of the dopant can be reversely transferred to the excited state triplet energy level $T_1^H$ of the host, which cannot utilize triplet exciton energy, the excitons of the triplet energy level $T_1^{TD}$ of the dopant can be quenched as a non-emission and the triplet state excitons of the dopant cannot be involved in the emission. As an example, the host can have an excited state singlet energy level $S_1^H$ equal to or more than about 2.9 eV and an excited state triplet energy level $T_1^H$ equal to or more than about 2.8 eV, but are not limited thereto.

On the contrary, the dopant as a delayed fluorescent material can have an excited state singlet energy level $S_1^{TD}$ between about 2.4 and about 2.7 eV and an excited state triplet energy level $T_1^{TD}$ between about 1.8 about 2.2 eV, but are not limited thereto. An energy level bandgap $\Delta_{ST}^{TD}$ between the excited state singlet energy level $S_1^{TD}$ and the excited state triplet energy level $T_1^{TD}$ of the dopant which has a delayed fluorescent property can be equal to or less than about 0.3 eV, for example, between about 0.05 and about 0.3 eV (See, FIG. 3).

In addition, it is necessary to adjust properly HOMO energy levels and LUMO energy levels of the host and the dopant, which can be the fluorescent material. For example, it is preferable that an energy level bandgap ($|HOMO^H - HOMO^{TD}|$) between a HOMO energy level ($HOMO^H$) of the host and a HOMO energy level ($HOMO^{TD}$) of the dopant, or an energy level bandgap ($|LUMO^H - LUMO^{TD}|$)) between a LUMO energy level ($LUMO^H$) of the host and a LUMO energy level ($LUMO^{TD}$) of the dopant can be equal to or less than about 0.5 eV, for example, between about 0.1 eV to about 0.5 eV. In this case, the charges can be transported efficiently from the host to the dopant and thereby enhancing an ultimate luminous efficiency.

Moreover, an energy level bandgap ($Eg^H$) between the HOMO energy level ($HOMO^H$) and the LUMO energy level ($LUMO^H$) of the host can be larger than an energy level bandgap ($Eg^{TD}$) between the HOMO energy level ($HOMO^{TD}$) and the LUMO energy level ($LUMO^{TD}$) of the dopant. As an example, the HOMO energy level ($HOMO^H$) of the host is deeper or lower than the HOMO energy level ($HOMO^{TD}$) of the dopant, and the LUMO energy level ($LUMO^H$) of the host is shallower or higher than the LUMO energy level ($LUMO^{TD}$) of the dopant.

Since the rate of converting triplet exciton to singlet exciton in the dopant by RISC mechanism is slow compared to the rate of transferring exciton energy from the host to the dopant, a part of exciton energy of the host can be accumulated at the host without transferring to the dopant, as described above. However, the EEL 390 including the organic compound is disposed adjacently to the EML1 362 in accordance with the first embodiment of the present disclosure so as to prevent the exciton energy from being quenched.

A part of exciton energy, accumulated at the excited state singlet energy level $S_1^H$ and the excited state triplet energy level $T_1^H$ of the host without being transferred to the dopant in the EML1 362, can be transferred to an excited state singlet energy level $S_1^{ED}$ and an excited state triplet energy level $T_1^{ED}$ of the organic compound in the EEL 390 which is disposed adjacently to the EML1 362 by FRET (Forster resonance energy transfer) mechanism, which transfers energy non-radially through electrical fields by dipole-dipole interactions. As a part of exciton energy of the host, which is not transferred to the dopant, is transferred to the organic compound, the exciton energy of the host without being transferred to the dopant is not accumulated at the host. As a result, exciton quenching caused by interaction between the accumulated host excitons and the peripheral polaron can be minimized and lifetime reduction of the OLED 300 owing to the electro-oxidation and the photo-oxidation in the course of exciton quenching can be prevented.

In one exemplary embodiment, the organic compound in the EEL 390 can be a delayed fluorescent material so as to receive exciton energies from the host. In this case, the organic compound can utilize the triplet exciton energy as well as the singlet exciton energy transferred from the host so that the EML 360 can improve its luminous efficiency. In one exemplary embodiment, each of the excited stat singlet energy level $S_1^{ED}$ and the excited state triplet energy level $T_1^{ED}$ of the organic compound is lower than each of the excited state singlet energy level $S_1^H$ and the excited state triplet energy level $T_1^H$ of the host, respectively.

When each of the excited state singlet energy level $S_1^H$ and the excited state triplet energy level $T_1^H$ of the host is not higher enough than each of the excited state singlet energy level $S_1^{ED}$ and the excited state triplet energy levels $T_1^{ED}$ of the organic compound (first exciton dopant), which can be a delayed fluorescent material, the excitons of the singlet and triplet energy levels $S_1^{ED}$ and $T_1^{ED}$ of the organic compound can be reversely transferred to the excited state singlet and triplet energy level $S_1^H$ and $T_1^H$ of the host.

Moreover, it can be necessary to adjust the HOMO and LUMO energy levels of the host and the organic compound in order to prevent holes and/or electrons from being trapped in the EML1 362 and the EEL 390. As an example, it is preferable that an energy level bandgap ($|HOMO^H–HOMO^{ED}|$) between a HOMO energy level ($HOMO^H$) of the host and a HOMO energy level ($HOMO^{ED}$) of the organic compound, or an energy level bandgap ($|LUMO^H–LUMO^{ED}|$) between a LUMO energy level ($LUMO^H$) of the host and a LUMO energy level ($LUMO^{ED}$) of the organic compound can be equal to or less than about 0.2 eV, for example, between about 0.01 eV to about 0.2 eV.

The exciton energy of the host in the EML1 362 should be efficiently transferred to the organic compound in the EEL 390 disposed adjacently to the EML1 362. As an example, the EEL 390 can be laminated with a thickness of, but are not limited to, about 1 to about 10 nm, and preferably about 1 to about 5 nm.

In one exemplary embodiment, the organic compound can be an organic compound that can emit light without doping treatment. As an example of self luminescence without doping, a material which can implement Aggregation-Induced Emission (AIE) can be used as the organic compound. As an example, the organic compound can include, but are not limited to, an organic compound having the following vinylene-arylene structure of Chemical Formula 1:

Chemical Formula 1

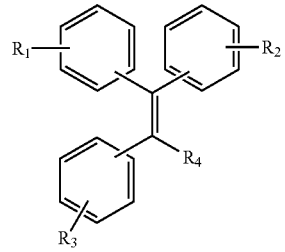

In Chemical Formula 1, each of $R_1$ to $R_3$ is independently protium, deuterium, tritium, $C_5$~$C_{30}$ aryl group unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group, or $C_4$~$C_{30}$ hetero aryl group unsubstituted or substituted with cyano group, nitro group, halogen, $C_1$~$C_{10}$ alkyl group, $C_1$~$C_{10}$ alkyl halide group. $C_5$~$C_{30}$ aryl group or $C_4$~$C_{30}$ hetero aryl group. $R_4$ is protium, deuterium, tritium or phenyl group unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group.

As used herein, the term "unsubstituted" means that hydrogen atom is bonded, and in this case hydrogen atom comprises a protium, deuterium and tritium.

As used herein, the term "hetero" described in "hetero aromatic ring", "hetero aromatic group", "hetero alicyclic ring", "hetero cyclic alkyl group", "hetero aryl group", "hetero aralkyl group", "hetero aryloxyl group", "hetero aryl amino group", "hetero arylene group", "hetero aralkylene group", "hetero aryloxylene group", and the likes means that at least one carbon atoms, for example 1 to 5 carbon atoms, forming such aromatic or alicyclic rings are substituted with at least one hetero atoms selected from the group consisting of N, O, S and combination thereof.

As an example, the $C_5$~$C_{30}$ aryl group which constitutes independently each of $R_1$ to $R_3$ or with which $R_1$ to $R_4$ are substituted independently, can be, but are not limited to, an unfused or a fused aryl group such as phenyl, biphenyl, terphenyl, naphthyl, anthracenyl, pentalenyl, indenyl, indeno-indenyl, heptaleneyl, biphenylenyl, indacenyl, phenalenyl, phenanthrenyl, benzo-phenanthrenyl, dibenzo-phenanthrenyl, azulenyl, pyreneyl, fluoranthenyl, triphenylenyl, chrysenyl, tetraphenyl, tetracenyl, pleiadenyl, picenyl, pentaphenyl, pentacenyl, fluorenyl, indeno-fluorenyl or spiro-fluorenyl.

In an alternative embodiment, the $C_4$~$C_{30}$ hetero aryl group, which constitutes independently each of $R_1$ to $R_3$ or with which $R_1$ to $R_4$ are substituted independently, can be, but are not limited to, an unfused or a fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzo-carbazolyl, dibenzo-carbazolyl, indolo-carbazolyl, indeno-carbazolyl, benzofuro-carbazolyl, benzothieno-carbazolyl, quinolinyl, iso-quinolinyl, phthalazinyl, quinoxalinyl, cinnolinyl, quinazolinyl, quinozolinyl, quinolizinyl, benzo-quinazolinyl, benzo-quinoxalinyl, acridinyl, phenanthrolinyl, perimidinyl, phenanthridinyl, pteridinyl, naphthyridinyl, furanyl, pyranyl, oxazinyl, oxazolyl, oxadiazolyl, triazolyl, dioxinyl, benzo-furnanyl, dibenzo-furanyl, thiopyranyl, xanthenyl, chromenyl, iso-chromenyl, thiazinyl, thiophenyl, benzo-thiophenyl, dibenzo-thiophenyl, difuro-pyrazinyl, benzofuro-dibenzo-furanyl, benzothieno-benzo-thiophenyl, benzothieno-dibenzo-furanyl, benzothieno-benzo-furanyl, benzothieno-dibenzo-furanyl or N-substituted spiro-fluorenyl.

In one exemplary embodiment, the aryl or the hetero aryl group, which constitutes independently each of $R_1$ to $R_3$ or with which $R_1$ to $R_4$ are substituted independently, can consist of 1 to 3 aromatic or hetero aromatic rings. If the number of aromatic or hetero aromatic rings, which constitutes independently each of $R_1$ to $R_3$ or with which $R_1$ to $R_4$ are substituted independently, becomes too large, the conjugated structure in the whole organic compound is too long, and as a result, the energy level bandgap of the organic compound can be excessively decreased. As an example, the aromatic or the hetero aromatic group, which constitutes independently each of $R_1$ to $R_3$ or with which $R_1$ to $R_4$ are substituted independently, can be, but are not limited to, phenyl, biphenyl, pyrrolyl, triazinyl, imidazolyl, pyrazolyl, pyridinyl, pyrazinyl, pyrimidinyl, pyridazinyl, furanyl, benzofuranyl, dibenzofuranyl, thiophenyl, benzothiophenyl, dibenzothiophenyl and carbazolyl, each of which is unsubstituted or substituted with cyano group, nitro group, halogen, $C_1$~$C_{10}$ alkyl group. $C_1$~$C_{10}$ alkyl halide group. $C_5$~$C_{30}$ aryl group or $C_4$~$C_3$ hetero aryl group.

In one exemplary embodiment, the aryl or the hetero aryl group, which constitutes independently each of $R_1$ to $R_3$ or with which $R_1$ to $R_4$ are substituted independently, can be directly bonded to the phenylene or phenyl moiety, or bonded to the phenylene or phenyl moiety through $C_5$-$C_{30}$ arylene or $C_4$~$C_{30}$ hetero arylene. If the number of aromatic or hetero aromatic rings of the $C_5$~$C_{30}$ arylene or $C_4$~$C_{30}$ hetero arylene between the phenylene or phenyl moiety and the aryl or the hetero aryl group becomes too large, the conjugated structure in the whole organic compound is too long, and as a result, the energy level bandgap of the organic compound can be excessively decreased. Accordingly, the number of aromatic or hetero aromatic rings of the $C_5$~$C_{30}$ arylene or $C_4$~$C_{30}$ hetero arylene between the phenylene or phenyl moiety and the aryl or the hetero aryl group is 1 or 2, preferably 1.

In one exemplary embodiment, $R_4$ is an unsubstituted or substituted phenyl group.

In one exemplary embodiment, $R_1$ to $R_3$ are aryl groups.

With regard to charge injection and transportation properties, the aromatic or hetero aromatic ring of $C_5$~$C_{30}$ arylene or $C_4$~$C_{30}$ hetero arylene between the phenylene or phenyl moiety and the aryl or the hetero aryl group can be 5-membered ring to 7-membered ring, preferably 6-membered ring. As an example, the $C_5$~$C_{30}$ arylene or $C_4$~$C_{30}$ hetero arylene between the phenylene or phenyl moiety and the aryl or the hetero aryl group can independently, but are not limited to, phenylene, biphenylene, pyrrolylene, imidazolylene, pyrazolylene, pyridinylene, pyrazinylene, pyrimidinylene, pyridazinylene, furanylene or thiophenylene.

As an example, the organic compound in the EEL 390 disposed adjacently to the EML1 362 can be a delayed fluorescent material in order to implement efficient luminescence. For example, the organic compound can have an electron donor moiety and an electron acceptor moiety. The electron donor moiety can include, but are not limited to, a phenyl moiety, a carbazolyl moiety, an acridinyl moiety, a phenazinyl moiety, a phenoxazinyl moiety, a dibenzofuranyl moiety and/or a dibenozothiophenyl moiety, each of which is unsubstituted or substituted with cyano group, nitro group, halogen, $C_1$~$C_{10}$ alkyl group. $C_1$~$C_{10}$ alkyl halide, $C_5$~$C_{30}$ aryl group or $C_4$~$C_{30}$ hetero aryl group. The electron acceptor moiety can include, but are not limited to, an azine moiety or a pyridyl moiety, each of which is unsubstituted or substituted with cyano group, nitro group, halogen. $C_1$~$C_{10}$ alkyl group. $C_1$~$C_{10}$ alkyl halide, $C_5$~$C_{30}$ aryl group or $C_4$~$C_{30}$ hetero aryl group. As an example, the organic compound having the delayed fluorescent property can include an organic compound having the following structure of Chemical Formula 2:

Chemical Formula 2

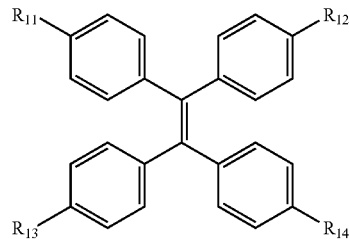

In Chemical Formula 2, each of $R_{11}$ to $R_{14}$ is independently protium, deuterium, tritium or aryl or hetero aryl group selected from the group consisting of phenyl, pyridyl, carbazolyl, acridinyl, phenazinyl, phenoxazinyl, dibenzofuranyl, dibenzothiophenyl, diazinyl and triazinyl, each of which is unsubstituted or substituted with cyano group, nitro group, halogen, $C_1$~$C_{10}$ alkyl group. $C_1$~$C_{10}$ alkyl halide group, $C_5$~$C_{30}$ aryl group or $C_4$~$C_{30}$ hetero aryl group. At least two of $R_{11}$ to $R_{14}$ is the aryl or hetero aryl group. At least one of $R_{11}$ to $R_{14}$ is pyridyl, diazinyl or triazinyl and other of $R_1$ to $R_{14}$ is phenyl, carbazolyl, acridinyl, phenazinyl, phenoxazinyl, dibenzofuranyl or dibenzothiophenyl. Each of $R_{11}$ to $R_{14}$ is independently linked to the phenylene ring directly or via $C_5$~$C_{30}$ arylene group or $C_4$~$C_{30}$ hetero arylene group.

In one exemplary embodiment, each of $R_{11}$ to $R_{14}$ can independently be any one of the following aromatic substituents:

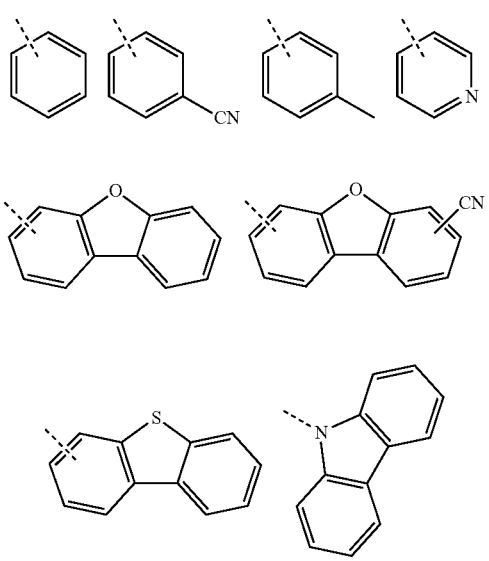

17
-continued
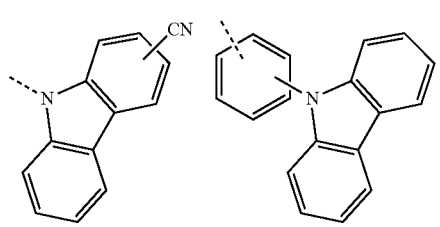
18
-continued
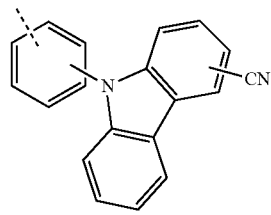
Particularly, the organic compound can be any one having the following structure of Chemical Formula 3.
Chemical Formula 3
Compound 1
Compound 2
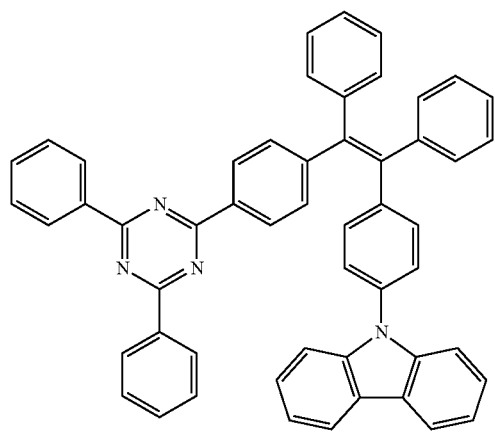
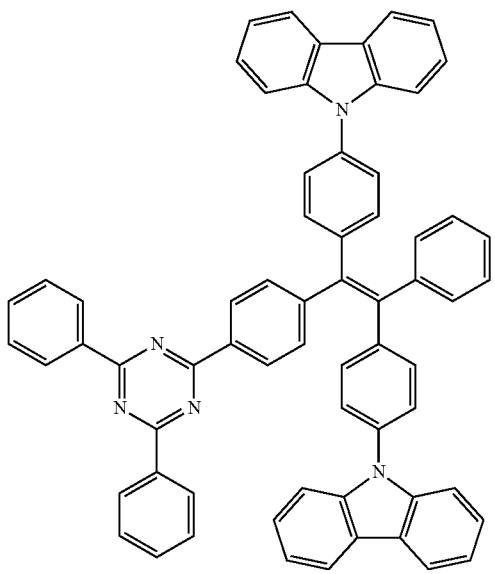
Compound 3
Compound 4
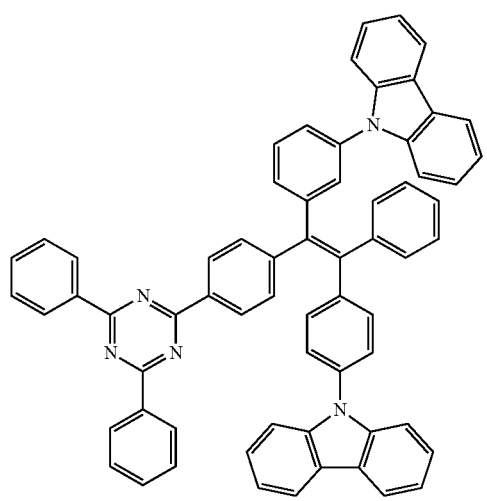
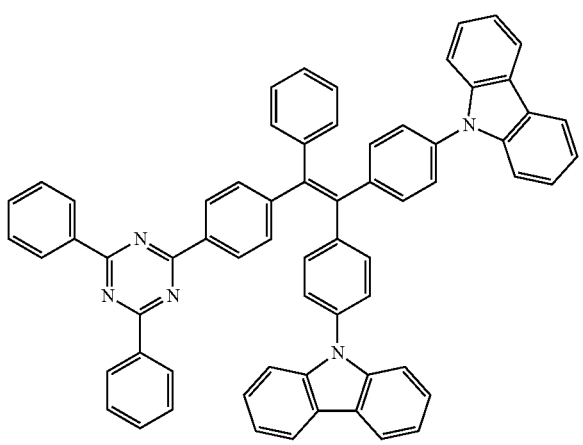

Compound 5
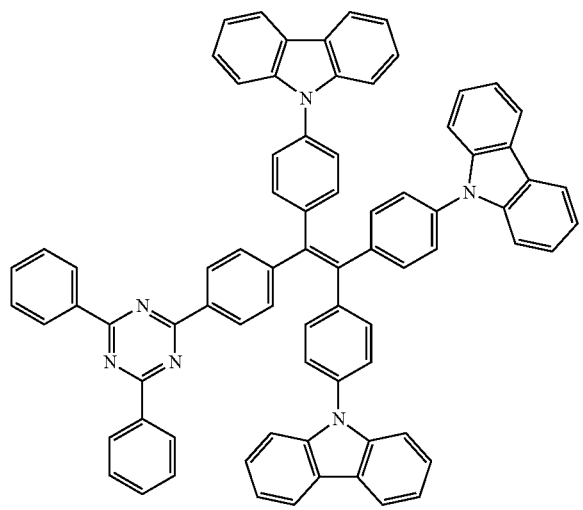
Compound 6
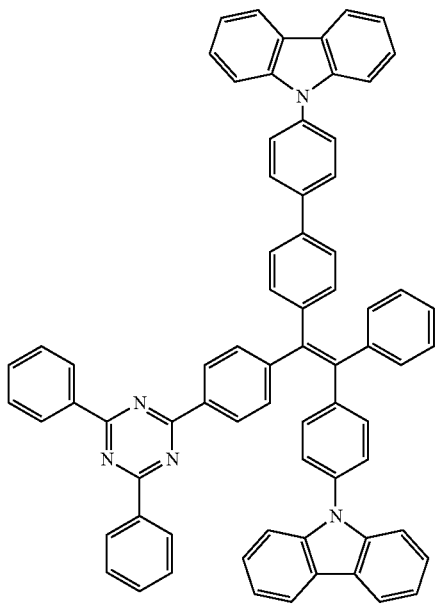
Compound 7
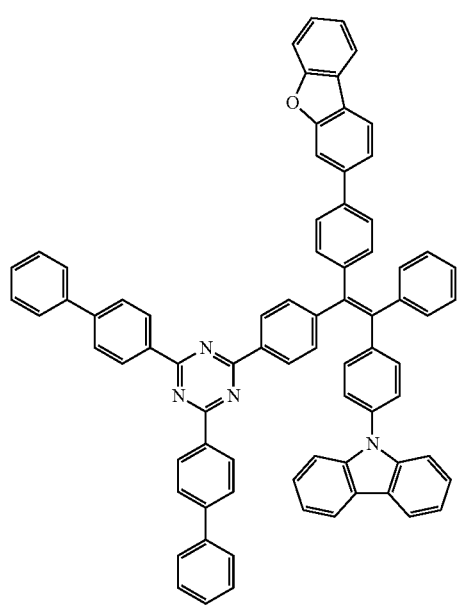
Compound 8
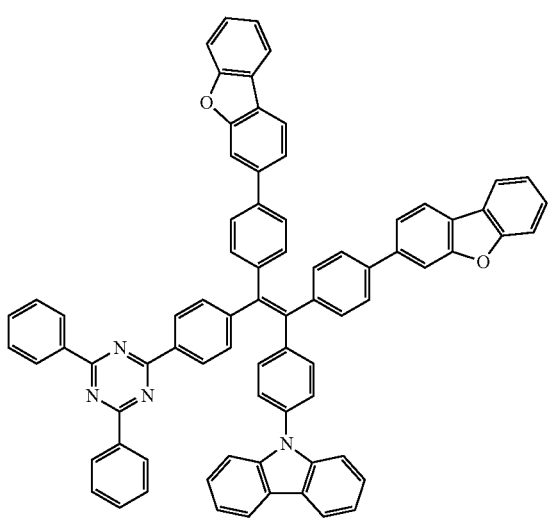

-continued
Compound 9
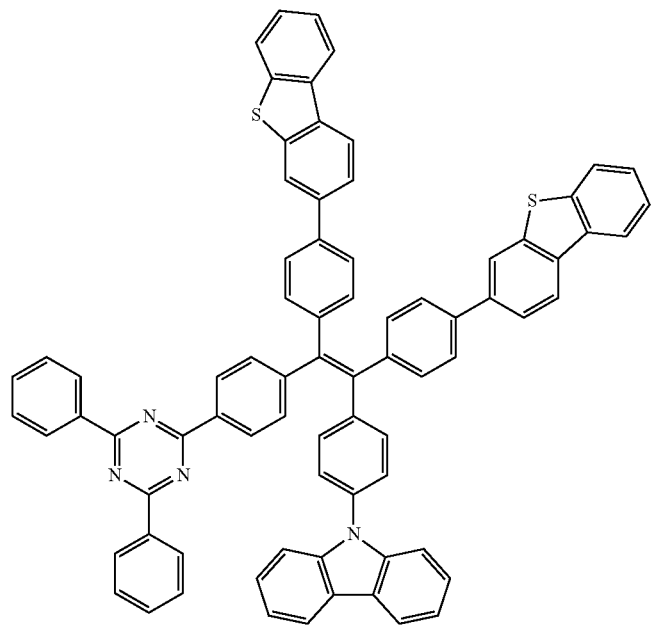
Compound 10
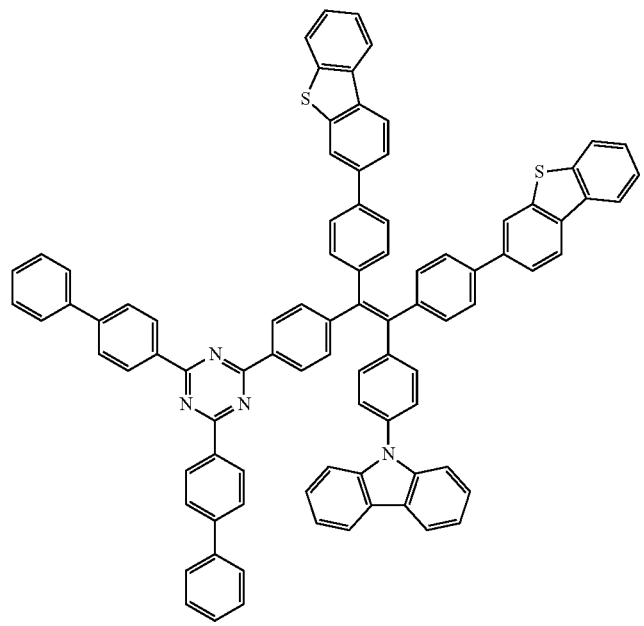

Compound 11

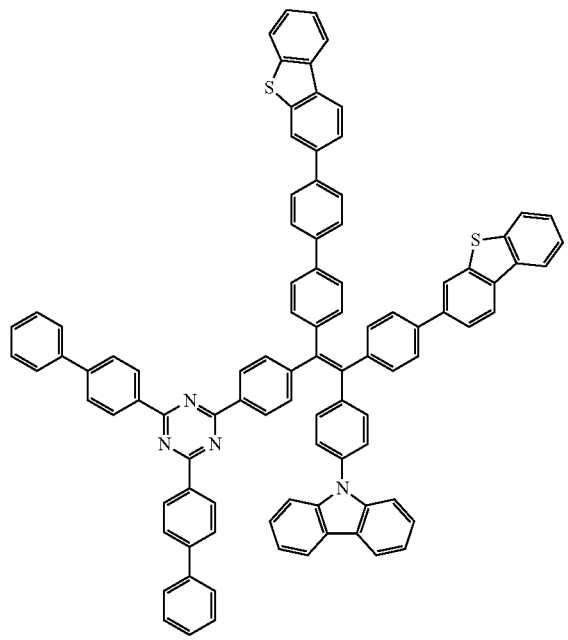

Compound 12

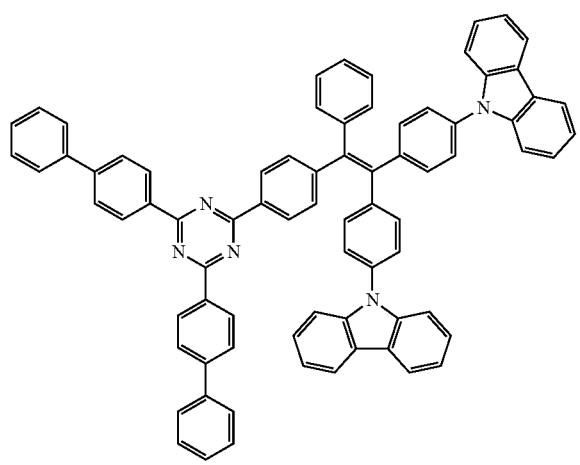

Compound 13

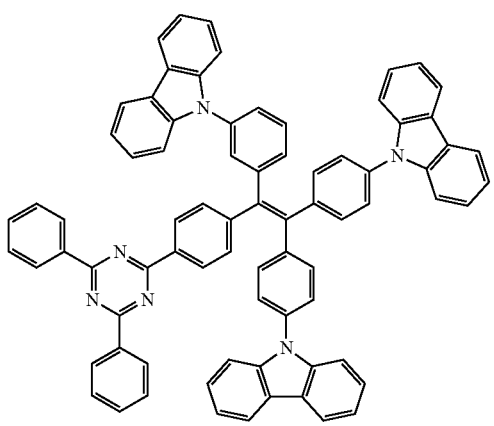

The host is not limited to specific material only if each of the excited state singlet energy level $S_1^H$ and the excited state triplet energy level $T_1^H$ of the host is higher than each of the excited state singlet energy levels $S_1^{TD}$ and $S_1^{ED}$ and the excited state triplet energy levels $T_1^{TD}$ and $T_1^{ED}$ of the dopant and the organic compound, respectively.

As an example, the host in the EML1 362 can include, but are not limited to, 9-(3-(9H-carbazol-9-yl)phenyl)-9H-carbazole-3-carbonitrile (mCP-CN), CBP, mCBP, mCP, DPEPO, 2,8-bis(diphenylphosphoryl)dibenzothiophene (PPT), 1,3,5-tri[(3-pyridyl)-phen-3-yl]benzene (TmPyPB), 2,6-di(9H-carbazol-9-yl)pyridine (PYD-2Cz), 2,8-di(9H-carbazol-9-yl)dibenzothiophene (DCzDBT), 3',5'-Di(carbazol-9-yl)-[1,1'-biphenyl]-3,5-dicarbonitrile (DCzTPA), 4'-(9H-carbazol-9-yl)biphenyl-3,5-dicarbonitrile (pCzB-2CN), 3'-(9H-carbazol-9-yl)biphenyl-3,5-dicarbonitrile (mCzB-2CN), TSPO1, 9-(9-phenyl-9H-carbazol-6-yl)-9H-carbazole (CCP), 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole.

In addition, the dopant is not limited to specific material only if the dopant can received singlet and triplet exciton energies from the host and has a delayed fluorescent property. As an example, the first dopant can be the same as the organic compound. In this case, both the EML1 362 and the EEL 390 can emit light having the same luminescence wavelength.

In another exemplary embodiment, the dopant can be a delayed fluorescent material different from the organic compound. In this case, the dopant can emit light having substantially the same luminescence wavelength as the first organic compound or emit light having different luminescence wavelength from the organic compound. As an example, the dopant can be a delayed fluorescent material having an electron donor moiety and an electron acceptor moiety.

As an example, a delayed fluorescent material, which can be used as the dopant in the EML1 362, can include any one having the following structure of Chemical Formula 4.
Chemical Formula 4
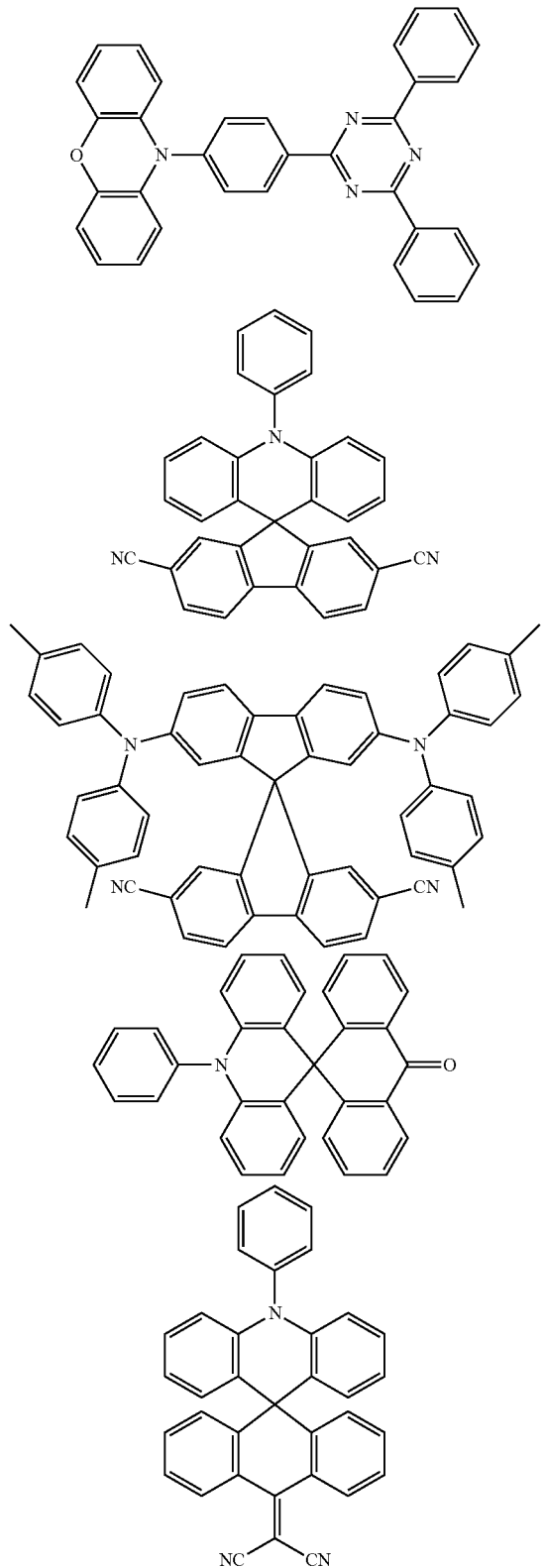
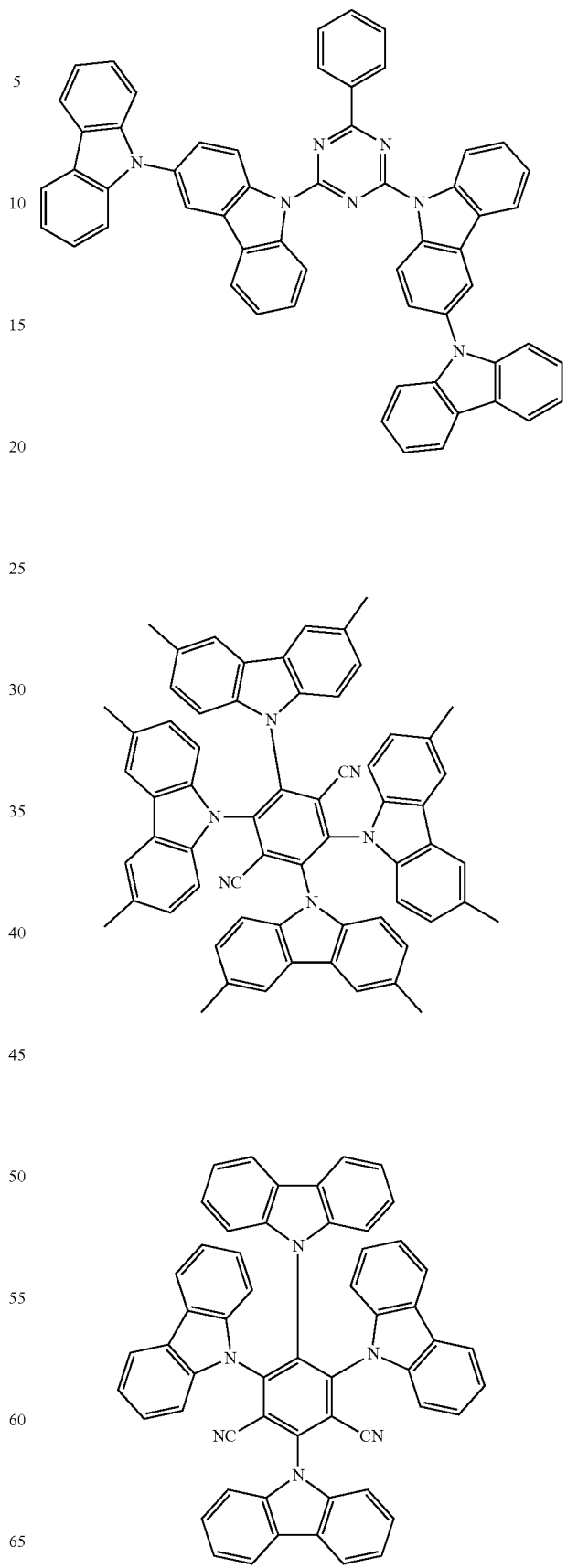

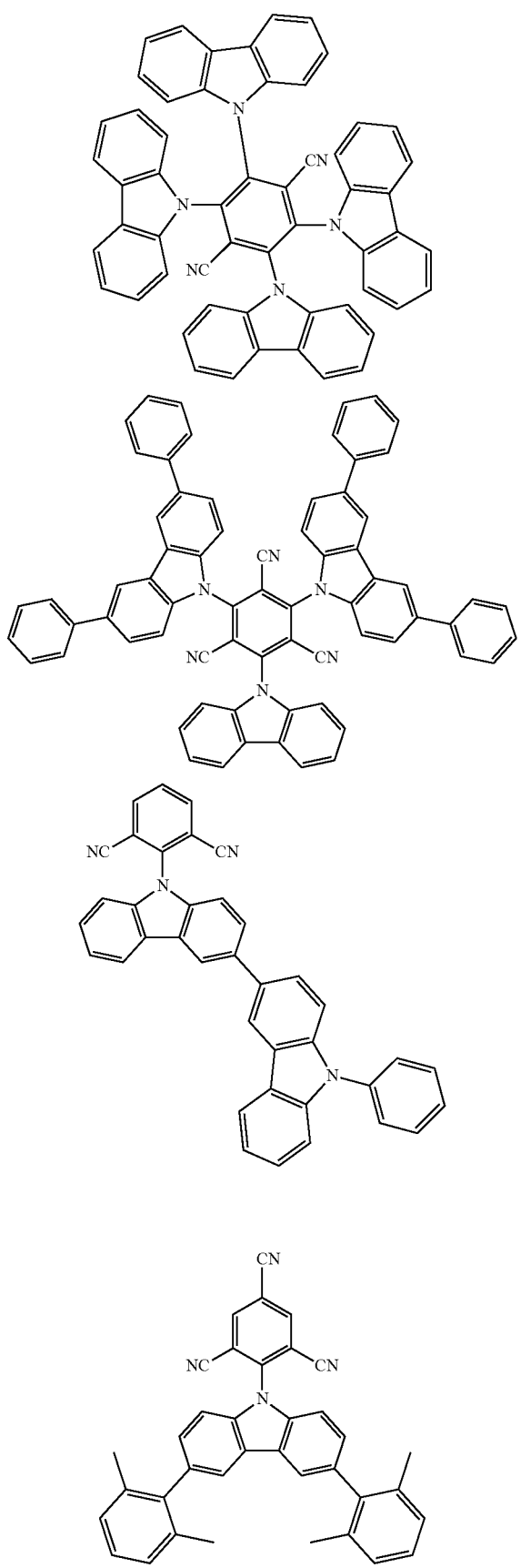
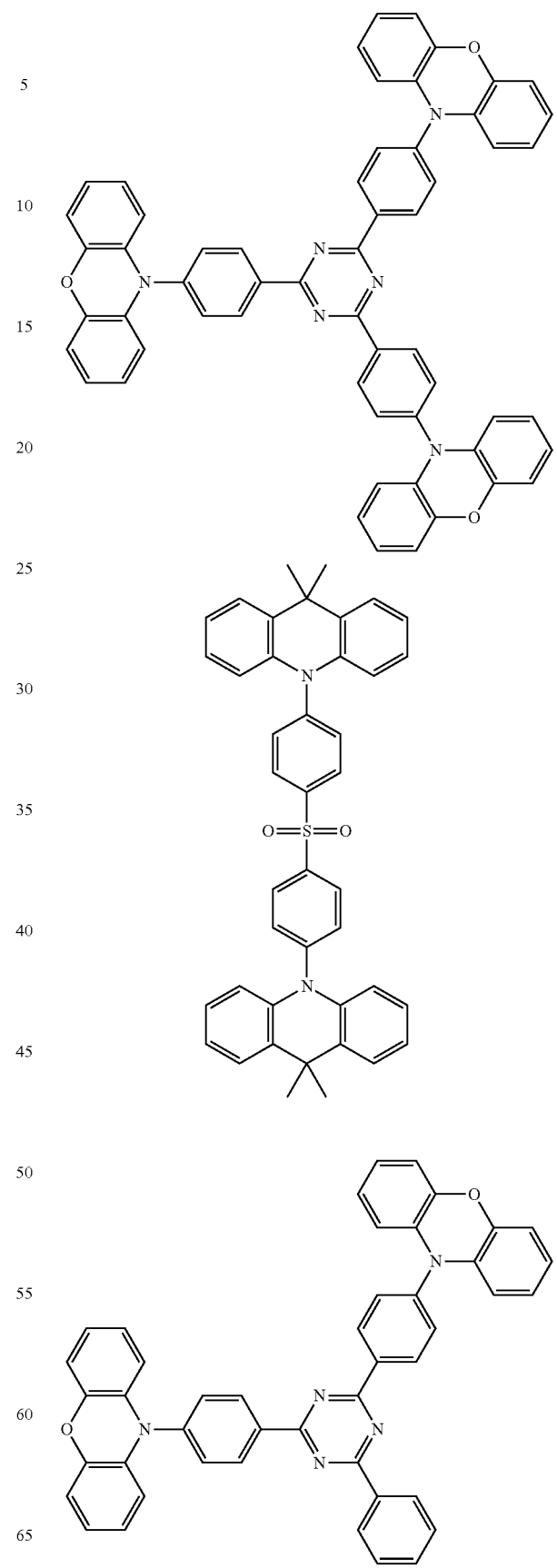

29
-continued
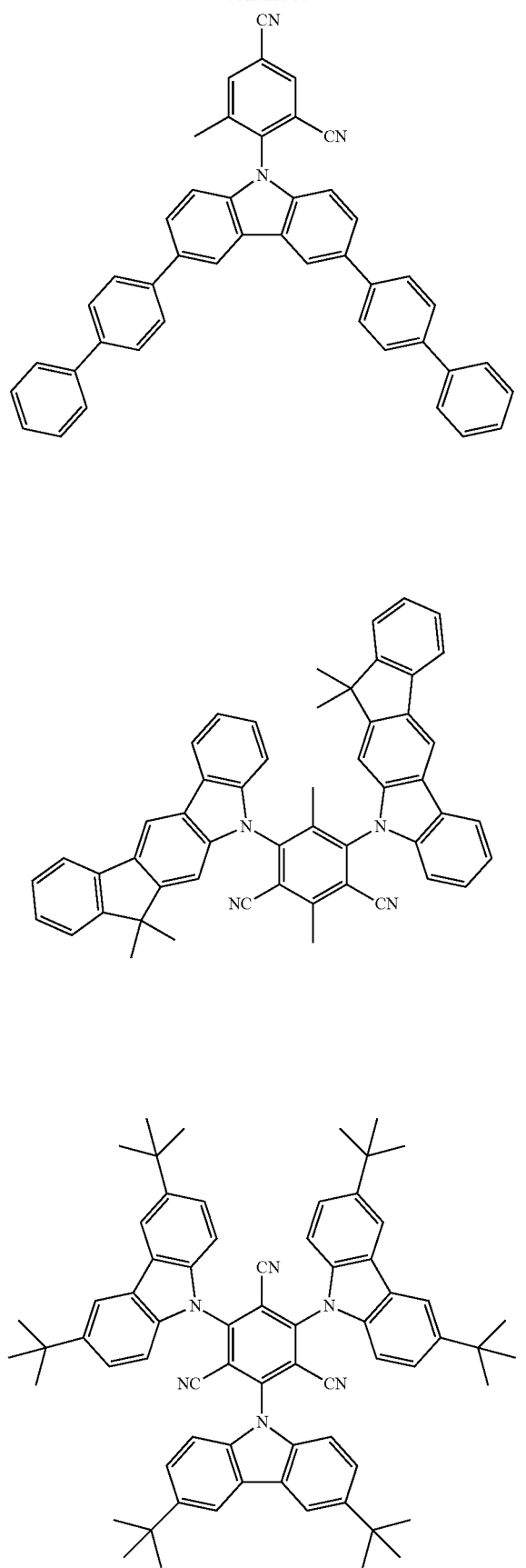
30
-continued
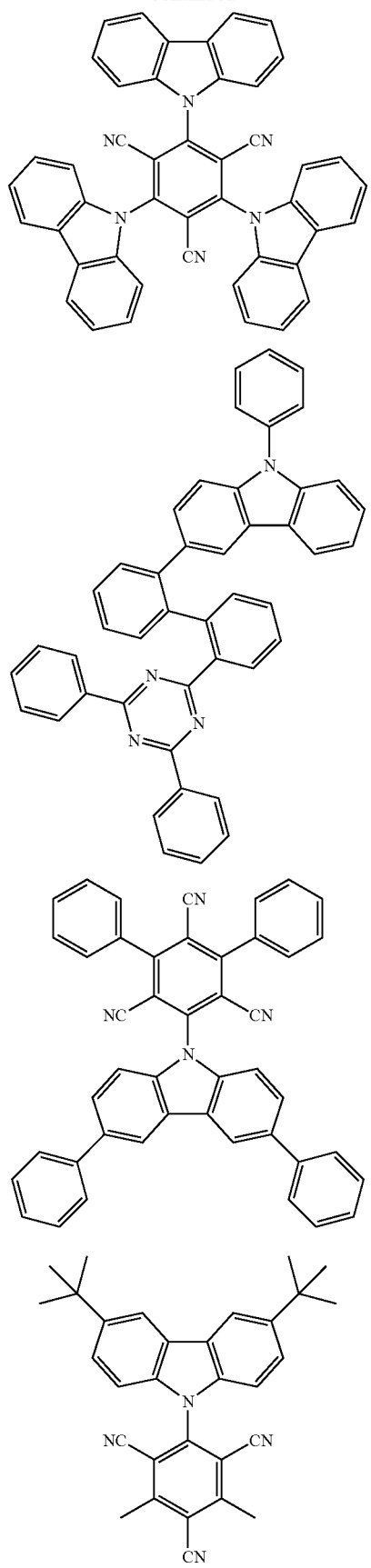

31
-continued
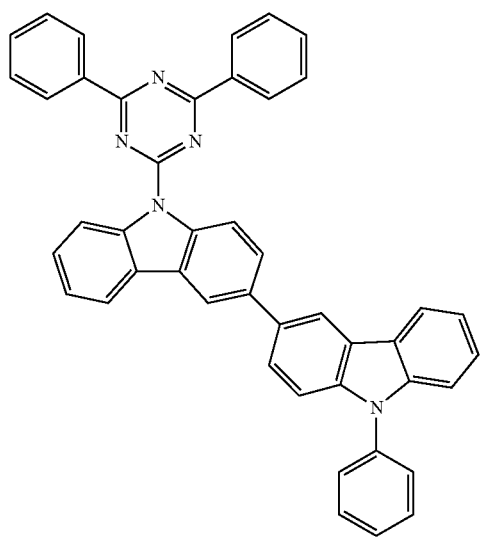
32
-continued
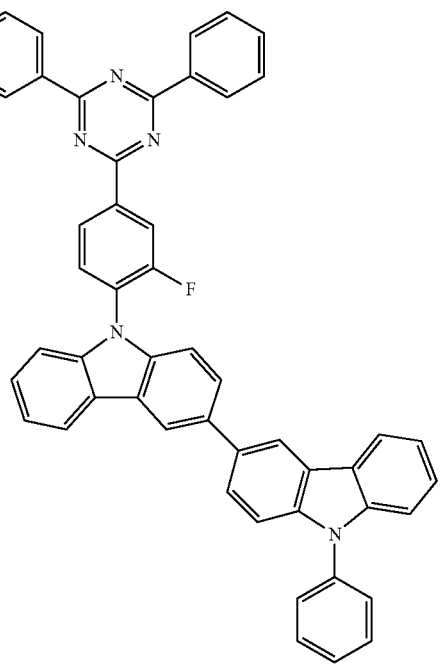
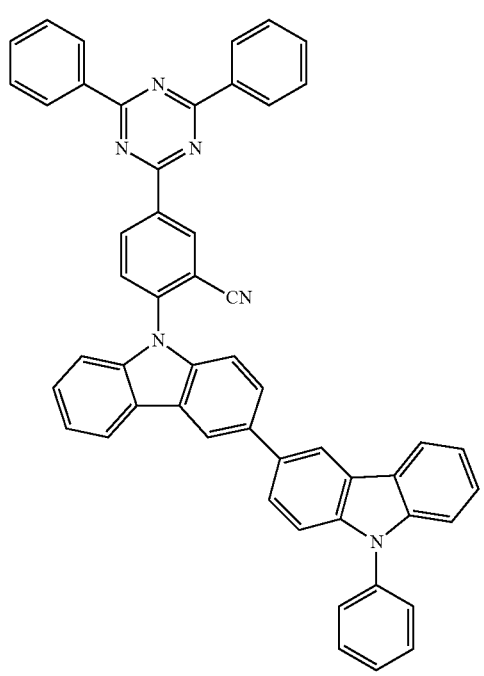

33
-continued
34
-continued
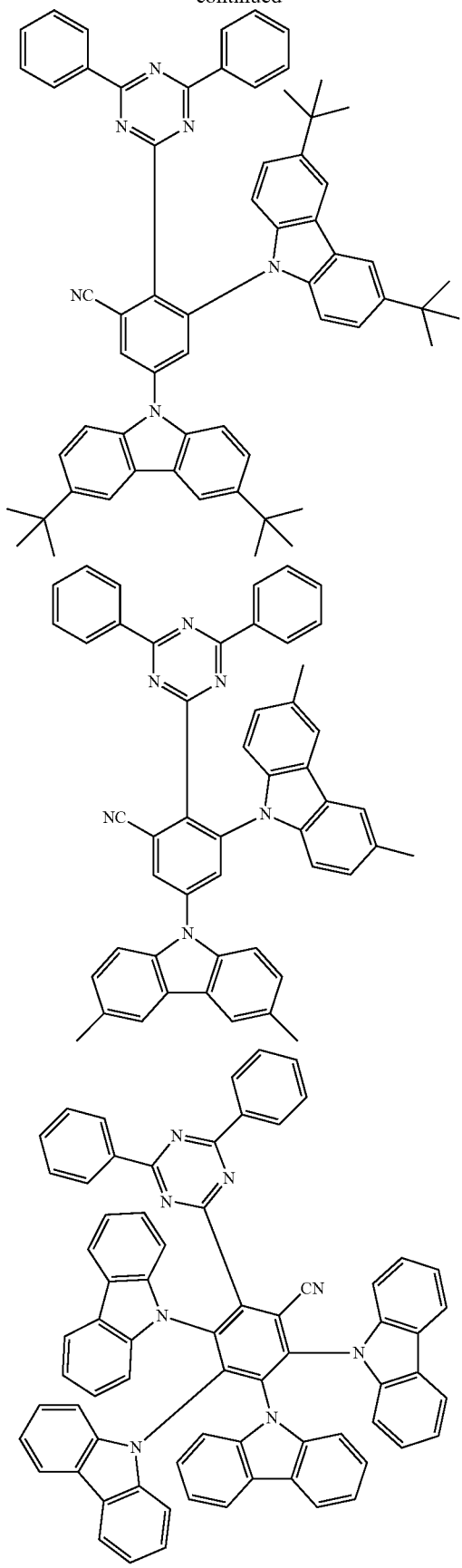
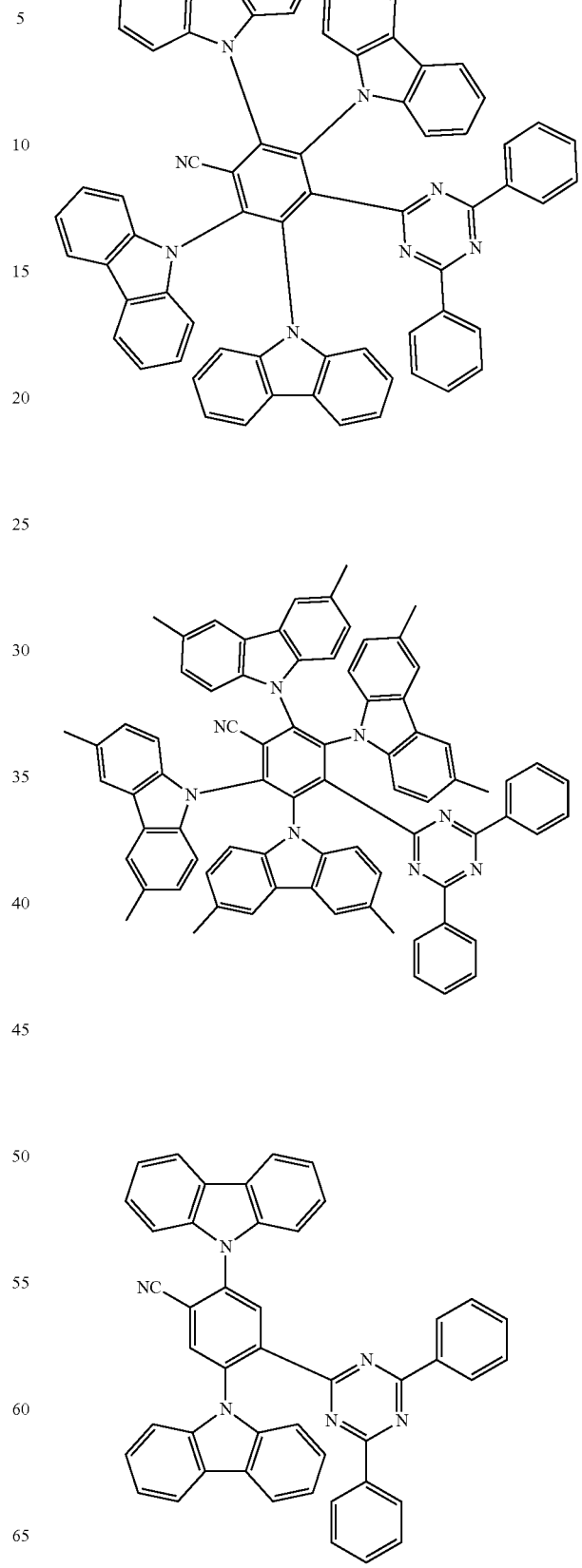

35
-continued
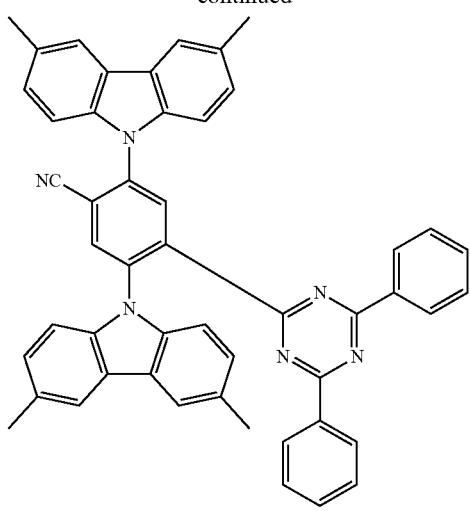
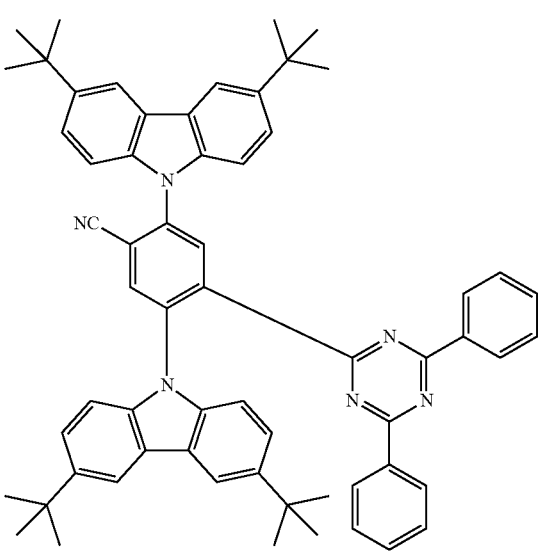
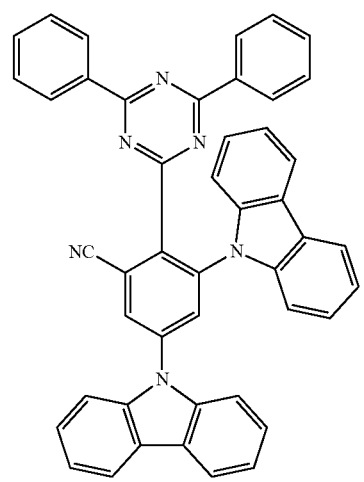
36
-continued
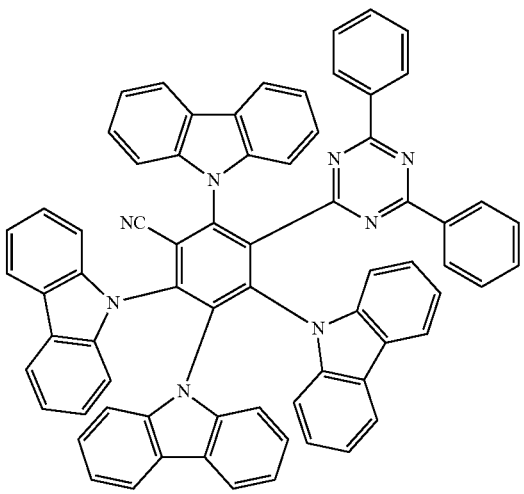
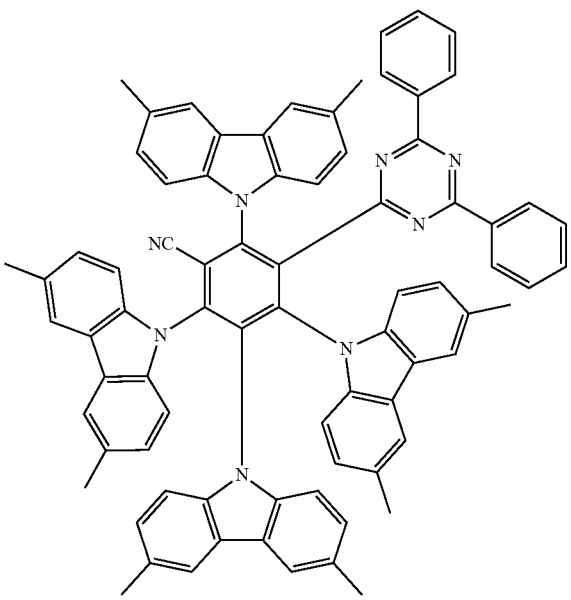
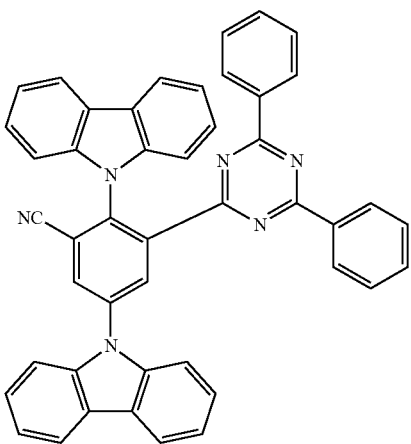

37
-continued
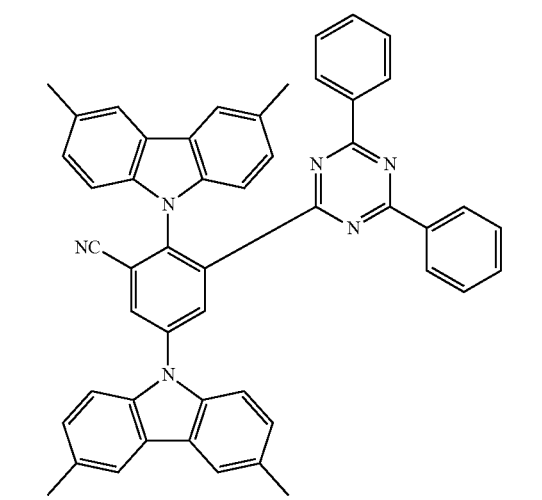
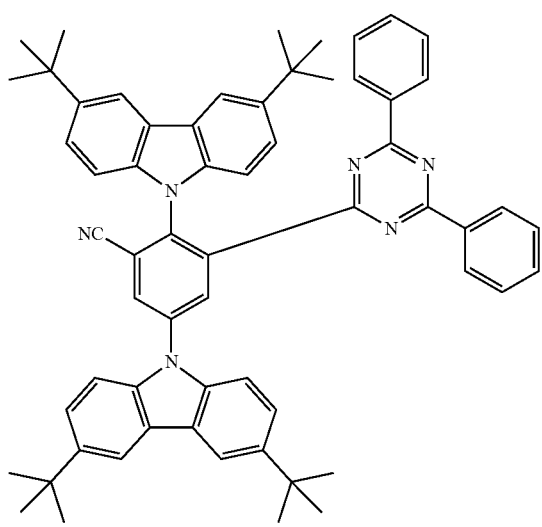
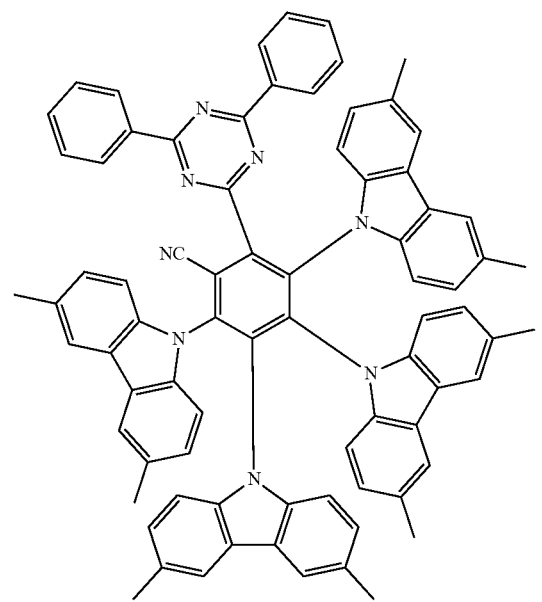
38
-continued
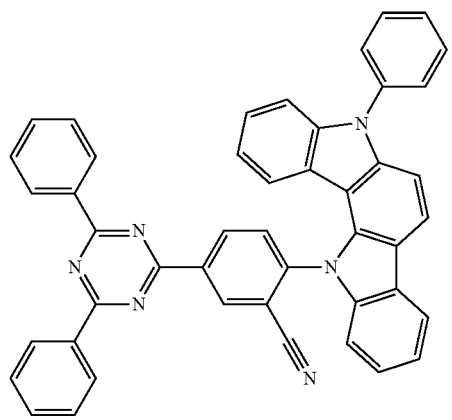
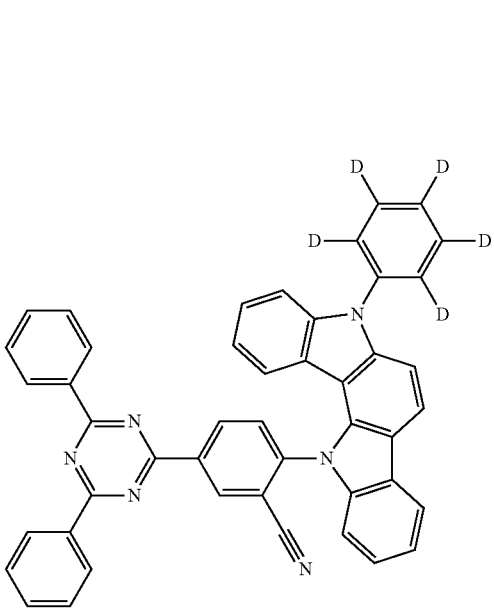

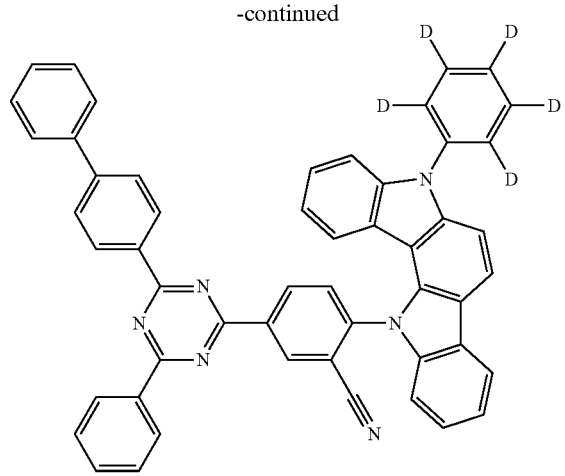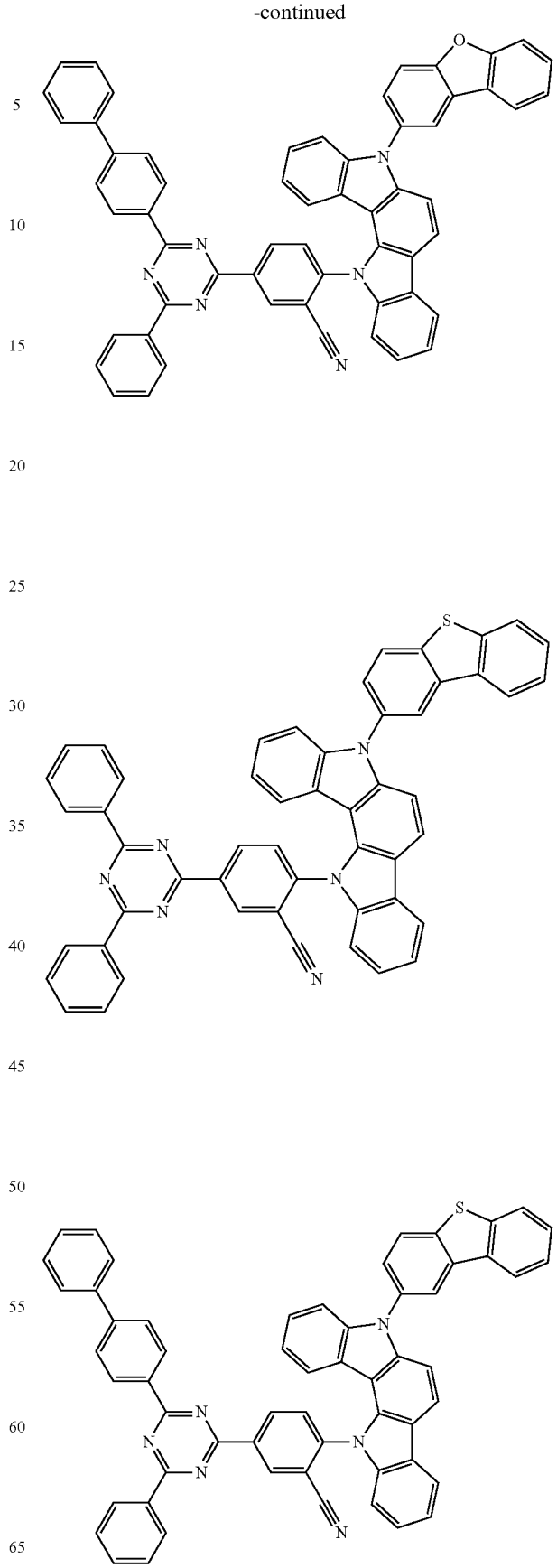

-continued

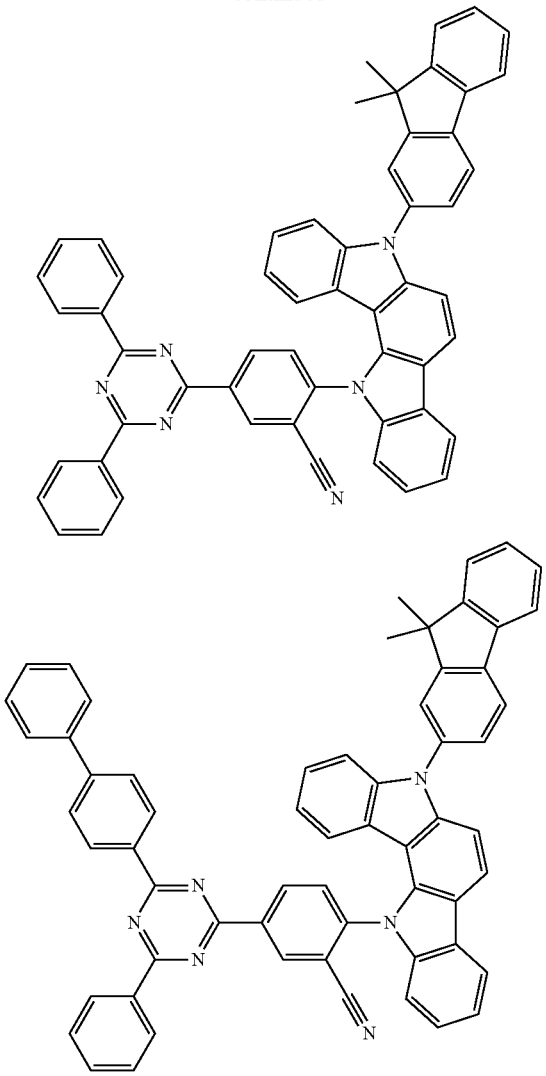

In another exemplary embodiment, the dopant in the EML1 362 can include, but are not limited to, 10-(4-(4,6-diphenyl-1,3,5-triazin-2-yl)phenyl)-9,9-dimethyl-9,10-dihydroacridine (DMAC-TRZ), 10,10'-(4,4'-sulfonylbis(4,1-phenylene))bis(9,9-dimethyl-9,10-dihydroacridine) (DMAC-DPS), 10-phenyl-10H,10'H-spiro[acridine-9,9-anthracen]-10'-one (ACRSA), 3,6-dibenzoyl-4,5-di(1-methyl-9-phenyl-9H-carbazoyl)-2-ethynylbenzonitrile (Cz-VPN), 9,9',9'''-(5-(4,6-diphenyl-1,3,5-triazin-2-yl)benzene-1,2,3-triyl) tris(9H-carbazole) (TcZTrz), 9,9'-(5-(4,6-diphenyl-1,3,5-triazin-2-yl)-1,3-phenylene)bis(9H-carbazole) (DczTrz), 9,9',9'',9'''-((6-phenyl-1,3,5-triazin-2,4-diyl))bis(benzene-5,3,1-triyl))tetrakis(9H-carbazole) (DDczTrz), bis(4-(9H-3,9'-bicarbazol-9-yl)phenyl)methanone (CC2BP), 9'-[4-(4,6-diphenyl-1,3,5-triazin-2-yl)phenyl]-3,3'',6,6''-tetraphenyl-9,3:6',9''-ter-9H-carbazole (BDPCC-TPTA), 9'-[4-(4,6-diphenyl-1,3,5-triazin-2-yl)phenyl]-9,3':6',9''-ter-9H-carbazole (BCC-TPTA), 9,9'-(4,4'-sulfonylbis(4,1-phenylene))bis(3,6-dimethoxy-9H-carbazole) (DMOC-DPS), 9-(4-(4,6-diphenyl-1,3,5-triazin-2-yl)phenyl)-3',6'-diphenyl-9H-3,9'-bicarbazole (DPCC-TPTA), 10-(4,6-diphenyl-1,3,5-triazin-2-yl)-10H-phenoxazine (Phen-TRZ), 9-(4-(4,6-diphenyl-1,3,5-triazin-2-yl)phenyl)-9H-carbazole (Cab-Ph-TRZ), 1,2,3,5-Tetrakis(3,6-carbazol-9-yl)-4,6-dicyanobenzene (4CzIPN), 2,3,4,6-tetra(9H-carbazol-9-yl)-5-fluorobenzonitrile (4CZFCN), 10-(4-(4,6-diphenyl-1,3,5-triazin-2-yl)phenyl)-10H-spiro[acridine-9,9'-xanthene] and/or 10-(4-(4,6-diphenyl-1,3,5-triazin-2-yl)phenyl)-10H-spiro[acridine-9,9'-fluorene] (SpiroAC-TRZ).

When the EML1 362 includes the host and the dopant, the EML1 362 can include the dopant of about 1 to about 70% by weight, preferably about 10 to about 50% by weight, and preferably about 20 to about 50% by weight. As an example, the EML1 362 can be laminated with a thickness of, but not limited to, about 20 nm to about 100 nm, and preferably about 20 nm to about 50 nm.

Figure 6:
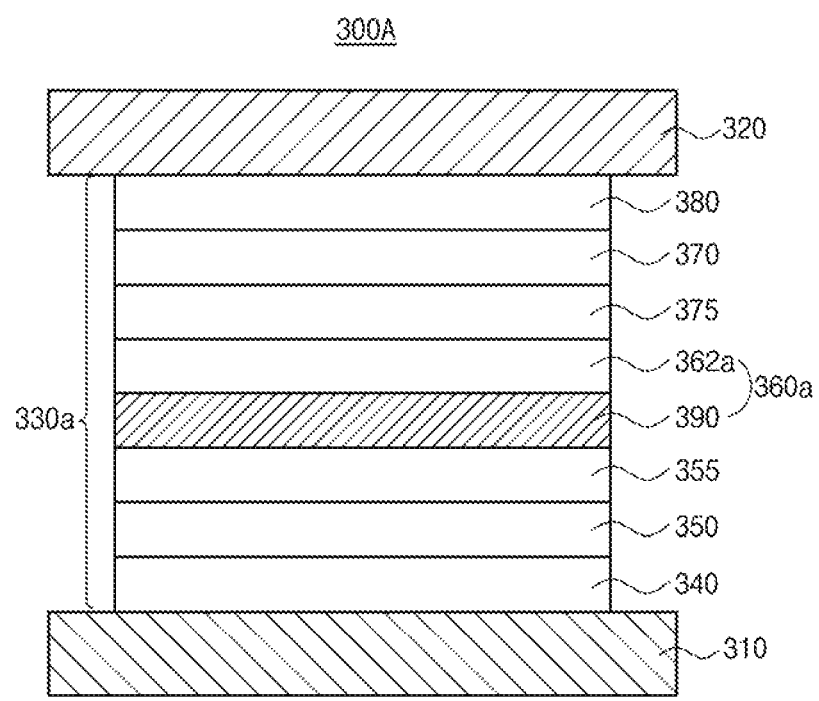
FIG. 6 is a schematic cross-sectional view illustrating an organic light emitting diode in accordance with another exemplary embodiment of the present disclosure.

In the above first embodiment, the EML1 362 includes only one dopant having the delayed fluorescent property, and the EEL 390 includes the organic compound. Unlike that embodiment, the EML1 can include plural dopant having different luminous properties. FIG. 6 is a schematic cross-sectional view illustrating an organic light emitting diode in accordance with another exemplary embodiment of the present disclosure. As illustrated in FIG. 6, the organic light emitting diode (OLED) 300A in accordance with the second embodiment of the present disclosure includes first and second electrodes 310 and 320 facing each other and an emitting unit 330a disposed between the first and second electrode 310 and 320.

In one exemplary embodiment, the emitting unit 330a as an emission layer includes a HIL 340, a HTL 350, an EML 360a, an ETL 370 and an EIL 380 each of which is laminated sequentially over the first electrode 310. The emitting unit 330a can further includes an EBL 355 disposed between the HTL 350 and the EML 360a and/or a HBL 375 disposed between the EML 360a and the ETL 370. The emitting unit 330a in the OLED 300A can have substantially the same structure and the same material as the emitting unit 330 in the first embodiment.

The EML 360a includes a first EML (EML1) 362a and an exciton energy control layer (EEL) 390 disposed adjacently to the EML1 362a. The EML1 362a includes a host, a first dopant and a second dopant. As an example, a delayed fluorescent material can be used as the first dopant (T dopant) and a fluorescent or phosphorescent material can be used as the second dopant (F dopant). The EEL 390 can include an organic compound having the structure of any one in Chemical Formulae 1 to 3. Alternatively, the first dopant can be the same as the organic compound.

When an EML includes only the dopant which has the delayed fluorescent property, the EML can implement high internal quantum efficiency as the related art phosphorescent materials including heavy metals because the dopant can exhibit 100% internal quantum efficiency in theory. However, because of the bond formation between the electron acceptor and the electron donor and sterical twists within the delayed fluorescent material, additional charge transfer transition (CT transition) within the delayed fluorescent material is caused thereby, and the delayed fluorescent material have various geometry. As a result, the delayed fluorescent materials show emission spectra having very broad FWHM (full-width at half maximum) in the course of emission, which results in poor color purity. In addition, the delayed fluorescent material utilizes the triplet exciton energy as well as the singlet exciton energy in the luminous process with rotating each moiety within its molecular structure, which results in twisted internal charge transfer (TICT). As a result, the luminous lifetime of an OLED including only the delayed fluorescent materials can be reduced owing to weakening of molecular bonding forces among the delayed fluorescent materials.

In the second embodiment, the EML1 362a further includes the second dopant, which can be a fluorescent or phosphorescent material, in order to prevent the color purity and luminous lifetime from being reduced in case of using only the delayed fluorescent materials. The triplet exciton energies of the first dopant (T dopant) and the organic compound, each of which can be the delayed fluorescent material, is converted to the singlet exciton energy of its own by RISC mechanism, then each of the converted singlet exciton energy of the first dopant and organic compound can be transferred to the second dopant (F dopant), which can be the fluorescent or phosphorescent material, in the EML1 362a by Dexter energy transfer mechanism and by FRET energy transfer mechanism.

Figure 7:
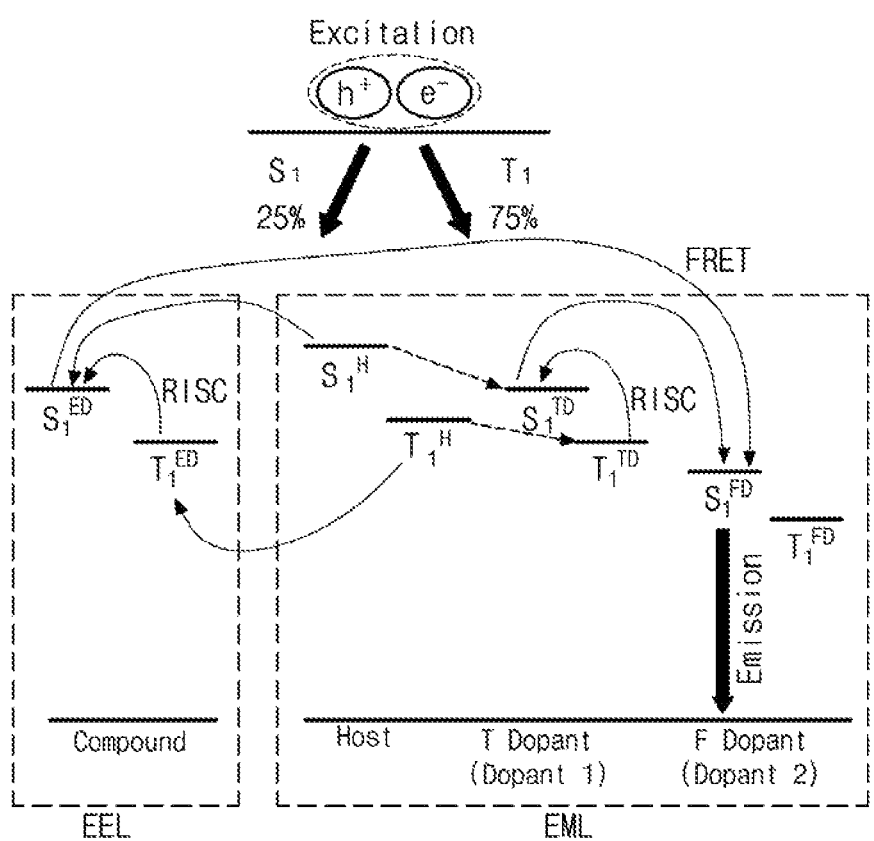
FIG. 7 is a schematic diagram illustrating luminous mechanism by energy level bandgap among luminous materials in accordance with another exemplary embodiment of the present disclosure.

When the EML1 362a includes the host, the first dopant (T dopant) having the delayed fluorescent property and the second dopant (F dopant) which is a fluorescent or phosphorescent material, it is necessary to adjust properly energy levels amount those luminous materials including the organic compound. FIG. 7 is a schematic diagram illustrating luminous mechanism by energy level bandgap among luminous materials in accordance with another exemplary embodiment of the present disclosure. Each energy level bandgap between excited state singlet energy levels $S_1^{TD}$ and $S_1^{ED}$ and an excited state triplet energy level $T_1^{TD}$ and $T_1^{ED}$ of the first dopant (T dopant) and the organic compound can be equal to or less than about 0.3 eV in order to realize the delayed fluorescence.

Each of an excited state singlet energy level $S_1^H$ and an excited state triplet energy level $T_1^H$ of the host should be higher than each of the excited state singlet energy levels $S_1^{TD}$ and $S1^{ED}$ and the excited state triplet energy levels $T_1^{TD}$ and $T_1^{ED}$ of the first dopant and the organic compound, respectively. As an example, the excited state triplet energy level $T_1^H$ of the host can be higher than each of the excited state triplet energy levels $T_1^{TD}$ and $T_1^{ED}$ of the first dopant and the organic compound by at least about 0.2 eV. In addition, each of the excited state triplet energy levels $T_1^{TD}$ and $T_1^{ED}$ of the first dopant and the organic compound is higher than an excited state triplet energy level $T_1^{FD}$ of the second dopant. In an alternative embodiment, each of the excited state singlet energy levels $S_1^{TD}$ and $S_1^{ED}$ of the first dopant and the organic compound can be higher than an excited state singlet energy level $S_1^{FD}$ of the second dopant as the fluorescent material.

In addition, an energy level bandgap ($|HOMO^H-HOMO^{TD}|$) between a HOMO energy level ($HOMO^H$) of the host and a HOMO energy level ($HOMO^{TD}$) of the first dopant, or an energy level bandgap ($|LUMO^H-LUMO^{TD}|$) between a LUMO energy level ($LUMO^H$) of the host and a LUMO energy level ($LUMO^{TD}$) of the first dopant can be equal to or less than about 0.5 eV. Moreover, an energy level bandgap ($|HOMO^H-HOMO^{ED}|$) between a HOMO energy level ($HOMO^H$) of the host and a HOMO energy level ($HOMO^{ED}$) of the organic compound, or an energy level bandgap ($|LUMO^H-LUMO^{ED}|$) between a LUMO energy level ($LUMO^H$) of the host and a LUMO energy level ($LUMO^{ED}$) of the organic compound can be equal to or less than about 0.2 eV.

The exciton energy should be transferred from the first dopant and the organic compound as the delayed fluorescent material to the second dopant as the fluorescent or phosphorescent material in order to realize hyper-fluorescence. With regard to energy transfer efficiency from the delayed fluorescent material to the fluorescent or phosphorescent material, an overlap between an emission spectrum of the delayed fluorescent material and an absorption spectrum of the fluorescent or phosphorescent material can be considered. As an example, a fluorescent or phosphorescent material having an absorption spectrum in a wide overlapping area with respect to an emission spectrum of the first dopant and the organic compound as the delayed fluorescent material can be used as the second dopant.

The organic compound in the EEL 390 can include, but are not limited to, any compound having the structure of Chemical Formulae 1 to 3, as described above. The host in the EML1 362a can include, but are not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

In one exemplary embodiment, the first dopant can be the same as the organic compound. In another exemplary embodiment, the first dopant can include, but are not limited to, any one having the structure of Chemical Formula 4. In still another exemplary embodiment, the first dopant can include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9, 9'-xanthene] and/or SpiroAC-TRZ.

In one exemplary embodiment, the fluorescent material as the second dopant can have, but are not limited to, quinolino-acridine core. As an example, the second dopant having the quinolino-acridine core can include 5,12-dimethylquinolino[2,3-b]acridine-7,14(5H, 12H)-dione ($S_1$: 2.3 eV; $T_1$: 2.0 eV; LUMO: −3.0 eV; HOMO: −5.4 eV), 5,12-diethylquinolino[2,3-b]acridine-7,14(5H, 12H)-dione ($S_1$: 2.3 eV; $T_1$: 2.2 eV; LUMO: −3.0 eV; HOMO: −5.4 eV), 5,12-dibutyl-3,10-difluoroquinolino[2,3-b]acridine-7,14(5H, 12H)-dione ($S_1$: 2.2 eV; $T_1$: 2.0 eV; LUMO: −3.1 eV; HOMO: −5.5 eV), 5,12-dibutyl-3,10-bis(trifluoromethyl)quinolino[2,3-b]acridine-7,14(5H, 12H)-dione ($S_1$: 2.2 eV; $T_1$: 2.0 eV; LUMO: −3.1 eV; HOMO: −5.5 eV), 5,12-dibutyl-2,3,9,10-tetrafluoroquinolino[2,3-b]acridine-7,14 (5H, 12H)-dione ($S_1$: 2.0 eV; $T_1$: 1.8 eV; LUMO: −3.3 eV; HOMO: −5.5 eV).

In addition, the fluorescent material as the second dopant can include, but are not limited to, 1,1,7,7-tetramethyl-2,3,6,7-tetrahydro-1H,5H-benzo[ij]quinolizin-9-yl)ethenyl]-4H-pyran-4-ylidene}propanedinitrile (DCJTB; $S_1$: 2.3 eV; $T_1$: 1.9 eV; LUMO: −3.1 eV; HOMO: −5.3 eV). Moreover, metal complexes which can emit light of red, green or blue color can be used as the second dopant.

In one exemplary embodiment, the weight ratio of the host can be larger than the weight ratio of the first and second dopants in the EML1 362a, and the weight ratio of the first dopant can be larger than the weight ratio of the second dopant. In an alternative embodiment, the weight ratio of the host is larger than the weight ratio of the first dopant and the weight ratio of the first dopant is larger than the weight ratio of the second dopant. When the weight ratio of the first dopant is larger than the weight ratio of the second dopant, excition energy can be transferred enough from the first dopant to the second dopant by Dexter energy transfer mechanism. As an example, the EML1 362a includes the host of about 60 to about 75% by weight, the first dopant of about 20 to about 40% by weight and the second dopant of about 0.1 to about 5% by weight.

Figure 8:
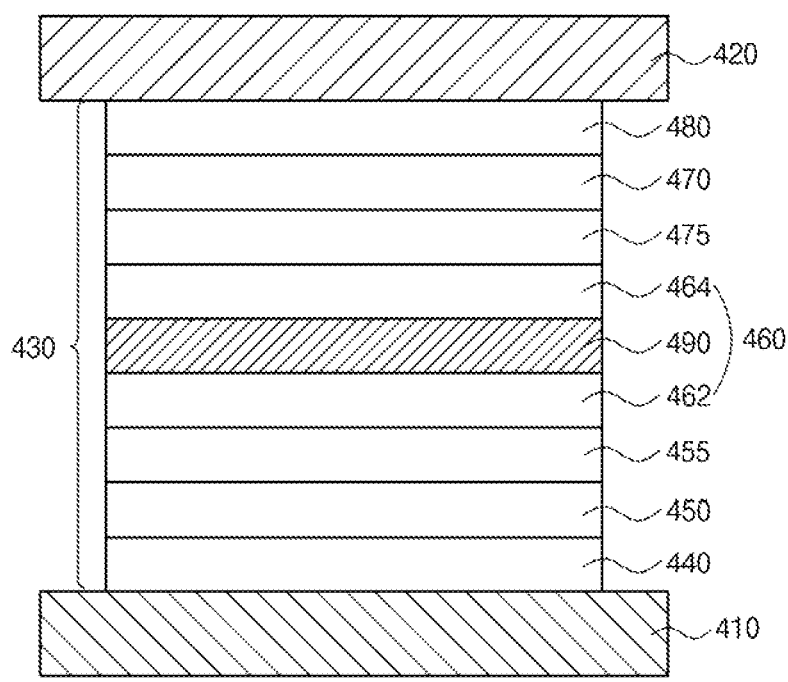
FIG. 8 is a schematic cross-sectional view illustrating an organic light emitting diode in accordance with another exemplary embodiment of the present disclosure.

In the above embodiments, an OLED includes an exciton energy control layer disposed adjacently to one emitting material layer. Unlike those embodiments, an exciton energy control layer can be disposed between two emitting material layers. FIG. 8 is a schematic cross-sectional view illustrating an organic light emitting diode in accordance with another exemplary embodiment of the present disclosure.

As illustrated in FIG. 8, the OLED 400 in accordance with the third embodiment of the present disclosure include first and second electrodes 410 and 420 facing each other and an emitting unit 430 disposed between the first and second electrodes 410 and 420. In one exemplary embodiment, the emitting unit 430 comprises a HIL 440, a HTL 450, an EML 460, an ETL 470 and an EIL 480 each of which is laminated sequentially over the first electrode 410. The emitting unit 430 can further comprise a first exciton blocking layer, i.e. an EBL 455 disposed between the HTL 450 and the EML 460 and/or a second exciton blocking layer, i.e. a HBL 475 disposed between the EML 460 and the ETL 470.

As described above, the first electrode 410 can be an anode and can include, but are not limited to, a conductive material having a relatively large work function values such as ITO, IZO, SnO, ZnO, ICO, AZO, and the like. The second electrode 420 can be a cathode and can include, but are not limited to, a conductive material having a relatively small work function values such as Al, Mg, Ca, Ag, alloy thereof or combination thereof.

The HIL 440 is disposed between the first electrode 410 and the HTL 450. The HIL 440 can include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 440 can be omitted in compliance with the structure of the OLED 400.

The HTL 450 is disposed adjacently to the EML 460 between the first electrode 410 and the EML 460. The HTL 450 can include, but are not limited to, aromatic amine compounds such as TPD, NPD(NPB), CBP, poly-TPD, TFB, TAPC, DCDPA, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 460 includes a first EML (EML1) 462, an exciton energy control layer (EEL) 490 and a second EML (EML2) 464. The EML1 462 is disposed adjacently to the EBL 455 and includes a first host and a first dopant. The EEL 490 is disposed between the EML1 462 and the HBL 475, i.e. disposed adjacently to the EML1 462 and including an organic compound (exciton dopant). The EML2 464 is disposed between the EEL 490 and the HBL 475 and includes a second host and a second dopant. In one exemplary embodiment, substantial light emission is occurred in the first dopant, the organic compound and the second dopant. In an alternative embodiment, substantial light emission is occurred in the second dopant. The configurations and energy levels among the EML 460 will be explained in more detail below.

The ETL 470 is disposed between the EML 460 and the EIL 480. In one exemplary embodiment, the ETL 470 can include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes. As an example, the ETL 470 can include, but are not limited to, $Alq_3$, PBD, spiro-PBD, Liq, TPBi, BAlq, Bphen, NBphen, BCP, TAZ, NTAZ, TpPyPB, TmPPPyTz, PFNBr, TPQ, TSPO1 and/or 2-[4-(9,10-di-2-naphthalenyl-2-anthracenyl)phenyl]-1-phenyl-1H-benzimidazole.

The EIL 480 is disposed between the second electrode 420 and the ETL 470. In one exemplary embodiment, the EIL 480 can include, but are not limited to, an alkali halide such as LiF, CsF, NaF, $BaF_2$ and the likes, and/or an organic metal compound such as lithium benzoate, sodium stearate, and the like.

The EBL 455 can include, but are not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, DCDPA, 2,8-bis(9-phenyl-9H-carbazol-3-yl)dibenzo[b,d]thiophene and/or 3,6-bis(N-carbazolyl)-N-phenyl-carbazole.

The HBL 475 can include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 475 can include a compound having a relatively low HOMO energy level compared to the emitting material in EML 460. The HBL 475 can include, but are not limited to, BCP, BAlq, $Alq_3$, PBD, spiro-PBD, Liq, B3PYMPM, DPEPO, TSPO1, 9-(6-(9H-carbazol-9-yl)pyridine-3-yl)-9H-3,9'-bicarbazole and combination thereof.

As described above, the EML 460 includes the EML1 462 including the first host and the first dopant, the EML2 464 including the second host and the second dopant and the EEL 490 disposed between the EML1 462 and the EML2 464 and including the organic compound. In one exemplary embodiment, each of the first and second dopants can be a delayed fluorescent material. In other word, the first dopant can be a first delayed fluorescent dopant (T dopant 1) and the second dopant can be a second delayed fluorescent dopant (T dopant 2). In order to realize high luminous efficiency and long luminous lifetime, it is necessary to adjust properly energy levels among luminous materials including the organic compound (exciton dopant).

Figure 9:
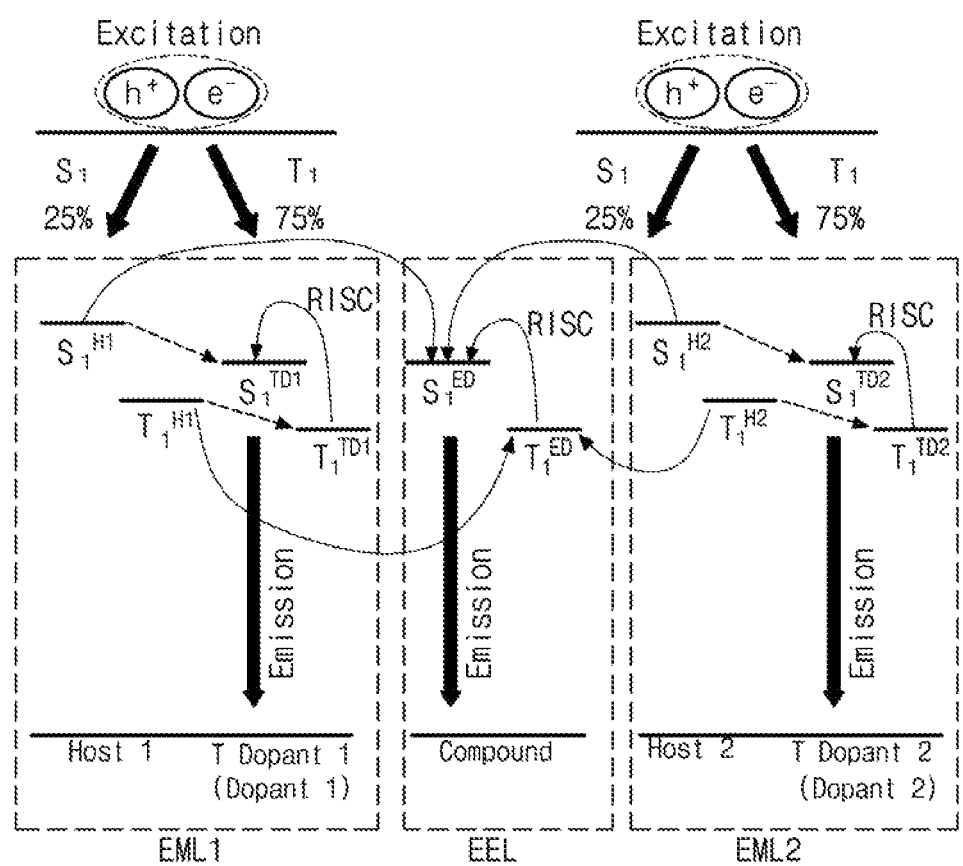
FIG. 9 is a schematic diagram illustrating luminous mechanism by energy level bandgap among luminous materials in accordance with another exemplary embodiment of the present disclosure.

FIG. 9 is a schematic diagram illustrating luminous mechanism by energy level bandgap among luminous materials in accordance with another exemplary embodiment of the present disclosure. In this embodiment, each of excited singlet energy levels $S_1^{H1}$ and $S_1^{H2}$ and excited state triplet energy levels $T_1^{H1}$ and $T_1^{H2}$ of the first and second hosts, each of which is included in the EML1 462 and the EML2 464, respectively, should be higher than each of excited state singlet energy levels $S_1^{TD1}$ and $S_1^{TD2}$ and excited state triplet energy levels $T_1^{TD1}$ and $T_1^{TD2}$ of the first and second dopants each of which has the delayed fluorescent property, respectively.

In addition, each of the excited singlet energy levels $S_1^{H1}$ and $S_1^{H2}$ and the excited state triplet energy levels $T_1^{H1}$ and $T_1^{H2}$ of the first and second hosts should be higher than each of an excited state singlet energy level $S_1^{ED}$ and an excited state triplet energy level $T_1^{ED}$ of the organic compound (exciton dopant), which has also the delayed fluorescent property, in the EEL 490, respectively. If the singlet and triplet energy levels among the hosts, the dopants and the organic compound do not satisfy the requirements above, the excitons of the singlet energy levels $S_1^{TD1}$, $S_1^{TD2}$ and $S_1^{ED}$ of the first and second dopants and the organic compound can be reversely transferred to the excited state singlet energy levels $S_1^{H1}$ and $S_1^{H2}$ of the first and second hosts, or the excitons of the triplet energy levels $T_1^{TD1}$, $T_1^{TD2}$ and $T_1^{ED}$ of the first and second dopants and the organic compound can be reversely transferred to the excited state triplet energy levels $T_1^{H1}$ and $T_1^{H2}$ of the first and second hosts. As a result, the triplet excitons of the first and second dopants and the organic compound cannot contribute to the light emission.

In addition, an energy level bandgap ($|HOMO^H-HOMO^{TD}|$) between HOMO energy levels ($HOMO^{H1}$ and $HOMO^{H2}$) of the first and second hosts and HOMO energy levels ($HOMO^{TD1}$ and $HOMO^{TD2}$) of the first and second dopants, or an energy level bandgap ($|LUMO^H-LUMO^{TD}|$) between LUMO energy levels ($LUMO^{H1}$ and $LUMO^{H2}$) of the first and second hosts and LUMO energy levels ($LUMO^{TD1}$ and $LUMO^{TD2}$) of the first and second dopants can be equal to or less than about 0.5 eV. In addition, an energy level bandgap ($|HOMO^H-HOMO^{ED}|$) between HOMO energy levels ($HOMO^{H1}$ and $HOMO^{H2}$) of the first and second hosts and a HOMO energy level ($HOMO^{ED}$) of the organic compound, or an energy level bandgap ($|LUMO^H-LUMO^{ED}|$) between LUMO energy levels ($LUMO^{H1}$ and $LUMO^{H2}$) of the first and second hosts and a LUMO energy level ($LUMO^{ED}$) of the organic compound can be equal to or less than about 0.2 eV.

Each of the exciton energies at the excited state singlet energy levels $S_1^{H1}$ and $S_1^{H2}$ and exciton energies at the excited triplet energy levels $T_1^{H1}$ and $T_1^{H2}$ of the first and second hosts, each of which is included in the EML1 462 and the EML2 464, is transferred to each of the excited state singlet energy levels $S_1^{TD1}$ and $S_1^{TD2}$ and the excited state triplet energy levels $T_1^{TD1}$ and $T_1^{TD2}$ of the first and second dopants in the same EMLs 462 and 464. Each of the exciton energies at the excited state triplet energy levels $T_1^{TD1}$ and $T_1^{TD2}$ is transferred to each of the excited state singlet energy levels $S_1^{TD1}$ and $S_1^{TD2}$ of its own by a RISC mechanism, and then each of the exciton energies of the excited state singlet energy levels $S_1^{TD1}$ and $S_1^{TD2}$ of the first and second dopants drops to the ground state with light emission.

A part of exciton energy, which is existed at the excited state singlet energy levels $S_1^{H1}$ and $S_1^{H2}$ or at the excited state triplet energy levels $T_1^{H1}$ and $T_1^{H2}$ of the first and second hosts without being transferred to the first and second dopants, can be transferred to each of the excited state singlet energy level $S_1^{ED}$ or the excited state triplet energy level $T_1^{ED}$ of the organic compound in the EEL 390 which is disposed adjacently to the EML1 462 and the EML2 464. As a result, exciton quenching caused by interaction between the accumulated host excitons and the peripheral polaron can be minimized and lifetime reduction of the OLED owing to the electro-oxidation and the photo-oxidation in the course of exciton quenching can be prevented.

The organic compound, which is included in the EEL 490, includes any compound having the structure in Chemical Formulae 1 to 3. As an example, the organic compound can be a delayed fluorescent material. As an example, the EEL 490 can be laminated with a thickness of, but are not limited to, about 1 to 10 nm, and preferably about 1 to about 5 nm.

Each of the first and second hosts, each of which is included in the EML1 462 and the EML2 464, can independently include, but are not limited to, pCzB-2CN, mCzB-2CN, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

In one exemplary embodiment, each of the first and second dopants can be the same as the organic compound. In another exemplary embodiment, each of the first and second dopants can independently include, but are not limited to, any one having the structure of Chemical Formula 4. In still another exemplary embodiment, each of the first and second dopants can independently include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

In one exemplary embodiment, each of the EML1 462 and the EML2 464 can include each of the first and second dopants of about 1 to 70% by weight, preferably about 10 to about 50% by weight, and more preferably about 20 to about 50% by weight, respectively.

In one embodiment, the EML1 462 can have substantially the same thickness as the EML2 464. As an example, each of the EML1 462 and the EML2 464 can be laminated with a thickness of, but are not limited to, about 5 nm to about 100 nm, preferably about 10 nm to about 50 nm, and more preferably about 10 to about 30 nm.

In still another exemplary embodiment, the EML1 462 can have different thickness from the EML2 464. As an example, the EML1 462 can have a thickness as about 1.5 to about 2.5 times as the EML2 464. In this case, the EML1 462 can be laminated with a thickness of, but not limited to, about 10 nm to about 100 nm, and preferably about 15 nm to about 50 nm, and the EML2 464 can be laminated with a thickness of, but are not limited to, about 5 to about 50 nm, and preferably about 5 to 20 nm. Alternatively, the EML2 464 can have a thickness as about 1.5 to about 2.5 times as the EML1 462. In this case, the EML2 464 can be laminated with a thickness of, but not limited to, about 10 nm to about 100 nm, and preferably about 15 to nm about 50 nm, and the EML1 462 can be laminated with a thickness of, but are not limited to, about 5 nm to about 50 nm, and preferably about 5 nm to 20 nm.

In FIG. 9, each of the EML1 462 and the EML2 464 includes the first dopant and the second dopant, each of which is a delayed fluorescent material. While the delayed fluorescent material has excellent luminous efficiency, its color purity and luminous lifetime is poor due to its wide FWHM and its additional CT property.

In another exemplary embodiment, one of the EML1 462 and the EML2 464 includes a first dopant (T dopant) as a delayed fluorescent material, and the other of the EML1 462 and the EML2 464 includes a second dopant (F dopant) as a fluorescent or phosphorescent dopant. Hereinafter, the EML 460, where the EML1 462 includes the first host and the first dopant as the delayed fluorescent material and the EML2 464 includes the second host and the second dopant as the fluorescent or phosphorescent material, will be explained in more detail.

Figure 10:
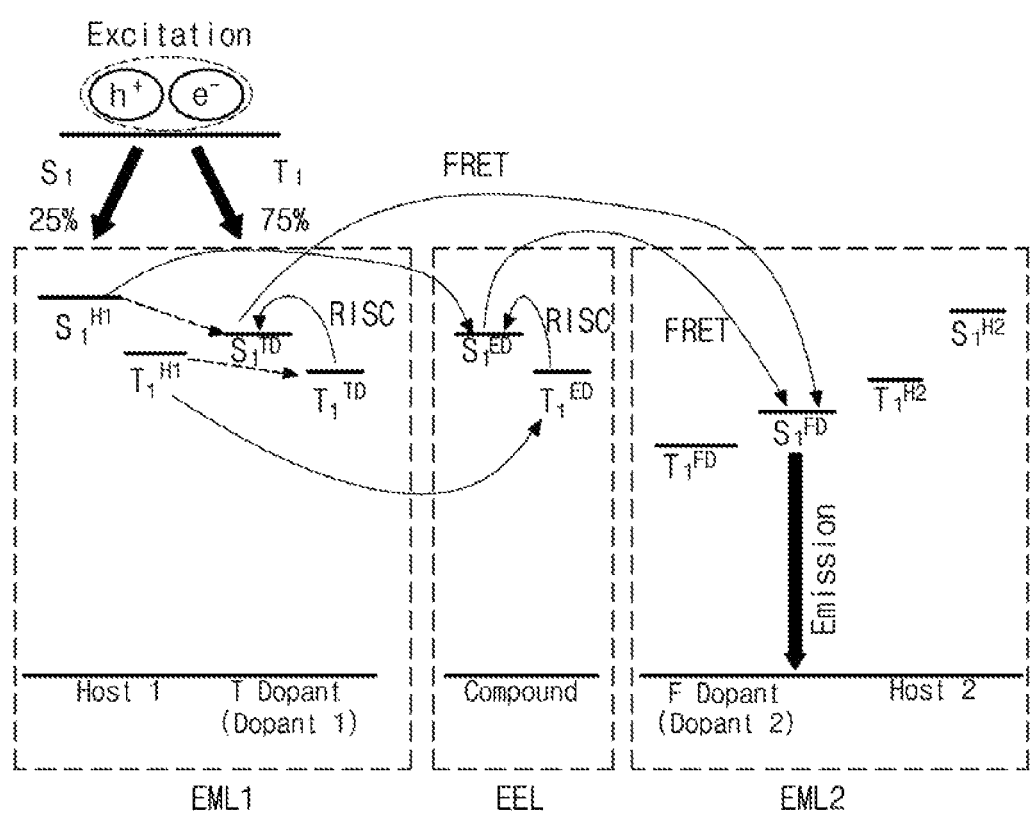
FIG. 10 is a schematic diagram illustrating luminous mechanism by energy level bandgap among luminous materials in accordance with another exemplary embodiment of the present disclosure.

FIG. 10 is a schematic diagram illustrating luminous mechanism by energy level bandgap among luminous materials in accordance with another exemplary embodiment of the present disclosure. As described above, the EML1 462 includes the first dopant (T dopant) which is the delayed fluorescent material. As an example, the first dopant can be the same material as the organic compound (exciton dopant) in the EEL 490. Alternatively, the first dopant can include, but are not limited to, any one having the structure of Chemical Formula 4. In still another exemplary embodiment, the first dopant can include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)

phenyl)-10H-spiro[acridine-9,9'-xanthene] and/or SpiroAC-TRZ. Since the energy level bandgap $\Delta E_{ST}^{TD}$ between the excited state triplet energy level $T_1^{TD}$ and the excited state singlet energy level $S_1^{TD}$ of the first dopant is very low, i.e. equal to or less than about 0.3 eV (See. FIG. 3), the exciton energy at the excited state triplet energy level $T_1^{TD}$ of the first dopant is converted to the excited state singlet energy level $S_1^{TD}$ by RISC mechanism.

In addition, since the energy level bandgap $\Delta E_{ST}^{ED}$ between the excited state triplet energy level $T_1^{ED}$ and the excited state singlet energy level $S_1^{ED}$ of the organic compound is very low, i.e. equal to or less than about 0.3 eV (See, FIG. 3), the exciton energy at the excited state triplet energy level $T_1^{ED}$ of the organic compound in the EEL 490 is converted to the excited state singlet energy level $S_1^{ED}$ by RISC mechanism. While the first dopant and the organic compound as the delayed fluorescent material show high quantum efficiency, their color purity is poor owing to their wide FWHM.

On the contrary, the EML2 464 includes the second host and the second dopant as the fluorescent or phosphorescent material. While the second dopant as the fluorescent or phosphorescent material has an advantage in terms of color purity due to narrow FWHM, its quantum efficiency is limited because its triplet exciton cannot participate in the luminescence process.

However, in this exemplary embodiment, the singlet exciton energies and the triplet exciton energies each with respect to of the first dopant in the EML1 462 and the organic compound in the EEL 490, each of which has the delayed fluorescent property, can be transferred to the second dopant, which can be the fluorescent or phosphorescent material, in the EML2 464 disposed adjacently to the EML1 462 or the EEL 490 by FRET mechanism. Accordingly, the ultimate emission occurs in the second dopant within the EML2 464.

In other words, each of the triplet exciton energies $T_1^{TD}$ and $T_1^{ED}$ of the first dopant in the EML1 462 and the organic compound in the EEL 490 is converted upwardly to each of the singlet exciton energies $S_1^{TD}$ and $S_1^{ED}$ of their own by RISC mechanism. Since each of the excited state singlet energy levels $S_1^{TD}$ and $S_1^{ED}$ of the first dopant and the organic compound is higher than the excited stat singlet energy level $S_1^{FD}$ of the second dopant in the EML2 464, the converted singlet exciton energies $S_1^{TD}$ and $S_1^{ED}$ of the first dopant and the organic compound is transferred to the singlet energy level $S_1^{FD}$ of the second dopant. The second dopant in the EML2 464 can emit light using the triplet exciton energy as well as the singlet exciton energy.

As the exciton energy, which is generated at the first dopant in the EML1 462 and the organic compound in the EEL 490, is transferred to the second dopant in the EML2 464, a hyper-fluorescence can be realized. In this case, the first dopant and the organic compound only act as transferring energy to the second dopant. Substantial light emission is occurred in the EML2 464 including the second dopant which is the fluorescent or phosphorescent material and has a narrow FWHM. Accordingly, the OLED 400 can enhance its quantum efficiency and improve its color purity due to narrow FWHM.

Each of the EML1 462 and the EML2 464 include the first host and the second host, respectively. The exciton energies generated at the first and second hosts should be transferred to the first dopant as the delayed fluorescent material in advance in order to induce light emission. In order to perform such a light emission, each of excited state singlet energy levels $S_1^{H1}$ and $S_1^{H2}$ and excited state triplet energy levels $T_1^{H1}$ and $T_1^{H2}$ of the first and second hosts should be higher than each of the excited state singlet energy levels $S_1^{TD}$ and $S_1^{ED}$ and the excited state triplet energy levels $T_1^{TD}$ and $T_1^{ED}$ of the first dopant and the organic compound, respectively.

For example, when each of the excited triplet energy levels $T_1^{H1}$ and $T_1^{H2}$ of the first and second hosts is not high enough than the excited state triplet energy level $T_1^{TD}$ of the first dopant, respectively, the triplet exciton of the first dopant can be reversely transferred to the excited state triplet energy levels $T_1^{H1}$ and $T_1^{H2}$ of the first and second hosts, which cannot utilize triplet exciton energy. Accordingly, the excitons of the triplet energy level $T_1^{TD}$ of the first dopant can be quenched as a non-emission and the triplet state excitons of the first dopant cannot be involved in the emission. As an example, each of the excited state triplet energy levels $T_1^{H1}$ and $T_1^{H2}$ of the first and second hosts can be higher than the excited state triplet energy levels $T_1^{TD}$ and $T_1^{ED}$ of the first dopant and the organic compound by at least about 0.2 eV.

The excited state singlet energy level $S_1^{H2}$ of the second host is higher than an excited state singlet energy level $S_1^{FD}$ of the second dopant. In this case, the singlet exciton energy generated at the second host can be transferred to the excited singlet energy level $S_1^{FD}$ of the second dopant.

In addition, it is necessary for the EML 460 to exhibit high luminous efficiency and color purity as well as to transfer exciton energy efficiently from the first dopant and the organic compound, each of which is converted to ICT complex state by RISC mechanism, in the EML1 462 and the EEL 490 to the second dopant which is the fluorescent or phosphorescent material in the EML2 464. In order to realize such an OLED 400, each of the excited state triplet energy levels $T_1^{TD}$ and $T_1^{ED}$ of the first dopant and the organic compound is higher than an excited state triplet energy level $T_1^{FD}$ of the second dopant. In one exemplary embodiment, each of the excited state singlet energy levels $S_1^{TD}$ and $S_1^{ED}$ of the first dopant and the organic compound can be higher than an excited state singlet energy level $S_1^{FD}$ of the second dopant as a fluorescent material.

In addition, an energy level bandgap ($|HOMO^{H1}-HOMO^{TD}|$) between a HOMO energy level ($HOMO^{H1}$) of the first host and a HOMO energy level ($HOMO^{TD}$) of the first dopant, or an energy level bandgap ($|LUMO^{H1}-LUMO^{TD}|$) between a LUMO energy level ($LUMO^{H1}$) of the first host and a LUMO energy level ($LUMO^{TD}$) of the first dopant can be equal to or less than about 0.5 eV. Moreover, an energy level bandgap ($|HOMO^{H}-HOMO^{ED}|$) between HOMO energy levels ($HOMO^{H1}$ and $HOMO^{H2}$) of the first and second hosts and a HOMO energy level ($HOMO^{ED}$) of the organic compound, or an energy level bandgap ($|LUMO^{H}-LUMO^{ED}|$) between LUMO energy levels ($LUMO^{H1}$ and $LUMO^{H2}$) of the first and second hosts and a LUMO energy level ($LUMO^{ED}$) of the organic compound can be equal to or less than about 0.2 eV.

When the luminous materials do not satisfy the required energy levels as described above, exciton energies are quenched at the first and second dopants or exciton energies cannot transferred efficiently from the host to the dopants, so that the OLED 400 can have reduced quantum efficiency.

The organic compound in the EEL 490 can include, but is not limited to, any compound having the structure of Chemical Formulae 1 to 3, as described above. The organic compound can have the delayed fluorescent property.

Each of the first host in the EML1 462 and the second host in the EML2 464 can be the same or different from each other. As an example, each of the first and second hosts can independently include, but are not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

In one exemplary embodiment, the first dopant in the EML1 462 can be the same as the organic compound. In another exemplary embodiment, the first dopant can include, but is not limited to, any one having the structure of Chemical Formula 4. In still another exemplary embodiment, the first dopant can include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl) phenyl)-1 OH-spiro[acridine-9,9'-xanthene] and/or SpiroAC-TRZ.

The second dopant in the EML2 464 can have a narrow FWHM and have luminous spectrum having large overlapping area with the absorption spectra of the first dopant and the organic compound. As an example, the second dopant can include, but are not limited to, an organic compound having a quinolino-acridine core such as 5,12-dimethylquinolino[2,3-b]acridine-7,14(5H, 12H)-dione, 5,12-diethylquinolino[2,3-b]acridine-7,14(5H, 12H)-dione, 5,12-dibutyl-3,10-difluoroquinolino[2,3-b]acridine-7,14(5H, 12H)-dione, 5,12-dibutyl-3,10-bis(trifluoromethyl)quinolino[2,3-b]acridine-7,14(5H, 12H)-dione, 5,12-dibutyl-2,3, 9,10-tetrafluoroquinolino[2,3-b]acridine-7,14(5H, 12H)-dione, DCJTB and any metal complexes which can emit light of red, green or blue color.

In one exemplary embodiment, each of the first and second hosts in the EML1 462 or the EML2 464 can have weight ratio equal to or more than the first dopant and the second dopant in the same EMLs 462 and 464, respectively. In addition, the weight ratio of the first dopant in the EML1 462 can be larger than the weight ratio of the second dopant in the EML2 464. In this case, it is possible to transfer enough energy from the first dopant in the EML1 462 to the second dopant in the EML2 464.

The EML1 462 can include the first dopant of about 1 to about 70% by weight, preferably about 10 to about 50% by weight, and more preferably about 20 to about 50% by weight. The weight ratio of the second host can be larger than the weight ratio of the second dopant in the EML2 464. As an example, the EML2 464 can include the second host of about 90 to about 99% by weight, and preferably about 95 to about 99% by weight and the second dopant of about 1 to about 10% by weight, and preferably about 1 to about 5% by weight.

In one embodiment, the EML1 462 can have substantially the same thickness as the EML2 464. As an example, each of the EML1 462 and the EML2 464 can be laminated with a thickness of, but are not limited to, about 5 to about 100 nm, preferably about 10 to about 50 nm, and more preferably about 10 to about 30 nm.

In still another exemplary embodiment, the EML1 462 can have different thickness from the EML2 464. As an example, the EML1 462 can have a thickness as about 1.5 to about 2.5 times as the EML2 464. In this case, the EML1 462 can be laminated with a thickness of, but are not limited to, about 10 nm to about 100 nm, and preferably about 15 nm to about 50 nm, and the EML2 464 can be laminated with a thickness of, but are not limited to, about 5 nm to about 50 nm, and preferably about 5 nm to 20 nm. Alternatively, the EML2 464 can have a thickness as about 1.5 to about 2.5 times as the EML1 462. In this case, the EML2 464 can be laminated with a thickness of, but are not limited to, about 10 nm to about 100 nm, and preferably about 15 nm to about 50 nm, and the EML1 462 can be laminated with a thickness of, but are not limited to, about 5 nm to about 50 nm, and preferably about 5 nm to 20 nm.

When the EML2 464 is disposed adjacently to the HBL 475 in one exemplary embodiment, the second host, which is included in the EML2 464 together with the second dopant, can be the same material as the HBL 475. In this case, the EML2 464 can have a hole blocking function as well as an emission function. In other words, the EML2 464 can act as a buffer layer for blocking holes. In one embodiment, the HBL 475 can be omitted where the EML2 464 can be a hole blocking layer as well as an emitting material layer.

When the EML2 464 is disposed adjacently to the EBL 455 in another exemplary embodiment, the second host can be the same material as the EBL 455. In this case, the EML2 464 can have an electron blocking function as well as an emission function. In other words, the EML2 464 can act as a buffer layer for blocking electrons. In one embodiment, the EBL 455 can be omitted where the EML2 464 can be an electron blocking layer as well as an emitting material layer.

Figure 11:
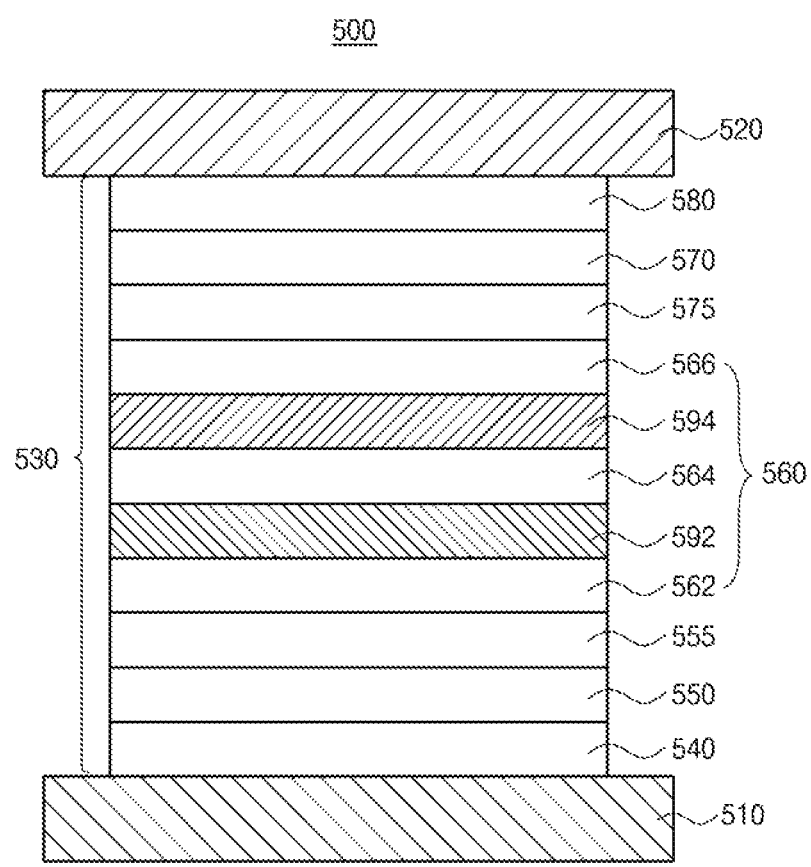
FIG. 11 is a schematic cross-sectional view illustrating an organic light emitting diode in accordance with another exemplary embodiment of the present disclosure.
Figure 12:
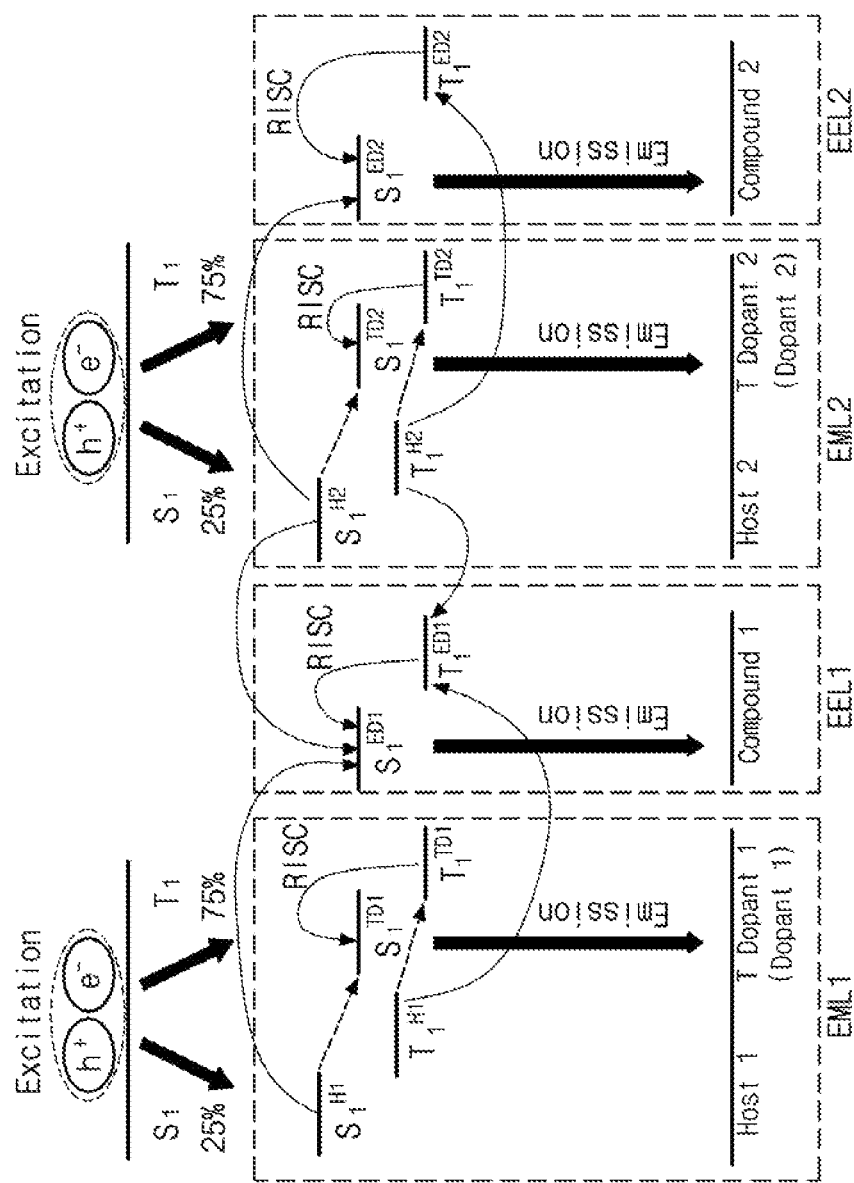
FIG. 12 is a schematic diagram illustrating luminous mechanism by energy level bandgap among luminous materials in accordance with another exemplary embodiment of the present disclosure.

In the above embodiment, only one exciton energy control layer is disposed adjacently to EMLs. Unlike those embodiments, plural exciton energy control layers are laminated. FIG. 11 is a schematic cross-sectional view illustrating an organic light emitting diode in accordance with another exemplary embodiment of the present disclosure, and FIG. 12 is a schematic diagram illustrating luminous mechanism by energy level bandgap among luminous materials in accordance with another exemplary embodiment of the present disclosure.

As illustrated in FIG. 11, the OLED 500 in accordance with the fifth embodiment of the present disclosure include first and second electrodes 510 and 520 facing each other and an emitting unit 530 disposed between the first and second electrodes 510 and 520. In one exemplary embodiment, the emitting unit 530 comprises a HIL 540, a HTL 550, an EML 560, an ETL 570 and an EIL 580 each of which is laminated sequentially over the first electrode 510. The emitting unit 530 can further comprise a first exciton blocking layer, i.e. an EBL 555 disposed between the HTL 550 and the EML 560 and/or a second exciton blocking layer, i.e. a HBL 575 disposed between the EML 560 and the ETL 570.

The first and second electrodes 510 and 520, and the emitting unit 530 except the EML 560 can have substantially the same structure and the same material as the first and second electrodes 310, 410, 320 and 420 and the emitting units 330, 330a and 430 in the above embodiments.

In this exemplary embodiment, the EML 560 includes a first EML (EML1) 562, a second EML (EML2) 564, a first exciton energy control layer (EEL1) 592 and a second exciton energy control layer (EEL2) 594. The EML1 562 includes a first host and a first dopant and the EML2 564 includes a second host and a second dopant. The EEL1 592 is disposed between the EML1 562 and the EML2 564 and includes a first organic compound. The EEL2 594 is disposed between the EML2 564 and the HBL 575 and includes a second organic compound. Alternatively, the EML 560 can further include a third EML (EML3) 566 which is disposed between the EEL2 594 and the HBL 575 and includes a third host and a third dopant.

In one exemplary embodiment, each of the first to third dopants can be a delayed fluorescent material, respectively. As illustrated in FIG. 12, each of excited state singlet energy levels $S_1^{H1}$, $S_1^{H2}$ and $S_1^{H3}$ and excited state triplet energy levels $T_1^{H1}$, $T_1^{H2}$ and $T_1^{H3}$ of the first to third hosts, each of which is included respectively in the EML1 562, EML2 564 and EML3 566, is higher than each of excited state singlet energy levels $S_1^{TD1}$, $S_1^{TD2}$ and $S_1^{TD3}$ and excited state triplet energy levels $T_1^{TD1}$, $T_1^{TD2}$ and $T_1^{TD3}$ of the first to third dopants, respectively.

In addition, each of the excited state singlet energy levels $S_1^{H1}$, $S_1^{H2}$ and $S_1^{H3}$ and the excited state triplet energy levels $T_1^{H1}$, $T_1^{H2}$ and $T_1^{H3}$ of the first to third hosts is higher than each of excited state singlet energy levels $S_1^{ED1}$ and $S_1^{ED2}$ and excited state triplet energy levels $T_1^{ED1}$ and $T_1^{ED2}$ of the first and second organic compounds, each of which is included respectively in the EEL1 592 and the EEL2 594, respectively. When the singlet and triplet energy levels among the first to third hosts, the first to third dopants and the first and second organic compound do not satisfy the requirements above, the excitons of the singlet energy levels $S_1^{TD1}$, $S_1^{TD2}$, $S_1^{TD3}$, $S_1^{ED1}$ and $S_1^{ED2}$ of the first to third dopants and the first and second organic compounds can be reversely transferred to the excited state singlet energy levels $S_1^{H1}$, $S_1^{H2}$ and $S_1^{H3}$ of the first to third hosts, or the excitons of the triplet energy levels $T_1^{TD1}$, $T_1^{TD2}$, $T_1^{TD3}$, $T_1^{ED1}$ and $T_1^{ED2}$ of the first to third dopants and the first and second organic compounds can be reversely transferred to the excited state triplet energy levels $T_1^{H1}$, $T_1^{H2}$ and $T_1^{H3}$ of the first to third hosts. As a result, the triplet excitons of the first to third dopants and the first and second organic compounds cannot contribute to the light emission.

Likely to the above embodiments, an energy level bandgap ($|HOMO^H - HOMO^{TD}|$) between HOMO energy levels ($HOMO^H$, $HOMO^{H2}$ and $HOMO^{H3}$) of the first to third hosts and HOMO energy levels ($HOMO^{TD1}$, $HOMO^{TD2}$ and $HOMO^{TD3}$) of the first to third dopants, or an energy level bandgap ($|LUMO^H - LUMO^{TD}|$) between LUMO energy levels ($LUMO^{H1}$, $LUMO^{H2}$ and $LUMO^{H3}$) of the first to third hosts and LUMO energy levels ($LUMO^{TD1}$, $LUMO^{TD2}$ and $LUMO^{TD3}$) of the first to third dopants can be equal to or less than about 0.5 eV, for example between about 0.1 and about 0.3 eV. In addition, an energy level bandgap (($|HOMO^H - HOMO^{ED}|$) between HOMO energy levels ($HOMO^{H1}$, $HOMO^{H2}$ and $HOMO^{H3}$) of the first to third hosts and HOMO energy levels ($HOMO^{ED1}$ and $HOMO^{ED2}$) of the first and second organic compounds, or an energy level bandgap ($|LUMO^H - LUMO^{ED}|$) between LUMO energy level ($LUMO^{H1}$, $LUMO^{H2}$ and $LUMO^{H3}$) of the first to third hosts and LUMO energy levels ($LUMO^{ED1}$ and $LUMO^{ED2}$) of the first and second organic compounds can be equal to or less than about 0.2 eV.

Each of the exciton energies at the excited state singlet energy levels $S_1^{H1}$, $S_1^{H2}$ and $S_1^{H3}$ and exciton energies at the excited triplet energy levels $T_1^{H1}$, $T_1^{H2}$ and $T_1^{H3}$ of the first to third hosts, each of which is included in the EML1 562, the EML2 564 and the EML3 566, is transferred to each of the excited state singlet energy levels $S_1^{TD1}$, $S_1^{TD2}$ and $S_1^{TD3}$ and the excited state triplet energy levels $T_1^{TD1}$, $T_1^{TD2}$ and $T_1^{TD3}$ of the first to third dopants in the same EMLs 562, 564 and 566. Each of the exciton energies at the excited state triplet energy levels $T_1^{TD1}$, $T_1^{TD2}$ and $T_1^{TD3}$ of the first to third dopants is transferred to each of the excited state singlet energy levels $S_1^{TD1}$, $S_1^{TD2}$ and $S_1^{TD3}$ of its own by a RISC mechanism, and then each of the exciton energies of the excited state singlet energy levels $S_1^{TD1}$, $S_1^{TD2}$ and $S_1^{TD3}$ of the first to third dopants drops to the ground state with light emission.

A part of exciton energy, which is existed at the excited state singlet energy levels $S_1^{H1}$, $S_1^{H2}$ and $S_1^{H3}$ or at the excited state triplet energy levels $T_1^{H1}$, $T_1^{H2}$ and $T_1^{H3}$ of the first to third hosts without being transferred to the first to third dopants, can be transferred to each of the excited state singlet energy levels $S_1^{ED1}$ and $S_1^{ED2}$ or the excited state triplet energy levels $T_1^{ED1}$ and $T_1^{ED2}$ of the first and second organic compounds in the EEL1 592 and the EEL2 594, each of which is disposed adjacently to the EML1 562, the EML2 564 and the EML3 566. As a result, exciton quenching caused by interaction between the accumulated host excitons and the peripheral polaron can be minimized and lifetime reduction of the OLED) 500 owing to the electro-oxidation and the photo-oxidation in the course of exciton quenching can be prevented.

Each of the first and second organic compounds, each of which is included in the EEL1 592 and the EEL2 594, includes any compound having the structure in Chemical Formulae 1 to 3. As an example, each of the EEL1 592 and the EEL2 594 can be laminated with a thickness of, but are not limited to, about 1 nm to 10 nm, and preferably about 1 nm to about 5 nm.

Each of the first to third hosts, each of which is included in the EML1 562, the EML2 564 and the EML3 566, can be the same or be different from each other. As an example, each of the first to third hosts can independently include, but are not limited to, pCzB-2CN, mCzB-2CN, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

Each of the first to third dopants, each of which is included in the EML1 562, the EML2 564 and the EML3 566, can be the same or be different from each other. In one exemplary embodiment, each of the first to third dopants can be independently the same as each of the first and second organic compounds. In another exemplary embodiment, each of the first to third dopants can independently include, but are not limited to, any one having the structure of Chemical Formula 4. In still another exemplary embodiment, each of the first to third dopants can independently include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9, 9'-xanthene] and/or SpiroAC-TRZ.

In one exemplary embodiment, each of the EML1 562, the EML2 564 and the EML3 566 can include each of the first to third dopants of about 1 to 70% by weight, preferably about 10 to about 50% by weight, and more preferably about 20 to about 50% by weight.

In one embodiment, each of the EML1 562, the EML2 564 and the EML3 566 can have substantially the same thickness. As an example, each of the EML1 562, the EML2 564 and the EML3 566 can be laminated with a thickness of, but are not limited to, about 5 nm to about 100 nm, preferably about 10 nm to about 50 nm, and more preferably about 10 nm to about 30 nm.

In still another exemplary embodiment, each of the EML1 562, the EML2 564 and the EML3 566 can have different thickness. As an example, each of the EML1 562 and the EML3 566 can have a thickness as about 1.5 to about 2.5 times as the EML2 564. In this case, each of the EML1 562 and the EML3 566 can be laminated with a thickness of, but are not limited to, about 10 to about 100 nm, and preferably about 15 to about 50 nm, and the EML2 564 can be laminated with a thickness of, but are not limited to, about 5 nm to about 50 nm, and preferably about 5 nm to 20 nm.

Alternatively, the EML2 564 can have a thickness as about 1.5 to about 2.5 times as the EML1 562 and the EML3 566. In this case, the EML2 564 can be laminated with a thickness of, but are not limited to, about 10 nm to about 100 nm, and preferably about 15 nm to about 50 nm, and each of the EML1 562 and the EML3 566 can be laminated with a thickness of, but are not limited to, about 5 nm to about 50 nm, and preferably about 5 nm to 20 nm.

Figure 13:
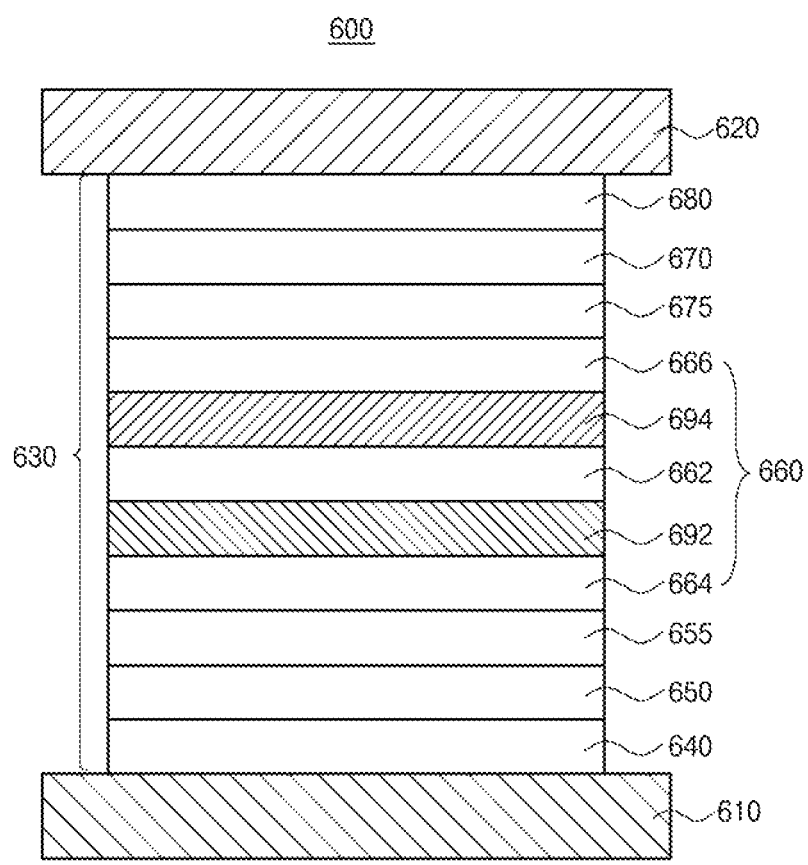
FIG. 13 is a schematic cross-sectional view illustrating an organic light emitting diode in accordance with another exemplary embodiment of the present disclosure.
Figure 14:
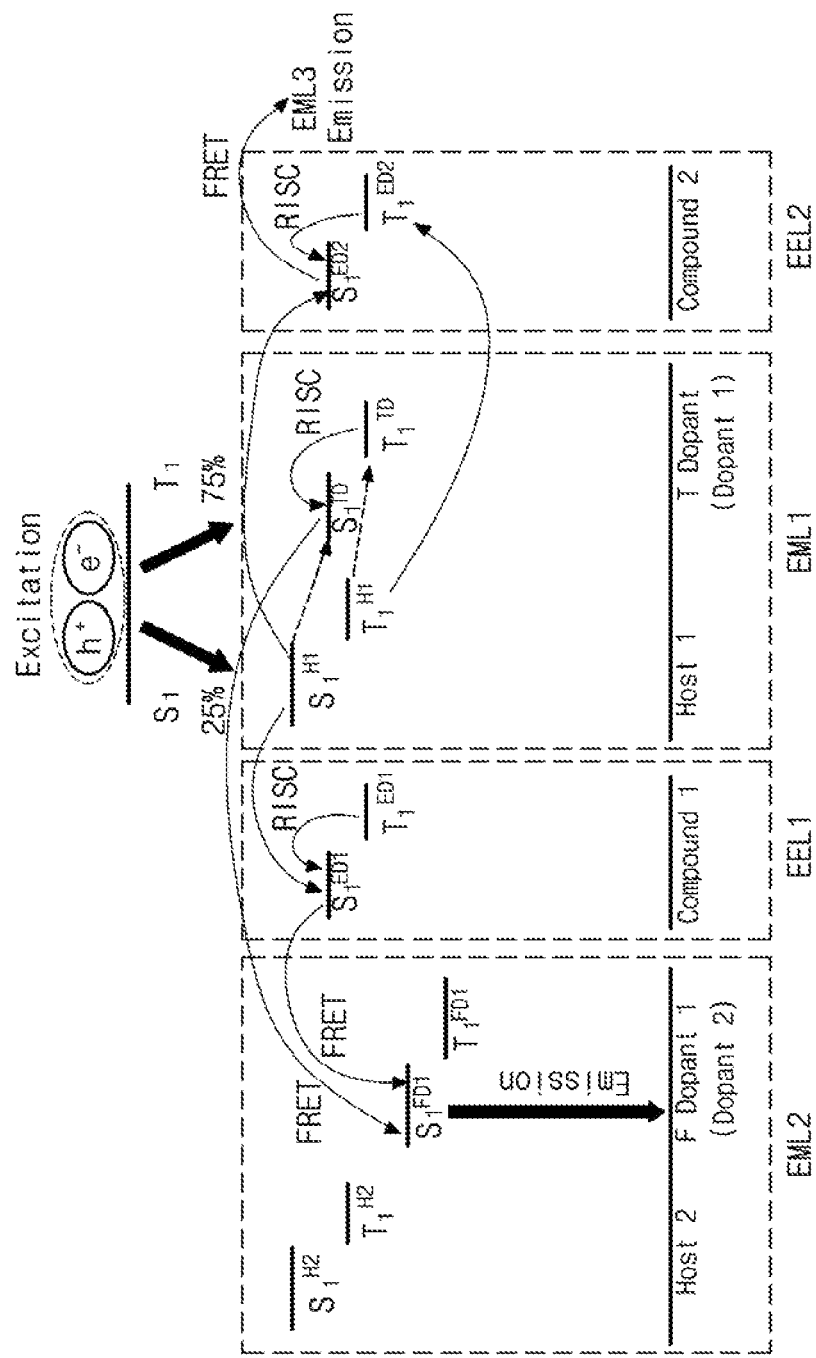
FIG. 14 is a schematic diagram illustrating luminous mechanism by energy level bandgap among luminous materials in accordance with another exemplary embodiment of the present disclosure.

In FIGS. 11 and 12, each of the EML1 562, the EML2 564 and the EML3 566 includes the first to third dopants as the delayed fluorescent material. Unlike those embodiments, EMLs can include different types of dopants. FIG. 13 is a schematic cross-sectional view illustrating an organic light emitting diode in accordance with another exemplary embodiment of the present disclosure. FIG. 14 is a schematic diagram illustrating luminous mechanism by energy level bandgap among luminous materials in accordance with another exemplary embodiment of the present disclosure.

As illustrated in FIG. 13, the OLED 600 in accordance with the sixth embodiment of the present disclosure include first and second electrodes 610 and 620 facing each other and an emitting unit 630 disposed between the first and second electrodes 610 and 620. In one exemplary embodiment, the emitting unit 630 comprises a HIL 640, a HTL 650, an EML 660, an ETL 670 and an EIL 680 each of which is laminated sequentially over the first electrode 610. The emitting unit 630 can further comprise a first exciton blocking layer, i.e. an EBL 655 disposed between the HTL 650 and the EML 660 and/or a second exciton blocking layer, i.e. a HBL 675 disposed between the EML 660 and the ETL 670.

The first and second electrodes 610 and 620, and the emitting unit 630 except the EML 660 can have substantially the same structure and the same material as the first and second electrodes 310, 410, 510, 320, 420 and 520 and the emitting units 330, 330a, 430 and 530 in the above embodiments.

In the exemplary sixth embodiment, the EML 660 includes a first EML (EML1) 662, a second EML (EML2) 664, a first exciton energy control layer (EEL) 692 and a second exciton energy control layer (EEL2) 694. The EML1 662 includes a first host and a first dopant and the EML2 664 includes a second host and a second dopant and is disposed between the EBL 655 and the EML1 662. The EEL1 692 includes a first organic compound and is disposed between the EML1 662 and the EML2 664. The EEL2 694 includes a second organic compound and disposed between the EML1 662 and the HBL 675. Alternatively, the EML 660 can further include a third EML (EML3) 666 which includes a third host and a third dopant and is disposed between the EEL2 694 and the HBL 675. The first dopant (T dopant) in the EML1 662 is a delayed fluorescent material and each of the second and third dopants (F dopant 1 and F dopant 2) in the EML2 664 and EML3 666 is a fluorescent or phosphorescent material, respectively.

The EML1 662 includes the first dopant as the delayed fluorescent material. Since the energy level bandgap $\Delta E_{ST}^{TD}$ between the excited state triplet energy level $T_1^{TD}$ and the excited state singlet energy level $S_1^{TD}$ of the first dopant is very low, i.e. equal to or less than about 0.3 eV (See. FIG. 3), the exciton energy at the excited state triplet energy level $T_1^{TD}$ of the first dopant is converted upwardly to the excited state singlet energy level $S_1^{TD}$ by RISC mechanism.

In addition, since the energy level bandgap $\Delta E_{ST}^{TD}$ between the excited state triplet energy levels $T_1^{ED1}$ and $T_1^{ED2}$ and the excited state singlet energy level $S_1^{ED1}$ and $S_1^{ED2}$ of the first and second organic compounds, each of which is included respectively in the EEL1 692 and the EEL2 694, is very low, i.e. equal to or less than about 0.3 eV (See. FIG. 3), each of the exciton energy at the excited state triplet energy levels $T_1^{ED1}$ and $T_1^{ED2}$ of the first and second organic compounds in the EEL1 692 and the EEL2 694 is converted to each of the excited state singlet energy level $S_1^{ED1}$ and $S_1^{ED2}$ by RISC mechanism. While the first dopant and the first and second organic compounds as the delayed fluorescent material show high quantum efficiency, their color purity is poor owing to their wide FWHM.

On the contrary, each of the EML2 664 and the EML3 666 includes the second or third host and the second or third dopant as the fluorescent or phosphorescent material. While the second and third dopants as the fluorescent or phosphorescent material have an advantage in terms of color purity due to narrow FWHM, their quantum efficiencies are limited because their triplet exciton cannot participate in the luminescence process.

However, in this exemplary embodiment, the singlet exciton energies and the triplet exciton energies with respect to each of the first dopant, which is included in the EML1 662 and having the delayed fluorescent property, and the first and the second organic compounds, each of which is included in the EEL1 692 and the EEL2 694 and has the delayed fluorescent property, can be transferred to the second and third dopants, each of which is included in the EML2 664 and the EML3 666 and is a fluorescent or phosphorescent material, by FRET mechanism. Accordingly, the ultimate emission occurs in the second and third dopants within the EML2 664 and the EML3 666.

In other words, each of the triplet exciton energies $T_1^{TD}$, $T_1^{ED1}$ and $T_1^{ED2}$ of the first dopant in the EML1 662 and the first and second organic compounds in the EEL1 692 and the EEL2 694 is converted upwardly to each of the singlet exciton energies $S_1^{TD}$, $S_1^{ED1}$ and $S_1^{ED2}$ of their own by RISC mechanism. Since each of the excited state singlet energy levels $S_1^{TD}$, $S_1^{ED1}$ and $S_1^{ED2}$ of the first dopant and the first and second organic compounds is higher than each of the excited state singlet energy levels $S_1^{FD1}$ and $S_1^{FD2}$ of the second and third dopants in the EML2 664 and the EML3 666, the converted singlet exciton energies $S_1^{TD}$, $S_1^{ED1}$ and $S_1^{ED2}$ of the first dopant and the first and second organic compounds is transferred to each of the singlet energy levels $S_1^{FD1}$ and $S_1^{FD2}$ of the second and third dopants. Each of the second and third dopants in the EML2 664 and the EML3 666 can emit light using the triplet exciton energy as well as the singlet exciton energy.

As the exciton energy, which is generated at the first dopant in the EML1 662 and the first and second organic compounds in the EEL1 692 and the EEL2 694, is transferred to each of the second and third dopants in the EML2 664 and the EML3 666, a hyper-fluorescence can occur. In this case, the first dopant and the first and second organic compounds only act as transferring energy to the second and third dopants. Substantial light emission is occurred in the EML2 664 and the EML3 666, each of which includes the second dopant or the third dopant as the fluorescent or phosphorescent material and has a narrow FWHM. Accordingly, the OLED 600 can enhance its quantum efficiency and improve its color purity due to narrow FWHM.

Each of the EML1 662, the EML2 664 and the EML3 666 includes a first host, a second host and a third host, respectively. Each of the exciton energies generated at the first to third hosts should be transferred to first dopant as the delayed fluorescent material in advance in order to induce light emission. In order to perform such a light emission, each of excited state singlet energy levels $S_1^{H1}$, $S_1^{H2}$ and $S_1^{H3}$ and excited state triplet energy levels $T_1^{H1}$, $T_1^{H2}$ and $T_1^{H3}$ of the first to third hosts should be higher than each of the excited state singlet energy levels $S_1^{TD}$, $S_1^{ED1}$ and $S_1^{ED2}$ and the excited state triplet energy levels $T_1^{TD}$, $T_1^{ED1}$ and $T_1^{ED2}$ of the first dopant and the first and second organic compounds as the delayed fluorescent material, respectively. As an example, each of the excited state triplet energy levels $T_1^{H1}$, $T_1^{H2}$ and $T_1^{H3}$ of the first to third hosts can be higher than each of the excited state triplet energy levels $T_1^{TD}$, $T_1^{ED1}$ and $T_1^{ED2}$ of the first dopant and the first and second organic compounds by at least about 0.2 eV.

Moreover, each of the excited state singlet energy levels $S_1^{H1}$ and $S_1^{H3}$ of the second and third hosts is higher than each of excited state singlet energy levels $S_1^{FD1}$ and $S_1^{FD2}$ of the second and third dopants, respectively. In this case, each of the singlet exciton energies generated at the second and third hosts can be transferred to each of the excited singlet energy levels $S_1^{FD1}$ and $S_1^{FD2}$ of the second and third dopants.

Moreover, it is necessary for the EML 660 to implement high luminous efficiency and color purity as well as to transfer exciton energy efficiently from the first dopant and the first and second organic compounds, each of which is converted to ICT complex state by RISC mechanism, in the EML1 662, EEL1 692 and the EEL2 694 to the second and third dopants each of which is the fluorescent or phosphorescent material in the EML2 664 and the EML3 666. In order to realize such an OLED 600, each of the excited state triplet energy levels $T_1^{TD}$, $T_1^{ED1}$ and $T_1^{ED2}$ of the first dopant and the first and second organic compounds, each of which is included in the EML1 662, the EEL1 692 and the EEL2 694, is higher than each of excited state triplet energy levels $T_1^{FD1}$ and $T_1^{FD2}$ of the second and third dopants. In one exemplary embodiment, each of the excited state singlet energy levels $S_1^{TD}$, $S_1^{ED1}$ and $S_1^{ED2}$ of the first dopant and the first and second organic compound can be higher than each of excited state singlet energy levels $S_1^{FD1}$ and $S_1^{FD2}$ of the second and third dopants as a fluorescent material.

In addition, an energy level bandgap ($|HOMO^{H1}-HOMO^{TD}|$) between a HOMO energy level ($HOMO^{H1}$) of the first host and a HOMO energy level ($HOMO^{TD}$) of the first dopant, or an energy level bandgap ($|LUMO^{H1}-LUMO^{TD}|$) between a LUMO energy level ($LUMO^{H1}$) of the first host and a LUMO energy level ($LUMO^{TD}$) of the first dopant can be equal to or less than about 0.5 eV. Moreover, an energy level bandgap ($|HOMO^{H}-HOMO^{ED}|$) between HOMO energy levels ($HOMO^{H1}$, $HOMO^{H2}$ and $HOMO^{H3}$) of the first to third hosts and HOMO energy levels ($HOMO^{ED1}$ and $HOMO^{ED2}$) of the first and second organic compounds, or an energy level bandgap ($|LUMO^{H}-LUMO^{ED}|$) between LUMO energy levels ($LUMO^{H1}$, $LUMO^{H2}$ and $LUMO^{H3}$) of the first to third hosts and LUMO energy levels ($LUMO^{ED1}$ and $LUMO^{ED2}$) of the first and second organic compounds can be equal to or less than about 0.2 eV.

Each of the first and second organic compounds, each of which is included in the EEL1 692 or the EEL2 694, can be the same as or different from each other. As an example, each of the first and second organic compounds can independently include, but are not limited to, any compound having the structure of Chemical Formulae 1 to 3, as described above. Each of the first and second organic compounds can have the delayed fluorescent property.

Each of the first host in the EML1 662, the second host in the EML2 664 and the third host in the EML3 666 can be the same or different from each other. As an example, each of the first to third hosts can independently include, but are not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

In one exemplary embodiment, the first dopant in the EML1 662 can be the same as the first and second organic compounds. In another exemplary embodiment, the first dopant can include, but are not limited to, any one having the structure of Chemical Formula 4. In still another exemplary embodiment, the first dopant can include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

Each of the second and third dopants in the EML2 664 and the EML3 666 can have narrow FWHM and have luminous spectrum having large overlapping area with the absorption spectra of the first dopant and the first and second organic compound. As an example, each of the second and third dopants can independently include, but are not limited to, an organic compound having a quinolino-acridine core such as 5,12-dimethylquinolino[2,3-b]acridine-7,14(5H,12H)-dione, 12-diethylquinolino[2,3-b]acridine-7,14(5H,12H)-dione, 5,12-dibutyl-3,10-difluoroquinolino[2,3-b]acridine-7,14(5H, 12H)-dione, 5,12-dibutyl-3,10-bis(trifluoromethyl)quinolino[2,3-b]acridine-7,14(5H, 12H)-dione, 5,12-dibutyl-2,3,9,10-tetrafluoroquinolino[2,3-b]acridine-7,14(5H, 12H)-dione, DCJTB and any metal complexes which can emit light of red, green or blue color.

In one exemplary embodiment, each of the first to third hosts in the EML1 662, the EML2 664 or the EML3 666 can have weight ratio equal to or more than the first to third dopants in the same EMLs 662, 664 and 666, respectively. In addition, the weight ratio of the first dopant in the EML1 662 can be larger than each of the weight ratio of the second and third dopants in the EML2 664 and the EML3 666. In this case, it is possible to transfer enough energy from the first dopant in the EML1 662 to the second and third dopants in the EML2 664 and the EML3 666.

The EML1 662 can include the first dopant of about 1 to about 70% by weight, preferably about 10 to about 50% by weight, and more preferably about 20 to about 50% by weight. Each of the weight ratios of the second and third hosts can be larger than each of the weight ratios of the second and third dopants in the EML2 664 and the EML3 666. As an example, each of the EML2 664 and the EML3 666 can include the second or third host of about 90 to about 99% by weight, and preferably about 95 to about 99% by weight and the second or third dopant of about 1 to about 10% by weight, and preferably about 1 to about 5% by weight.

In one embodiment, each of the EML1 662, the EML2 664 and the EML3 666 can have substantially the same thickness. As an example, each of the EML1 662, the EML2 664 and the EML3 666 can be laminated with a thickness of, but are not limited to, about 5 nm to about 100 nm, preferably about 10 nm to about 50 nm, and more preferably about 10 nm to about 30 nm.

In still another exemplary embodiment, each of the EML1 662, the EML2 664 and the EML3 666 can have different thickness. As an example, each of the EML1 662 and the EML3 666 can have a thickness as about 1.5 to about 2.5 times as the EML2 664. In this case, each of the EML1 662 and the EML3 666 can be laminated with a thickness of, but are not limited to, about 10 nm to about 100 nm, and preferably about 15 nm to about 50 nm, and the EML2 664 can be laminated with a thickness of, but are not limited to, about 5 nm to about 50 nm, and preferably about 5 nm to 20 nm. Alternatively, the EML2 664 can have a thickness as about 1.5 to about 2.5 times as each of the EML1 662 and the EML3 666. In this case, the EML2 664 can be laminated with a thickness of, but are not limited to, about 10 nm to about 100 nm, and preferably about 15 nm to about 50 nm, and each of the EML1 662 and the EML3 666 can be laminated with a thickness of, but are not limited to, about 5 nm to about 50 nm, and preferably about 5 nm to 20 nm.

When the EML2 664 is disposed adjacently to the EBL 655 in one exemplary embodiment, the second host, which is included in the EML2 664 together with the second dopant, can be the same material as the EBL 655. In this case, the EML2 664 can have an electron blocking function as well as an emission function. In other words, the EML2 664 can act as a buffer layer for blocking electrons. In one embodiment, the EBL 655 can be omitted where the EML2 664 can be an electron blocking layer as well as an emitting material layer.

When the EML3 666 is disposed adjacently to the HBL 675 in another exemplary embodiment, the third host, which is included in the EML3 666 together with the third dopant, can be the same material as the HBL 675. In this case, the EML3 666 can have a hole blocking function as well as an emission function. In other words, the EML3 666 can act as a buffer layer for blocking holes. In one embodiment, the HBL 675 can be omitted where the EML3 666 can be a hole blocking layer as well as an emitting material layer.

In still another exemplary embodiment, the second host in the EML2 664 can be the same material as the EBL 655 and the third host in the EML3 666 can be the same material as the HBL 675. In this embodiment, the EML2 664 can have an electron blocking function as well as an emission function, and the EML3 666 can have a hole blocking function as well as an emission function. In other words, each of the EML2 664 and the EML3 666 can act as a buffer layer for blocking electrons or hole, respectively. In one embodiment, the EBL 655 and the HBL 675 can be omitted where the EML2 664 can be an electron blocking layer as well as an emitting material layer and the EML3 666 can be a hole blocking layer as well as an emitting material layer.

Figure 15:
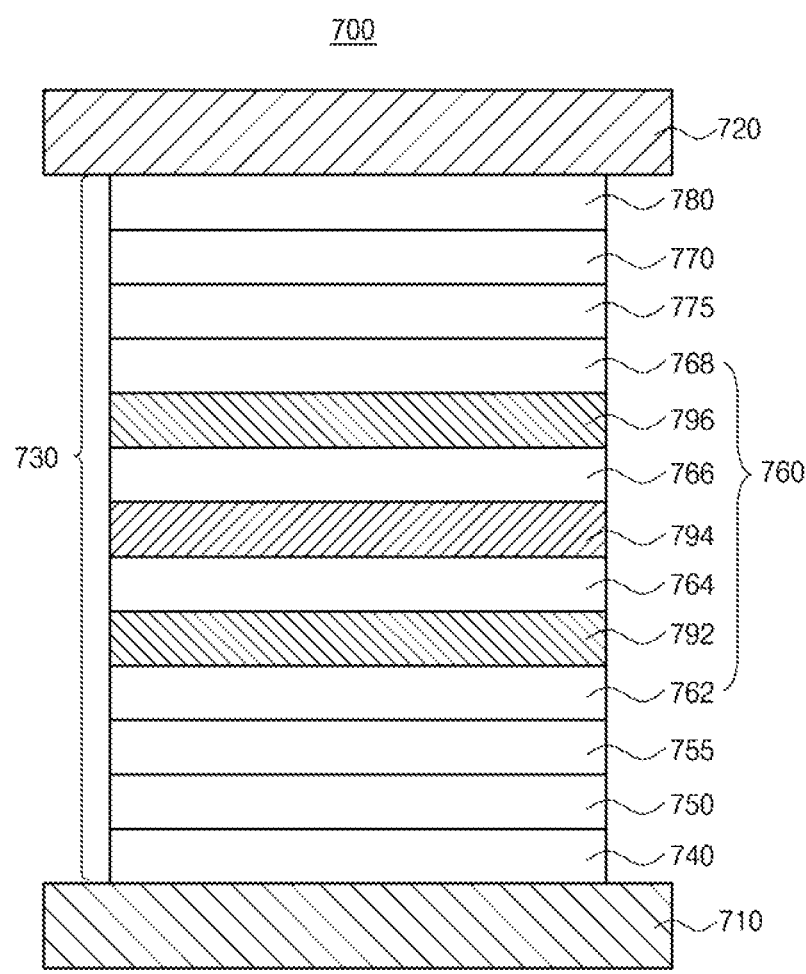
FIG. 15 is a schematic cross-sectional view illustrating an organic light emitting diode in accordance with another exemplary embodiment of the present disclosure.
Figure 16:
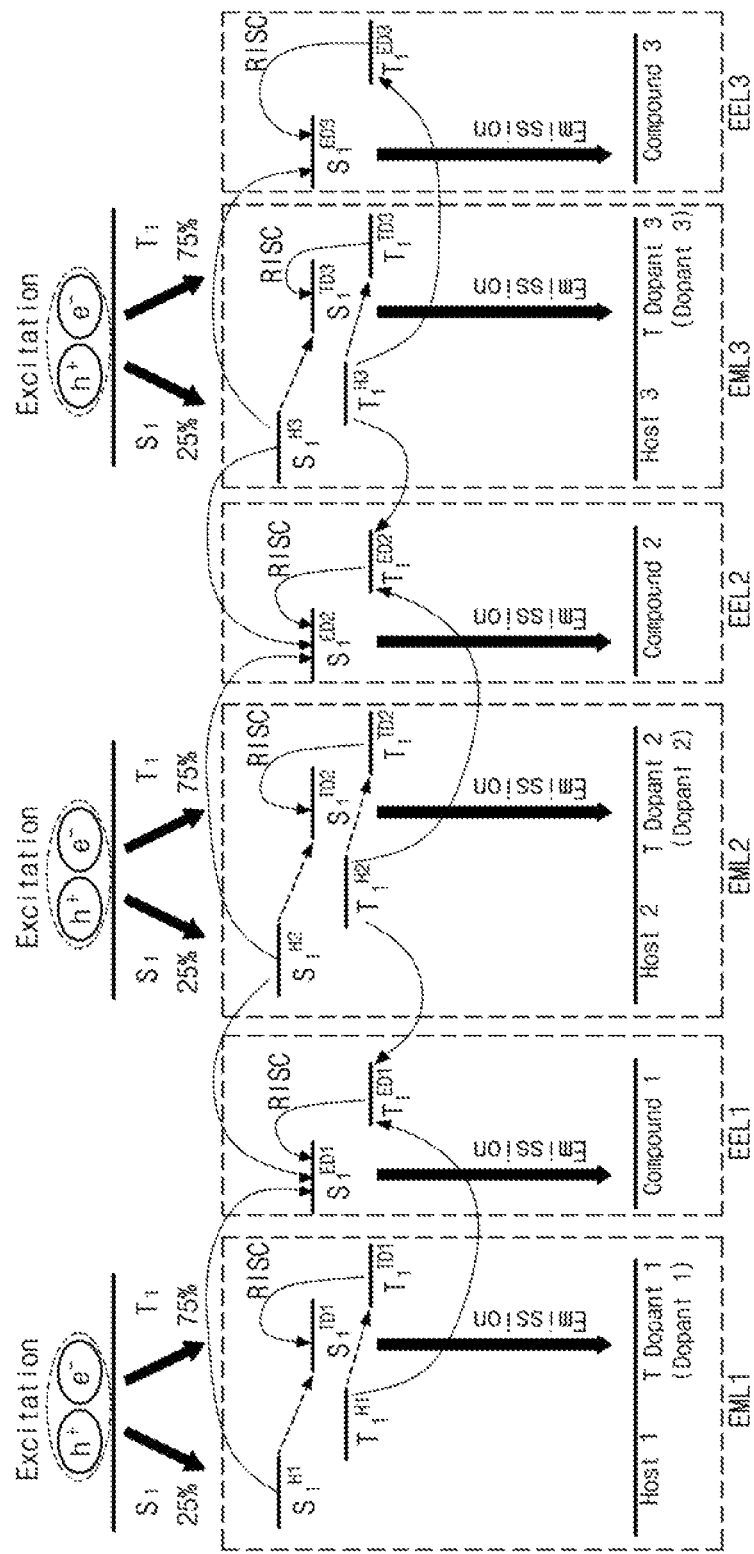
FIG. 16 is a schematic diagram illustrating luminous mechanism by energy level bandgap among luminous materials in accordance with another exemplary embodiment of the present disclosure.

In the above embodiments, two exciton energy control layers are disposed adjacently to EMLs. Unlike those embodiments, three exciton energy control layers are laminated adjacently to EMLs. FIG. 15 is a schematic cross-sectional view illustrating an organic light emitting diode in accordance with another exemplary embodiment of the present disclosure. FIG. 16 is a schematic diagram illustrating luminous mechanism by energy level bandgap among luminous materials in accordance with another exemplary embodiment of the present disclosure.

As illustrated in FIG. 15, the OLED 700 in accordance with the seventh embodiment of the present disclosure include first and second electrodes 710 and 720 facing each other and an emitting unit 730 disposed between the first and second electrodes 710 and 720. In one exemplary embodiment, the emitting unit 730 comprises a HIL 740, a HTL 750, an EML 760, an ETL 770 and an EIL 780 each of which is laminated sequentially over the first electrode 710. The emitting unit 730 can further comprise a first exciton blocking layer, i.e. an EBL 755 disposed between the HTL 750 and the EML 760 and/or a second exciton blocking layer, i.e. a HBL 775 disposed between the EML 760 and the ETL 770.

The first and second electrodes 710 and 720, and the emitting unit 730 except the EML 760 can have substantially the same structure and the same material as the first and second electrodes 310, 410, 510, 610, 320, 420, 520 and 620 and the emitting units 330, 330a, 430, 530 and 630 in the above embodiments.

In this exemplary embodiment, the EML 760 includes a first EML (EML1) 762, a second EML (EML2) 764, a third EML (EML3) 766, a first exciton energy control layer (EEL1) 792, a second exciton energy control layer (EEL2) 794 and a third exciton energy control layer (EEL3) 796. The EML1 762 includes a first host and a first dopant, the EML2 764 includes a second host and a second dopant and the EML3 766 includes a third host and a third dopant. The EEL1 792 is disposed between the EML1 762 and the EML2 764 and includes a first organic compound. The EEL2 794 is disposed between the EML2 764 and the EML3 766 and includes a second organic compound. The EEL3 796 is disposed between the EML3 766 and the HBL 775 and includes a third organic compound. Alternatively, the EML 760 can further include a fourth EML (EML4) 768 which is disposed between the EEL3 796 and the HBL 775 and includes a fourth host and a fourth dopant.

In one exemplary embodiment, each of the first to fourth dopants can be a delayed fluorescent material, respectively. As illustrated in FIG. 16, each of excited state singlet energy levels $S_1^{H1}$, $S_1^{H2}$, $S_1^{H3}$ and $S_1^{H4}$ and excited state triplet energy levels $T_1^{H1}$, $T_1^{H2}$, $T_1^{H3}$ and $T_1^{H4}$ of the first to fourth hosts, each of which is included respectively in the EML1 762, EML2 764, EML3 766 and EML4 768, is higher than each of excited state singlet energy levels $S_1^{TD1}$, $S_1^{TD2}$, $S_1^{TD3}$ and $S_1^{TD4}$ and excited state triplet energy levels $T_1^{TD1}$, $T_1^{TD2}$, $T_1^{TD3}$ and $T_1^{TD4}$ of the first to fourth dopants, respectively.

In addition, each of the excited state singlet energy levels $S_1^{H1}$, $S_1^{H2}$, $S_1^{H3}$ and $S_1^{H4}$ and the excited state triplet energy levels $T_1^{H1}$, $T_1^{H2}$, $T_1^{H3}$ and $T_1^{H4}$ of the first to fourth hosts is higher than each of excited state singlet energy levels $S_1^{ED1}$, $S_1^{ED2}$ and $S_1^{ED3}$ and excited state triplet energy levels $T_1^{ED1}$, $T_1^{ED2}$ and $T_1^{ED3}$ of the first to third organic compounds, each of which is included respectively in the EEL1 792, the EEL2 794 and the EEL3 796, respectively. When the singlet and triplet energy levels among the first to fourth hosts, the first to fourth dopants and the first to third organic compound do not satisfy the requirements above, the excitons of the singlet energy levels $S_1^{TD1}$, $S_1^{TD2}$, $S_1^{TD3}$, $S_1^{TD4}$, $S_1^{ED1}$, $S_1^{ED2}$ and $S_1^{ED3}$ of the first to fourth dopants and the first to third organic compounds can be reversely transferred to the excited state singlet energy levels $S_1^{H1}$, $S_1^{H2}$, $S_1^{H3}$ and $S_1^{H4}$ of the first to fourth hosts, or the excitons of the triplet energy levels $T_1^{TD1}$, $T_1^{TD2}$, $T_1^{TD3}$, $T_1^{TD4}$, $T_1^{ED1}$, $T_1^{ED2}$ and $T_1^{ED3}$ of the first to fourth dopants and the first to third organic compounds can be reversely transferred to the excited state triplet energy levels $T_1^{H1}$, $T_1^{H2}$, $T_1^{H3}$ and $T_1^{H4}$ of the first to fourth hosts. As a result, the triplet excitons of the first to fourth dopants and the first to third organic compounds cannot contribute to the light emission.

Likely to the above embodiments, an energy level bandgap ($|HOMO^H - HOMO^{TD}|$) between HOMO energy levels ($HOMO^{H1}$, $HOMO^{H2}$, $HOMO^{H3}$ and $HOMO^{H4}$) of the first to fourth hosts and HOMO energy levels ($HOMO^{TD1}$, $HOMO^{TD2}$, $HOMO^{TD3}$ and $HOMO^{TD4}$) of the first to fourth dopants, or an energy level bandgap ($|LUMO^H - LUMO^{TD}|$) between LUMO energy levels ($LUMO^{H1}$, $LUMO^{H2}$, $LUMO^{H3}$ and $LUMO^{H4}$) of the first to fourth hosts and LUMO energy levels ($LUMO^{TD1}$, $LUMO^{TD2}$, $LUMO^{TD3}$ and LUMO$^{TD4}$) of the first to fourth dopants can be equal to or less than about 0.5 eV, for example between about 0.1 and about 0.3 eV. In addition, an energy level bandgap (|HOMO$^H$−HOMO$^{ED}$|) between HOMO energy levels (HOMO$^{H1}$, HOMO$^{H2}$, HOMO$^{H3}$ and HOMO$^{H4}$) of the first to fourth hosts and HOMO energy levels (HOMO$^{ED1}$, HOMO$^{ED2}$ and HOMO$^{ED3}$) of the first to third organic compounds, or an energy level bandgap (|LUMO$^H$−LUMO$^{ED}$|) between LUMO energy level (LUMO$^{H1}$, LUMO$^{H2}$, LUMO$^{H3}$ and LUMO$^{H4}$) of the first to fourth hosts and LUMO energy levels (LUMO$^{ED1}$, LUMO$^{ED2}$ and LUMO$^{ED3}$) of the first to third organic compounds can be equal to or less than about 0.2 eV.

Each of the exciton energies at the excited state singlet energy levels $S_1^{H1}$, $S_1^{H2}$, $S_1^{H3}$ and $S_1^{H4}$ and exciton energies at the excited triplet energy levels $T_1^{H1}$, $T_1^{H2}$, $T_1^{H3}$ and $T_1^{H4}$ of the first to fourth hosts, each of which is included in the EML1 762, the EML2 764, the EML3 766 and the EML4 768, is transferred to each of the excited state singlet energy levels $S_1^{TD1}$, $S_1^{TD2}$, $S_1^{TD3}$ and $S_1^{TD4}$ and the excited state triplet energy levels $T_1^{TD1}$, $T_1^{TD2}$, $T_1^{TD3}$ and $T_1^{TD4}$ of the first to fourth dopants in the same EMLs 762, 764, 766 and 768. Each of the exciton energies at the excited state triplet energy levels $T_1^{TD1}$, $T_1^{TD2}$, $T_1^{TD3}$ and $T_1^{TD4}$ of the first to fourth dopants is transferred to each of the excited state singlet energy levels $S_1^{TD1}$, $S_1^{TD2}$, $S_1^{TD3}$ and $S_1^{TD4}$ of its own by RISC mechanism, and then each of the exciton energies of the excited state singlet energy levels $S_1^{TD1}$, $S_1^{TD2}$, $S_1^{TD3}$ and $S_1^{TD4}$ of the first to fourth dopants drops to the ground state with light emission.

A part of exciton energy, which is existed at the excited state singlet energy levels $S_1^{H1}$, $S_1^{H2}$, $S_1^{H3}$ and $S_1^{H4}$ or at the excited state triplet energy levels $T_1^{H1}$, $T_1^{H2}$, $T_1^{H3}$ and $T_1^{H4}$ of the first to fourth hosts without being transferred to the first to fourth dopants, can be transferred to each of the excited state singlet energy levels $S_1^{ED1}$, $S_1^{ED2}$ and $S_1^{ED3}$ or the excited state triplet energy levels $T_1^{ED1}$, $T_1^{ED2}$ and $T_1^{ED3}$ of the first to third organic compounds in the EEL1 792, the EEL2 794 and the EEL3 796, each of which is disposed adjacently to the EML1 762, the EML2 764, the EML3 766 and the EML4 768. As a result, exciton quenching caused by interaction between the accumulated host excitons and the peripheral polaron can be minimized and lifetime reduction of the OLED owing to the electro-oxidation and the photo-oxidation in the course of exciton quenching can be prevented.

Each of the first to third organic compounds, each of which is included in the EEL1 792, the EEL2 794 and the EEL3 796, includes any compound having the structure in Chemical Formulae 1 to 3. As an example, each of the EEL1 792, the EEL2 794 and the EEL3 796 can be laminated with a thickness of, but are not limited to, about 1 to 10 nm, and preferably about 1 to about 5 nm.

Each of the first to fourth hosts, each of which is included in the EML1 762, the EML2 764, the EML3 766 and the EML4 768, can be the same or be different from each other. As an example, each of the first to fourth hosts can independently include, but are not limited to, pCzB-2CN, mCzB-2CN, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

Each of the first to fourth dopants, each of which is included in the EML1 762, the EML2 764, the EML3 766 and the EML4 768, can be the same or be different from each other. In one exemplary embodiment, each of the first to fourth dopants can be independently the same as each of the first to third organic compounds. In another exemplary embodiment, each of the first to fourth dopants can independently include, but are not limited to, any one having the structure of Chemical Formula 4. In still another exemplary embodiment, each of the first to fourth dopants can independently include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

In one exemplary embodiment, each of the EML1 762, the EML2 764, the EML3 766 and the EML4 768 can include each of the first to fourth dopants of about 1 to 70% by weight, preferably about 10 to about 50% by weight, and more preferably about 20 to about 50% by weight.

In one embodiment, each of the EML1 762, the EML2 764, the EML3 766 and the EML4 768 can have substantially the same thickness. As an example, each of the EML1 762, the EML2 764, the EML3 766 and the EML4 768 can be laminated with a thickness of, but are not limited to, about 5 nm to about 100 nm, preferably about 10 nm to about 50 nm, and more preferably about 10 nm to about 30 nm.

In still another exemplary embodiment, each of the EML 762, the EML2 764, the EML3 766 and the EML4 768 can have different thickness. As an example, each of the EML1 762 and the EML4 768 can have a thickness as about 1.5 to about 2.5 times as each of the EML2 764 and the EML3 766. In this case, each of the EML1 762 and the EML4 768 can be laminated with a thickness of, but are not limited to, about 10 nm to about 100 nm, and preferably about 15 nm to about 50 nm, and each of the EML2 764 and the EML3 766 can be laminated with a thickness of, but are not limited to, about 5 nm to about 50 nm, and preferably about 5 nm to 20 nm. Alternatively, each of the EML2 764 and the EML3 766 can have a thickness as about 1.5 to about 2.5 times as each of the EML1 762 and the EML4 768. In this case, each of the EML2 764 and the EML3 766 can be laminated with a thickness of, but are not limited to, about 10 nm to about 100 nm, and preferably about 15 nm to about 50 nm, and each of the EML1 762 and the EML4 768 can be laminated with a thickness of, but are not limited to, about 5 nm to about 50 nm, and preferably about 5 nm to 20 nm.

Figure 17:
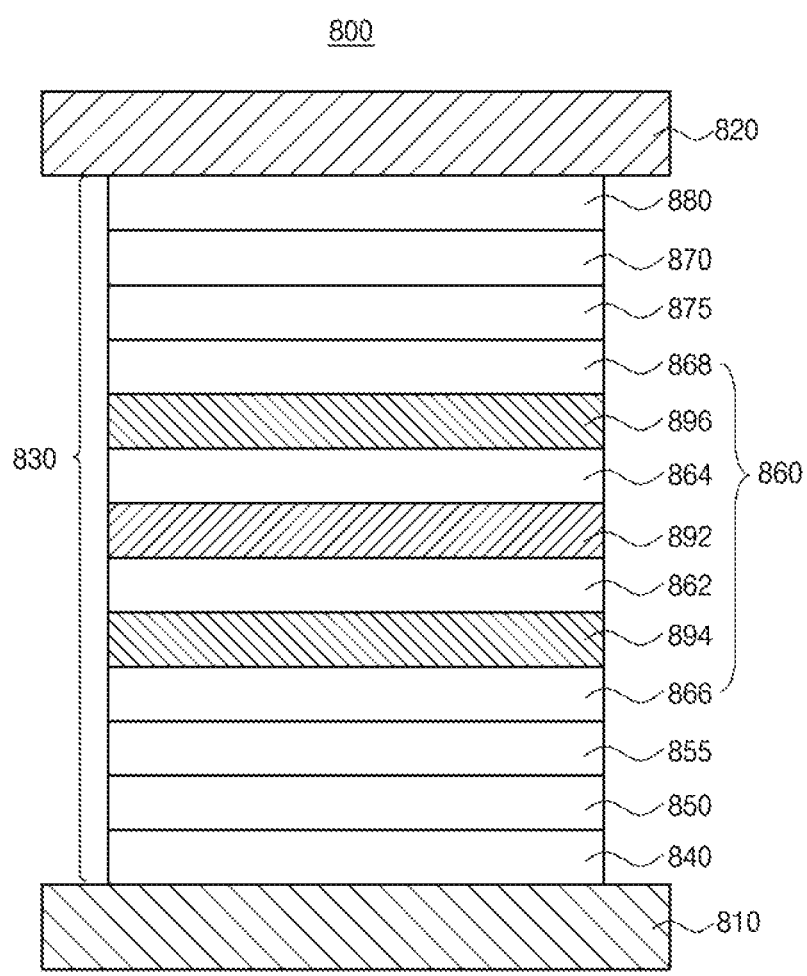
FIG. 17 is a schematic cross-sectional view illustrating an organic light emitting diode in accordance with another exemplary embodiment of the present disclosure.
Figure 18:
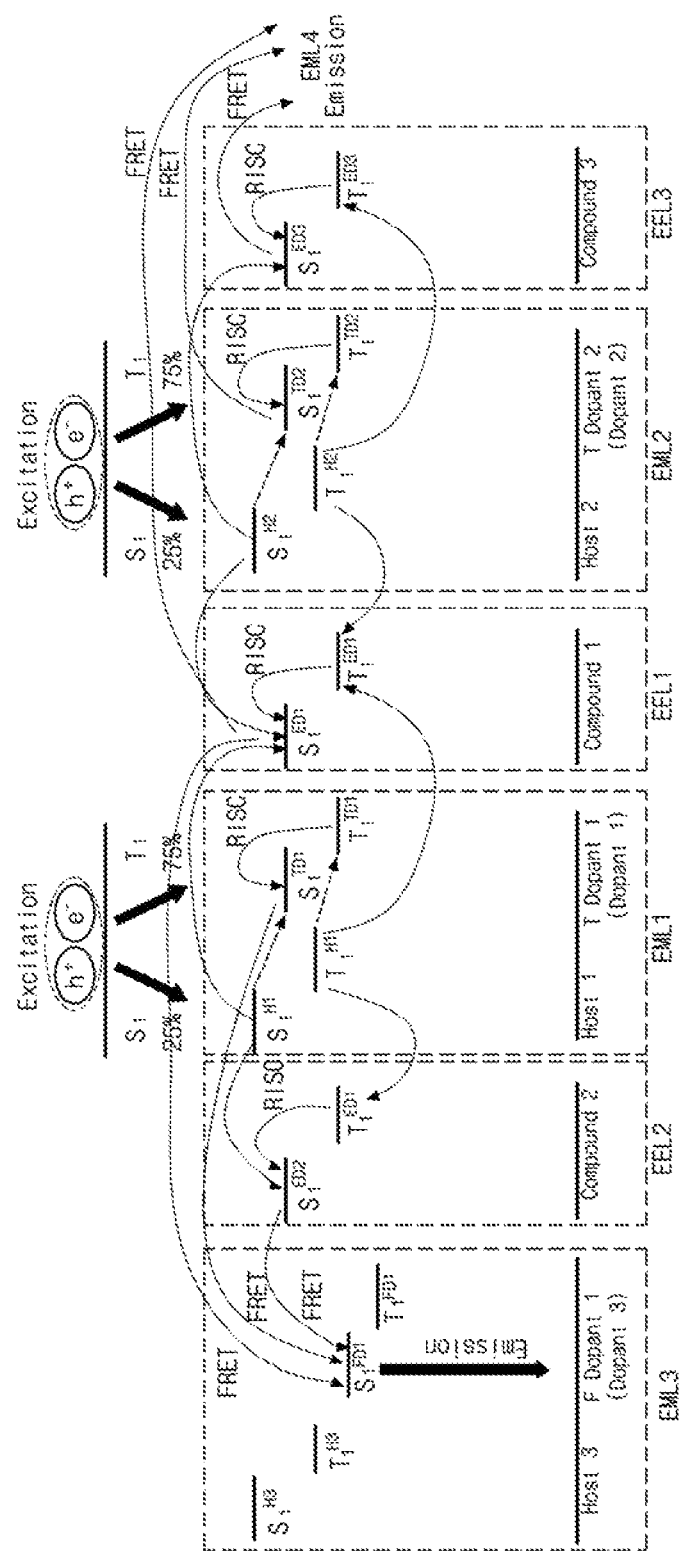
FIG. 18 is a schematic diagram illustrating luminous mechanism by energy level bandgap among luminous materials in accordance with another exemplary embodiment of the present disclosure.

In FIGS. 15 and 16, each of the EML1 762, the EML2 764, the EML3 766 and the EML4 768 includes the first to fourth dopants as the delayed fluorescent material. Unlike those embodiments, EMLs can include different types of dopants. FIG. 17 is a schematic cross-sectional view illustrating an organic light emitting diode in accordance with another exemplary embodiment of the present disclosure. FIG. 18 is a schematic diagram illustrating luminous mechanism by energy level bandgap among luminous materials in accordance with another exemplary embodiment of the present disclosure.

As illustrated in FIG. 17, the OLED 800 in accordance with the eighth embodiment of the present disclosure include first and second electrodes 810 and 820 facing each other and an emitting unit 830 disposed between the first and second electrodes 810 and 820. In one exemplary embodiment, the emitting unit 830 comprises a HIL 840, a HTL 850, an EML 860, an ETL 870 and an EIL 880 each of which is laminated sequentially over the first electrode 810. The emitting unit 830 can further comprise a first exciton blocking layer, i.e. an EBL 855 disposed between the HTL 850 and the EML 860 and/or a second exciton blocking layer, i.e. a HBL 875 disposed between the EML 860 and the ETL 870.

The first and second electrodes 810 and 820, and the emitting unit 830 except the EML 860 can have substantially the same structure and the same material as the first and second electrodes 310, 410, 510, 610, 710, 320, 420, 520, 620 and 720 and the emitting units 330, 330a, 430, 530, 630 and 730 in the above embodiments.

In the exemplary eighth embodiment, the EML 860 includes a first EML (EML1) 862, a second EML (EML2) 864, a third EML (EML3) 866, a first exciton energy control layer (EEL1) 892, a second exciton energy control layer (EEL2) 894 and a third exciton energy control layer (EEL3) 896. Alternatively, the EML 860 can further include a fourth EML (EML4) 868. The EML1 862 includes a first host and a first dopant. The EML2 864 includes a second host and a second dopant and is disposed between the EML1 862 and the HBL 875. The EML3 866 includes a third host and a third dopant and is disposed between the EML1 862 and the EBL 855. The EML4 868 includes a fourth host and a fourth dopant and is disposed between the EML2 864 and the HBL 875. Each of the first and second dopant (T dopant 1 and T dopant 2) is a delayed fluorescent material and each of the third and fourth dopants (F dopant 1 and F dopant 2) is a fluorescent or phosphorescent material.

The EEL1 892 includes a first organic compound and is disposed between the EML1 862 and the EML2 864. The EEL2 894 includes a second organic compound and is disposed between the EML 862 and the EML3 866. The EEL3 896 includes a third organic compound and is disposed between the EML2 864 and the HBL 875. The EEL3 896 can be disposed between the EML2 864 and the EML4 868 when the EML 860 includes the EML4 868. Each of the first to third organic compounds in the EEL1 892, the EEL2 894 and the EEL3 896 is a delayed florescent material, respectively.

Each of the EML1 862 and the EML2 864 includes the first and second dopants as a delayed fluorescent material, respectively. Since the energy level bandgap $\Delta E_{ST}^{TD}$ between each of the excited state triplet energy levels $T_1^{TD1}$ and $T_1^{TD2}$ and each of the excited state singlet energy levels $S_1^{TD1}$ and $S_1^{TD2}$ of the first and second dopants is very low, i.e. equal to or less than about 0.3 eV (See, FIG. 3), each of the exciton energies at the excited state triplet energy levels $T_1^{TD1}$ and $T_1^{TD2}$ of the first and second dopants is converted upwardly to each of the excited state singlet energy levels $S_1^{TD1}$ and $S_1^{TD2}$ by a RISC mechanism.

In addition, since the energy level bandgap $\Delta E_{ST}^{TD}$ between the excited state triplet energy levels $T_1^{ED1}$, $T_1^{ED2}$ and $T_1^{ED3}$ and the excited state singlet energy level $S_1^{ED1}$, $S_1^{ED2}$ and $S_1^{ED3}$ of the first to third organic compounds, each of which is included respectively in the EEL1 892, the EEL2 894 and the EEL3 896, is very low, i.e. equal to or less than about 0.3 eV (See, FIG. 3), each of the exciton energies at the excited state triplet energy levels $T_1^{ED1}$, $T_1^{ED2}$ and $T_1^{ED3}$ of the first to third organic compounds in the EEL1 892, the EEL2 894 and the EEL3 896 is converted to each of the excited state singlet energy levels $S_1^{ED1}$, $S_1^{ED2}$ and $S_1^{ED3}$ by a RISC mechanism. While the first and second dopants and the first to third organic compounds as the delayed fluorescent material show high quantum efficiency, their color purity is poor owing to their wide FWHM.

On the contrary, each of the EML3 866 and the EML4 868 includes the third or fourth host and the third or fourth dopant as the fluorescent or phosphorescent material. While the third and fourth dopants as the fluorescent or phosphorescent material have an advantage in terms of color purity due to narrow FWHM, their quantum efficiencies are limited because their triplet exciton cannot participate in the luminescence process.

However, in this exemplary embodiment, the singlet exciton energies and the triplet exciton energies with respect to each of the first and second dopant, each of which is included in the EML1 862 and the EML2 864 and having the delayed fluorescent property, and the first to third organic compounds, each of which is included in the EEL1 892, the EEL2 894 and the EEL3 896 and has the delayed fluorescent property, can be transferred to the third and fourth dopants, each of which is included in the EML3 866 and the EML4 868 and is a fluorescent or phosphorescent material, by FRET mechanism. Accordingly, the ultimate emission occurs in the third and fourth dopants within the EML3 866 and the EML4 868.

In other words, each of the triplet exciton energies $T_1^{TD1}$, $T_1^{TD2}$, $T_1^{ED1}$, $T_1^{ED2}$ and $T_1^{ED3}$ of the first and second dopants in the EML1 862 and the EML2 864 and the first to third organic compounds in the EEL1 892, the EEL2 894 and the EEL3 896 is converted upwardly to each of the singlet exciton energies $S_1^{TD1}$, $S_1^{TD2}$, $S_1^{ED1}$, $T_1^{ED2}$ and $S_1^{ED3}$ of their own by a RISC mechanism. Since each of the excited state singlet energy levels $S_1^{TD}$, $S_1^{TD2}$, $S_1^{ED1}$, $S_1^{ED2}$ and $S_1^{ED3}$ of the first and second dopants and the first to third organic compounds is higher than each of the excited stat singlet energy levels $S_1^{FD1}$ and $S_1^{FD2}$ of the third and fourth dopants in the EML3 866 and the EML4 868, the converted singlet exciton energies $S_1^{TD}$, $S_1^{TD2}$, $S_1^{ED1}$, $S_1^{ED2}$ and $S_1^{ED3}$ of the first and second dopants and the first to third organic compounds is transferred to each of the singlet energy levels $S_1^{FD1}$ and $S_1^{FD2}$ of the third and fourth dopants. Each of the third and fourth dopants in the EML3 866 and the EML4 868 can emit light using the triplet exciton energy as well as the singlet exciton energy.

As the exciton energy, which is generated at the first and second dopants in the EML1 862 and the EML2 864 and the first to third organic compounds in the EEL1 892, the EEL2 894 and the EEL3 896, is transferred to each of the third and fourth dopants in the EML3 866 and the EML4 868, a hyper-fluorescence can be realized. In this case, the first and second dopants and the first to third organic compounds only act as transferring energy to the third and fourth dopants. Substantial light emission is occurred in the EML3 866 and the EML4 868, each of which includes the third dopant or the fourth dopant as the fluorescent or phosphorescent material and has a narrow FWHM. Accordingly, the OLED 800 can enhance its quantum efficiency and improve its color purity due to narrow FWHM.

Each of the EML1 862, the EML2 864, the EML3 866 and the EML4 868 includes a first host, a second host, a third host and a fourth host, respectively. Each of the exciton energies generated at the first to fourth hosts should be transferred to first and second dopants as the delayed fluorescent material in advance in order to induce light emission. In order to perform such a light emission, each of excited state singlet energy levels $S_1^{H1}$, $S_1^{H2}$, $S_1^{H3}$ and $S_1^{H4}$ and excited state triplet energy levels $T_1^{H1}$, $T_1^{H2}$, $T_1^{H3}$ and $T_1^{H4}$ of the first to fourth hosts should be higher than each of the excited state singlet energy levels $S_1^{TD1}$, $S_1^{TD2}$, $S_1^{ED1}$, $S_1^{ED2}$ and $S_1^{ED3}$ and the excited state triplet energy levels $T_1^{TD1}$, $T_1^{TD2}$, $T_1^{ED1}$, $T_1^{ED2}$ and $T_1^{ED3}$ of the first and second dopants and the first to third organic compounds as the delayed fluorescent material, respectively. As an example, each of the excited state triplet energy levels $T_1^{H1}$, $T_1^{H2}$, $T_1^{H3}$ and $T_1^{H4}$ of the first to fourth hosts can be higher than each of the excited state triplet energy levels $T_1^{TD1}$, $T_1^{TD2}$, $T_1^{ED1}$, $T_1^{ED2}$ and $T_1^{ED3}$ of the first and second dopants and the first to third organic compounds by at least about 0.2 eV.

Moreover, each of the excited state singlet energy levels $S_1^{H3}$ and $S_1^{H4}$ of the third and fourth hosts is higher than each of excited state singlet energy levels $S_1^{FD1}$ and $S_1^{FD2}$ of the third and fourth dopants, respectively. In this case, each of the singlet exciton energies generated at the third and fourth hosts can be transferred to each of the excited singlet energy levels $S_1^{FD1}$ and $S_1^{FD2}$ of the third and fourth dopants.

Moreover, it is necessary for the EML 860 to implement high luminous efficiency and color purity as well as to transfer exciton energy efficiently from the first and second dopants and the first to third organic compounds, each of which is converted to ICT complex state by a RISC mechanism, in the EML1 862, the EML2 864, EEL1 892, EEL2 894 and the EEL3 896 to the third and fourth dopants, each of which is the fluorescent or phosphorescent material in the EML3 866 and the EML4 868. In order to realize such an OLED 800, each of the excited state triplet energy levels $T_1^{TD1}$, $T_1^{TD2}$, $T_1^{ED1}$, $T_1^{ED2}$ and $T_1^{ED3}$ of the first and second dopants and the first to third organic compounds, each of which is included in the EML1 862, the EML2 864, the EEL1 892, the EEL2 894 and the EEL3 896, is higher than each of excited state triplet energy levels $T_1^{FD1}$ and $T_1^{FD2}$ of the third and fourth dopants. In one exemplary embodiment, each of the excited state singlet energy levels $S_1^{TD1}$, $S_1^{TD2}$, $S_1^{ED1}$, $S_1^{ED2}$ and $S_1^{ED3}$ of the first and second dopants and the first to third organic compound can be higher than each of excited state singlet energy levels $S_1^{FD1}$ and $S_1^{FD2}$ of the third and fourth dopants as a fluorescent material.

In addition, an energy level bandgap ($|HOMO^{H1}-HOMO^{TD}|$) between HOMO energy levels ($HOMO^{H1}$ and $HOMO^{H2}$) of the first and second hosts and HOMO energy levels ($HOMO^{TD1}$ and $HOMO^{TD2}$) of the first and second dopants, or an energy level bandgap ($|LUMO^{H1}-LUMO^{TD}|$) between LUMO energy levels ($LUMO^{H1}$ and $LUMO^{H2}$) of the first and second hosts and LUMO energy level ($LUMO^{TD1}$ and $LUMO^{TD2}$) of the first and second dopants can be equal to or less than about 0.5 eV. Moreover, an energy level bandgap ($|HOMO^{H}-HOMO^{ED}|$) between HOMO energy levels ($HOMO^{H1}$, $HOMO^{H2}$, $HOMO^{H3}$ and $HOMO^{H4}$) of the first to fourth hosts and HOMO energy levels ($HOMO^{ED1}$, $HOMO^{ED2}$ and $HOMO^{ED3}$) of the first to third organic compounds, or an energy level bandgap ($|LUMO^{H}-LUMO^{ED}|$) between LUMO energy levels ($LUMO^{H1}$, $LUMO^{H2}$, $LUMO^{H3}$ and $LUMO^{H4}$) of the first to fourth hosts and LUMO energy levels ($LUMO^{ED1}$, $LUMO^{ED2}$ and $LUMO^{ED3}$) of the first to third organic compounds can be equal to or less than about 0.2 eV.

Each of the first to third organic compounds, each of which is included in the EEL1 892, EEL2 894 or the EEL3 896, can be the same as or different from each other. As an example, each of the first to third organic compounds can independently include, but are not limited to, any compound having the structure of Chemical Formulae 1 to 3, as described above. Each of the first to third organic compounds can have the delayed fluorescent property.

Each of the first host in the EML1 862, the second host in the EML2 864, the third host in the EML3 866 and the fourth host in the EML4 868 can be the same or different from each other. As an example, each of the first to fourth hosts can independently include, but are not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

In one exemplary embodiment, each of the first and second dopants in the EML1 862 and the EML2 864 can be the same as the first and second organic compounds. In another exemplary embodiment, each of the first and second dopant can independently include, but are not limited to, any one having the structure of Chemical Formula 4. In still another exemplary embodiment, each of the first and second dopants can independently include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

Each of the third and fourth dopants in the EML3 866 and the EML4 868 can have narrow FWHM and have luminous spectrum having large overlapping area with the absorption spectra of each of the first and second dopants and the first to third organic compounds. As an example, each of the third and fourth dopants can independently include, but are not limited to, an organic compound having a quinolino-acridine core such as 5,12-dimethylquinolino[2,3-b]acridine-7,14(5H, 12H)-dione, 12-diethylquinolino[2,3-b]acridine-7,14(5H, 12H)-dione, 5,12-dibutyl-3,10-difluoroquinolino[2,3-b]acridine-7,14(5H, 12H)-dione, 5,12-dibutyl-3,10-bis(trifluoromethyl)quinolino[2,3-b]acridine-7,14(5H, 12H)-dione, 5,12-dibutyl-2,3,9,10-tetrafluoroquinolino[2,3-b]acridine-7,14(5H, 12H)-dione, DCJTB and any metal complexes which can emit light of red, green or blue color.

In one exemplary embodiment, each of the first to fourth hosts in the EML1 862, the EML2 864, the EML3 866 or the EML4 868 can have weight ratio equal to or more than the first to fourth dopants in the same EMLs 862, 864, 866 and 868, respectively. In addition, the weight ratio of each of the first and second dopants in the EML1 862 and the EML2 864 can be larger than each of the weight ratio of the third and fourth dopants in the EML3 866 and the EML4 868. In this case, it is possible to transfer enough energy from each of the first and second dopants in the EML1 862 and the EML2 864 to the third and fourth dopants in the EML3 866 and the EML4 868.

Each of the EML1 862 and the EML2 864 can include each of the first and second dopants of about 1 to about 70% by weight, preferably about 10 to about 50% by weight, and more preferably about 20 to about 50% by weight. Each of the weight ratios of the third and fourth hosts can be larger than each of the weight ratios of the third and fourth dopants in the EML3 866 and the EML4 868. As an example, each of the EML3 866 and the EML4 868 can include the third or fourth host of about 90 to about 99% by weight, and preferably about 95 to about 99% by weight and the third or fourth dopant of about 1 to about 10% by weight, and preferably about 1 to about 5% by weight.

In one embodiment, each of the EML1 862, the EML2 864, the EML3 866 and the EML4 868 can have substantially the same thickness. As an example, each of the EML1 862, the EML2 864, the EML3 866 and the EML4 868 can be laminated with a thickness of, but are not limited to, about 5 nm to about 100 nm, preferably about 10 nm to about 50 nm, and more preferably about 10 nm to about 30 nm.

In still another exemplary embodiment, each of the EML1 862, the EML2 864, the EML3 866 and the EML4 868 can have different thickness. As an example, each of the EML1 862 and the EML2 864 can have a thickness as about 1.5 to about 2.5 times as each of the EML3 866 and the EML4 868.

In this case, each of the EML1 862 and the EML2 864 can be laminated with a thickness of, but are not limited to, about 10 nm to about 100 nm, and preferably about 15 nm to about 50 nm, and each of the EML3 866 and the EML4 868 can be laminated with a thickness of, but are not limited to, about 5 nm to about 50 nm, and preferably about 5 nm to 20 nm. Alternatively, each of the EML3 866 and the EML4 868 can have a thickness as about 1.5 to about 2.5 times as each of the EML1 862 and the EML2 864. In this case, each of the EML3 866 and the EML4 868 can be laminated with a thickness of, but are not limited to, about 10 nm to about 100 nm, and preferably about 15 nm to about 50 nm, and each of the EML1 862 and the EML2 864 can be laminated with a thickness of, but are not limited to, about 5 nm to about 50 nm, and preferably about 5 nm to about 20 nm.

When the EML3 866 is disposed adjacently to the EBL 855 in one exemplary embodiment, the third host, which is included in the EML3 866 together with the third dopant, can be the same material as the EBL 855. In this case, the EML3 866 can have an electron blocking function as well as an emission function. In other words, the EML3 866 can act as a buffer layer for blocking electrons. In one embodiment, the EBL 855 can be omitted where the EML3 866 can be an electron blocking layer as well as an emitting material layer.

When the EML4 868 is disposed adjacently to the HBL 875 in another exemplary embodiment, the fourth host, which is included in the EML4 868 together with the fourth dopant, can be the same material as the HBL 875. In this case, the EML4 868 can have a hole blocking function as well as an emission function. In other words, the EML4 868 can act as a buffer layer for blocking holes. In one embodiment, the HBL 875 can be omitted where the EML4 868 can be a hole blocking layer as well as an emitting material layer.

In still another exemplary embodiment, the third host in the EML3 866 can be the same material as the EBL 855 and the fourth host in the EML4 868 can be the same material as the HBL 875. In this embodiment, the EML3 866 can have an electron blocking function as well as an emission function, and the EML4 868 can have a hole blocking function as well as an emission function. In other words, each of the EML3 866 and the EML4 868 can act as a buffer layer for blocking electrons or hole, respectively. In one embodiment, the EBL 855 and the HBL 875 can be omitted where the EML3 866 can be an electron blocking layer as well as an emitting material layer and the EML4 868 can be a hole blocking layer as well as an emitting material layer.

Figure 19:
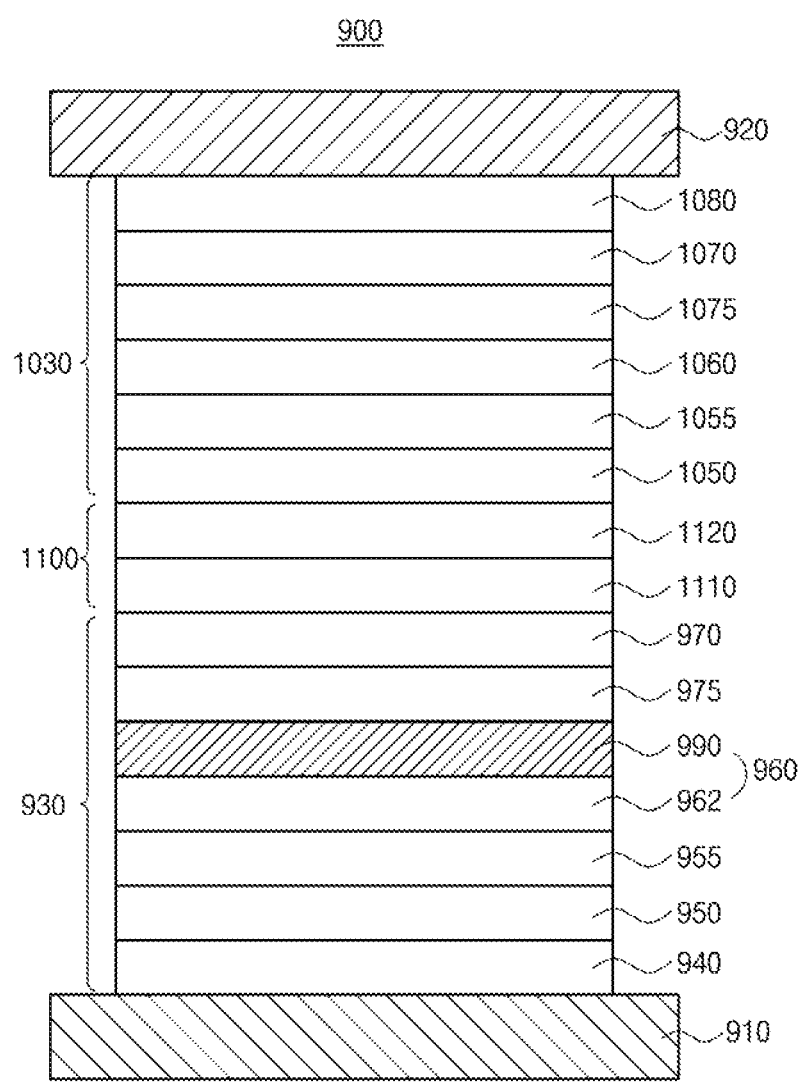
FIG. 19 is a schematic cross-section view illustrating an organic light emitting diode in accordance with another exemplary embodiment of the present disclosure.

In the above embodiments, the OLED having only one emitting unit is described. Unlike the above embodiment, the OLED can have multiple emitting units so as to form a tandem structure. FIG. 19 is a schematic cross-section view illustrating an organic light emitting diode in accordance with another exemplary embodiment of the present disclosure.

As illustrated in FIG. 19, the OLED 900 in accordance with the ninth embodiment of the present disclosure includes first and second electrodes 910 and 920 facing each other, a first emitting unit 930 as a first emission layer disposed between the first and second electrodes 910 and 920, a second emitting unit 1030 as a second emission layer disposed between the first emitting unit 930 and the second electrode 920, and a charge generation layer 1100 disposed between the first and second emitting units 930 and 1030.

As mentioned above, the first electrode 910 can be an anode and include, but are not limited to, a conductive material, for example, a transparent conductive material (TCO), having a relatively large work function values. As an example, the first electrode 910 can include, but are not limited to, ITO, IZO, SnO, ZnO, ICO, AZO, and the likes. The second electrode 920 can be a cathode and can include, but are not limited to, a conductive material having a relatively small work function values such as Al, Mg, Ca, Ag, alloy thereof or combination thereof.

The first emitting unit 930 includes a HIL 940, a first HTL (a lower HTL) 950, a lower EML 960 and a first ETL (a lower ETL) 970. The first emitting unit 930 can further include a first EBL (a lower EBL) 955 disposed between the first HTL 950 and the lower EML 960 and/or a first HBL (a lower HBL) 975 disposed between the lower EML 960 and the first ETL 970.

The second emitting unit 1030 includes a second HTL (an upper HTL) 1050, an upper EML 1060, a second ETL (an upper ETL) 1070 and an EIL 1080. The second emitting unit 1030 can further include a second EBL (an upper EBL) 1055 disposed between the second HTL 1050 and the upper EML 1060 and/or a second HBL (an upper HBL) 1075 disposed between the upper EML 1060 and the second ETL 1070.

At least one of the lower EML 960 and the upper EML 1060 can include at least one exciton energy control layer disposed adjacently at least one emitting material layer that includes a host and a dopant. Hereinafter, the OLED 900, where the lower EML 960 includes at least one exciton control layer, will be explained.

The HIL 940 is disposed between the first electrode 910 and the first HTL 950 and improves an interface property between the inorganic first electrode 910 and the organic first HTL 950. In one exemplary embodiment, the HIL 940 can include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 940 can be omitted in compliance with a structure of the OLED 900.

Each of the first and second HTLs 950 and 1050 can independently include, but are not limited to, TPD, NPD (NPB), CBP, poly-TPD, TFB, TAPC, DCDPA, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine. Each of the HIL 940 and the first and second HTLs 950 and 1050 can be laminated with a thickness of, but are not limited to, about 5 to about 200 nm, and preferably about 5 to about 100 nm.

Each of the first and second ETLs 970 and 1070 facilitates electron transportations in the first emitting unit 930 and the second emitting unit 1030, respectively. Each of the first and second ETLs 970 and 1070 can independently include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes, respectively. As an example, each of the first and second ETLs 970 and 1070 can independently include, but are not limited to, $Alq_3$, PBD, spiro-PBD, Liq, TPBi, BAlq, Bphen, NBphen, BCP, TAZ, NTAZ, TpPyPB, TmPPPyTz, PFNBr, TPQ, TSPO1 and/or 2-[4-(9,10-di-2-naphthalenyl-2-anthracenyl)phenyl]-1-phenyl-1H-benzimidazole, respectively.

The EIL 1080 is disposed between the second electrode 920 and the second ETL 1070, and can improve physical properties of the second electrode 920 and therefore, can enhance the life span of the OLED 900. In one exemplary embodiment, the EIL 1080 can include, but are not limited to, an alkali halide such as LiF, CsF, NaF, $BaF_2$ and the likes, and/or an organic metal compound such as lithium benzoate, sodium stearate, and the likes.

Each of the first and second EBLs 955 and 1055 can independently include, but are not limited to, TCTA, Tris [4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, DCDPA, 2,8-bis(9-phenyl-9H-carbazol-3-yl)dibenzo[b,d]thiophene and/or 3,6-bis(N-carbazolyl)-N-phenyl-carbazole, respectively.

Each of the first and second HBLs 975 and 1075 can independently include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, each of the first and second HBLs 975 and 1075 can independently include, but are not limited to, BCP, BAlq, Alq$_3$, PBD, spiro-PBD, Liq, B3PYMPM, DPEPO, TSPO1, 9-(6-(9H-carbazol-9-yl)pyridine-3-yl)-9H-3,9'-bicarbazole and combination thereof, respectively.

In one exemplary embodiment, when the upper EML 1060 emits red light, the upper EML 1060 can be, but are not limited to, a phosphorescent material layer including a host such as CBP and the likes and at least one dopant selected from the group consisting of PIQIr(acac)(bis(1-phenylisoquinoline)acetylacetonate iridium), PQIr(acac) (bis(1-phenylquinoline)acetylacetonate iridium), PQIr (tris(1-phenylquinoline)iridium) and PtOEP (octaethylporphyrin platinum). Alternatively, the upper EML 1060 can be a fluorescent material layer including PBD:Eu(DMB)3(phen), perylene and/or their derivatives. In this case, the upper EML 1060 can emit red light having, but is not limited to, emission wavelength ranges of about 600 nm to about 650 nm.

In another exemplary embodiment, when the upper EML 1060 emits blue light, the upper EML 1060 can be, but are not limited to, a phosphorescent material layer including a host such as CBP and the likes and at least one iridium-based dopant. Alternatively, the upper EML 1060 can be a fluorescent material layer including any one selected from the group consisting of spiro-DPVBi, spiro-CBP, distrylbenzene (DSB), distrylarylene (DSA), PFO-based polymers and PPV-based polymers. The upper EML 1060 can emit light of sky-blue color or deep blue color as well as blue color. In this case, the upper EML 1060 can emit blue light having, but are not limited to, emission wavelength ranges of about 440 nm to about 480 nm.

In one exemplary embodiment, the second emitting unit 1030 can have double-layered EML 1060, for example, a blue emitting material layer and a red emitting material layer, in order to enhance luminous efficiency of the red light. In this case, the upper EML 1060 can emit light having, but are not limited to, emission wavelength ranges of about 440 nm to about 650 nm.

The charge generation layer (CGL) 1100 is disposed between the first emitting unit 930 and the second emitting unit 1030. The CGL 1100 includes an N-type CGL 1110 disposed adjacently to the first emitting unit 930 and a P-type CGL 1120 disposed adjacently to the second emitting unit 1030. The N-type CGL 1110 injects electrons into the first emitting unit 930 and the P-type CGL 1120 injects holes into the second emitting unit 1030.

As an example, the N-type CGL 1110 can be a layer doped with an alkali metal such as Li, Na, K and/or Cs and/or an alkaline earth metal such as Mg, Sr, Ba and/or Ra. For example, a host used in the N-type CGL 1110 can include, but not limited to, an organic compound such as Bphen or MTDATA. The alkali metal or the alkaline earth metal can be doped by about 0.01 wt % to about 30 wt %.

The P-type CGL 1120 can include, but are not limited to, an inorganic material selected from the group consisting of tungsten oxide (WO$_x$), molybdenum oxide (MoO$_x$), beryllium oxide (Be$_2$O$_3$), vanadium oxide (V$_2$O$_5$) and combination thereof, and/or an organic material selected from the group consisting of NPD, HAT-CN, 2,3,5,6-Tetrafluoro-7,7,8,8-tetracyanoquinodimethane (F4TCNQ), TPD, N,N,N',N'-Tetranaphthalenyl-benzidine (TNB), TCTA, N,N'-dioctyl-3,4,9,10-perylenedicarboximide (PTCDI-C8) and combination thereof.

In one exemplary embodiment, the lower EML 960 includes a first EML (EML1) 962 and an exciton energy control layer (EEL) 990 disposed adjacently to the EML1 962. The EML1 962 includes a host and a dopant and the EEL 990 includes an organic compound. The EEL 990 can be disposed between the first EBL 955 and the EML1 962 or between the EML1 962 and the first HBL 975. In one embodiment, each of the dopant and the organic compound can be a delayed fluorescent material, respectively.

Each of an excited state singlet energy level $S_1^H$ and an excited state triplet energy level $T_1^H$ of the host in the EML1 962 is higher than each of an excited state singlet energy level $S_1^{TD}$ and an excited state triplet energy level $T_1^{TD}$ of the dopant in the same EML 962. In addition, each of the excited state singlet energy level $S_1^H$ and the excited state triplet energy level $T_1^H$ of the host in the EML1 962 is higher than each of an excited state singlet energy level $S_1^{ED}$ and an excited state triplet energy level $T_1^{ED}$ of the organic compound in the EEL 990 (See, FIG. 5).

It is preferable that an energy level bandgap ($|HOMO^H - HOMO^{TD}|$) between a HOMO energy level ($HOMO^H$) of the host and a HOMO energy level ($HOMO^{TD}$) of the dopant, or an energy level bandgap ($|LUMO^H - LUMO^{TD}|$) between a LUMO energy level ($LUMO^H$) of the host and a LUMO energy level ($LUMO^{TD}$) of the dopant can be equal to or less than about 0.5 eV, for example, between about 0.1 eV to about 0.5 eV. Moreover, an energy level bandgap ($|HOMO^H - HOMO^{ED}|$) between a HOMO energy level ($HOMO^H$) of the host and a HOMO energy level ($HOMO^{ED}$) of the organic compound, or an energy level bandgap ($|LUMO^H - LUMO^{ED}|$) between a LUMO energy level ($LUMO^H$) of the host and a LUMO energy level ($LUMO^{ED}$) of the organic compound can be equal to or less than about 0.2 eV.

Each of exciton energy at the excited state singlet energy level $S_1^H$ and exciton energy at the excited state triplet energy level $T_1^H$ of the host is transferred to each of the excited state singlet energy level $S_1^{TD}$ and the excited state triplet energy level $T_1^{TD}$ of the first dopant as the delayed fluorescent material in the same EML by Dexter energy transfer mechanism, which transfer exciton energies depending upon wave function overlaps among adjacent molecules by inter-molecular electron exchanges and exciton diffusions, respectively. The exciton energy at the excited state triplet energy level $T_1^{TD}$ of the dopant as the delayed fluorescent material is converted upwardly to the excited state singlet energy level $S_1^{TD}$ by RISC mechanism, and then the converted exciton energy at the excited state singlet energy level $S_1^{TD}$ is transferred to the ground state as a delayed fluorescence.

A part of exciton energy, accumulated at the excited state singlet energy level $S_1^H$ and the excited state triplet energy level $T_1^H$ of the host without being transferred to the dopant in the EML1 962, can be transferred to an excited state singlet energy level $S_1^{ED}$ and an excited state triplet energy level $T_1^{ED}$ of the organic compound in the EEL 990 which is disposed adjacently to the EML1 962 by a FRET (Forster resonance energy transfer) mechanism, which transfers energy non-radially through electrical fields by dipole-dipole interactions. As a part of exciton energy of the host, which is not transferred to the dopant, is transferred to the organic compound, the exciton energy of the host without being transferred to the dopant is not accumulated at the host. As a result, exciton quenching caused by interaction between the accumulated host excitons and the peripheral polaron can be minimized and lifetime reduction of the OLED 900 owing to the electro-oxidation and the photo-oxidation in the course of exciton quenching can be prevented.

As an example, the EEL 990 can be laminated with a thickness of, but are not limited to, about 1 to about 10 nm, and preferably about 1 to about 5 nm. As an example, the organic compound in the EEL 990 disposed adjacently to the EML1 962 can be a delayed fluorescent material in order to implement efficient luminescence. In this case, the organic compound can enhance its luminous efficiency because it can utilize the triplet exciton energy as well as the singlet exciton energy derived from the host in emitting light.

As an example, the host can include, but are not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl)dibenzo[b,d]thiophene, 9-(4-(9H-carbazol-9-yl)phenyl)-9H-3,9-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

In one exemplary embodiment, the dopant in the EML1 962 can be the same as the organic compound. In another exemplary embodiment, the dopant can include, but are not limited to, any one having the structure of Chemical Formula 4. In still another exemplary embodiment, the dopant can include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

When the EML1 962 includes the host and the dopant, the EML1 962 can include the dopant of about 1 to 70% by weight, preferably about 10 to about 50% by weight, and more preferably about 20 to about 50% by weight.

In one embodiment, the EEL 990 can be laminated with a thickness of, but are not limited to, about 1 nm to 10 nm, and preferably about 1 nm to about 5 nm. The EML1 962 can be laminated with a thickness of, but are not limited to, about 10 nm to about 200 nm, preferably about 20 nm to about 100 nm, and more preferably about 20 nm to about 50 nm.

In an alternative embodiment, the lower EML 960 can have any one structure of the EMLs 360a, 460, 560, 660, 760 and 860 as illustrated in FIGS. 5, 7, 11, 13, 15 and 17. In still another exemplary embodiment, an OLED of the present disclosure can further includes a third emitting unit disposed between the second emitting unit 1030 and the second electrode 920 and a second CGL disposed between the second emitting unit 1030 and the third emitting unit. In this case, at least one of the first emitting unit 930, the second emitting unit 1030 and the third emitting unit can include at least one exciton energy control layer disposed adjacently to at least one emitting material layer, as described above.

Example 1: Fabrication of Organic Light Emitting Diode (OLED)

An organic light emitting diode was fabricated applying an exciton energy control layer (EEL) in an emitting material layer. An ITO (including reflective layer) attached glass substrate with 40 nm×40 nm×0.5 nm was ultrasonically cleaned with isopropyl alcohol, acetone and distilled water for 5 minutes and then dried in an oven at 100° C. The cleaned substrate was treated with $O_2$ plasma in a vacuum for 2 minutes and transferred to a deposition chamber in order to deposit other layers on the substrate. An organic layer was deposited by evaporation by a heated boat under $10^{-7}$ torr in the following order. The deposition rate of the organic layer was set to 1 Å/s.

A hole injection layer (HIL) (HAT-CN; 50 Å); a hole transport layer (HTL) (NPB, 500~1500 Å); an electron blocking layer (EBL) (TCTA; 50 Å); a first emitting material layer (EML1) (MADN (host): Compound 1 in Chemical Formula 3 (dopant)=70:30; 60 Å); exciton energy control layer (EEL) (Compound 1; 10 to 20 Å); a second emitting material layer (EML2) (MADN (host): Compound 1 in Chemical Formula 3 (dopant)=70:30; 200 Å); an electron transport layer (ETL) (2-[4-(9,10-di-2-naphthalenyl-2-anthracenyl)phenyl]-1-phenyl-1H-benzimidazole; 300 Å); an electron injection layer (EIL) (LiF; 10 Å); and a cathode (Al; 800~1000 Å).

And then, capping layer (CPL) was deposited over the cathode and the device was encapsulated by glass. After deposition of emissive layer and the cathode, the OLED was transferred from the deposition chamber to a dry box for film formation, followed by encapsulation using UV-curable epoxy resin and moisture getter. The manufacture organic light emitting diode had an emission area of 9 $mm^2$.

Examples 2~3: Fabrication of OLED

An OLED was fabricated using the same materials as Example 1, except laminating the EML1 and the EML2 each with a thickness of 130 Å (Example 2) or laminating the EML1 with a thickness of 200 Å and the EML2 with a thickness of 60 Å (Example 3).

Examples 4: Fabrication of OLED

An OLED was fabricated using the same materials as Example 1, except laminating sequentially the EML1 (MADN (host): Compound 1 in Chemical Formula 3 (dopant)=70:30; 60 Å), a first exciton energy control layer (EEL1) (Compound 1; 10 to 20 Å), the EML2 (MADN (host): Compound 1 in Chemical Formula 3 (dopant)=70:30; 70 Å), a second EEL (EEL2 (Compound 1; 10 to 20 Å), a third EML (EML3) (MADN (host): Compound 1 in Chemical Formula 3 (dopant)=70:30; 130 Å) between the EBL and the ETL.

Examples 5: Fabrication of OLED

An OLED was fabricated using the same materials as Example 4, except laminating the EML2 with a thickness of 140 Å and the EML3 with a thickness of 60 Å.

Examples 6: Fabrication of OLED

An OLED was fabricated using the same materials as Example 4, except laminating the EML2 with a thickness of 130 Å and the EML3 with a thickness of 60 Å.

Examples 7: Fabrication of OLED

An OLED was fabricated using the same materials as Example 1, except laminating the EML1 (MADN (host): Compound 1 in Chemical Formula 3 (dopant)=70:30; 60 Å), the EEL 1 (Compound 1; 10 to 20 Å), the EML2 (MADN (host): Compound 1 in Chemical Formula 3 (dopant)=70:30; 70 Å), the EEL2 (Compound 1; 10 to 20 Å), the EML3 (MADN(host): Compound 1 in Chemical Formula 3 (dopant)=70:30; 70 Å), a third EEL (EEL3) (Compound 1; 10 to 20 Å), a fourth EML (EML4) (MADN (host): Compound 1 in Chemical Formula 3 (dopant)=70:30; 60 Å) between the EBL and the ETL.

Comparative Example: Fabrication of OLED

An OLED was fabricated using the same materials as Example 1, except a single layered EML (MADN (host): Compound 1 in Chemical Formula 3 (dopant)=70:30; 300 Å) without any EELs (Ref.).

Experimental Example 1: Measurement of Luminous Properties of OLED

Each of the organic light emitting diode fabricated by Examples 1 to 7 and Comparative Example was connected to an external power source and then luminous properties for all the diodes were evaluated using a constant current source (KEITHLEY) and a photometer PR650 at room temperature. In particular, driving voltage (V), Power Efficiency (lm/W), External Quantum Efficiency (EQE, %), CIE color coordinates and luminous lifetime ($T_{95}$) at a current density of 10 mA/cm$^2$ of the light emitting diodes of Examples 1 to 7 and Comparative Example were measured. The results thereof are shown in the following Table 1.

TABLE 1

| Luminous Properties of OLED | | | | |
| --- | --- | --- | --- | --- |
| Sample | V | lm/W | EQE (%) | CIEx, CIEy | $T_{95}$ (relative) |
| Ref. | 4.5 | 5.4 | 6.1 | 0.156, 0.185 | 1 |
| Example 1 | 4.5 | 11.7 | 11.9 | 0.156, 0.180 | 2.7 |
| Example 2 | 4.5 | 11.2 | 11.5 | 0.159, 0.191 | 2.5 |
| Example 3 | 4.4 | 11.3 | 11.2 | 0.162, 0.198 | 2.4 |
| Example 4 | 4.5 | 12.4 | 12.6 | 0.159, 0.192 | 2.9 |
| Example 5 | 4.4 | 12.4 | 12.3 | 0.161, 0.197 | 2.7 |
| Example 6 | 4.4 | 12.3 | 12.2 | 0.162, 0.198 | 2.2 |
| Example 7 | 4.6 | 11.9 | 12.3 | 0.163, 0.217 | 2.7 |

As indicated in Table 1, compared with the OLED without forming any exciton energy control layer in the Comparative Example, the OLED including at least one exciton energy control layer enhanced its Power Efficiency up to 129.6%, its EQE up to 106.6% and its luminous lifetime up to 2.9 times.

Examples 8~14: Fabrication of OLED

An OLED was fabricated using the same materials as Examples 1 to 7, except using the Compound 2 in Chemical Formula 3 in place of the Compound 1 as the dopant in the EMLs and the material of the EELs. Each of Examples 8 to 14 corresponds to each of Examples 1 to 7, respectively.

Experimental Example 2: Measurement of Luminous Properties of OLED

Luminous properties with regard to the OLEDs in Example 8 to 14 and Comparative Example were evaluated as the same process in the Experimental Example 1. The results thereof are shown in the following Table 2.

TABLE 2

| Luminous Properties of OLED | | | | |
| --- | --- | --- | --- | --- |
| Sample | V | lm/W | EQE (%) | CIEx, CIEy | $T_{95}$ (relative) |
| Ref. | 4.5 | 5.4 | 6.1 | 0.156, 0.185 | 1 |
| Example 8 | 4.7 | 11.5 | 12.9 | 0.158, 0.211 | 3.2 |
| Example 9 | 4.7 | 11.9 | 12.5 | 0.159, 0.213 | 3.1 |
| Example 10 | 4.6 | 11.2 | 12.1 | 0.162, 0.219 | 2.9 |
| Example 11 | 4.6 | 13.1 | 13.3 | 0.158, 0.214 | 3.1 |
| Example 12 | 4.5 | 13.4 | 12.9 | 0.161, 0.218 | 3.0 |

TABLE 2-continued

| Luminous Properties of OLED | | | | |
| --- | --- | --- | --- | --- |
| Sample | V | lm/W | EQE (%) | CIEx, CIEy | $T_{95}$ (relative) |
| Example 13 | 4.5 | 12.9 | 13.3 | 0.162, 0.229 | 2.5 |
| Example 14 | 4.8 | 12.1 | 13.0 | 0.163, 0.235 | 2.9 |

As indicated in Table 2, compared with the OLED without forming any exciton energy control layer in the Comparative Example, the OLED including at least one exciton energy control layer enhanced its Power Efficiency up to 148.1%, its EQE up to 118.0% and its luminous lifetime up to 3.2 times. Considering the results in the Experimental Examples 1 and 2, it was confirmed that the luminous efficiency and the luminous lifetime of the OLED can be improved by introducing at least one exciton energy control layer disposed adjacently to at least one emitting material layer. Accordingly, it is possible to implement an organic light emitting device such as an organic light emitting display device and/or an organic light emitting illumination device having enhanced luminous efficiency and luminous lifetime by using an OLED including at least one exciton energy control layer.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic light emitting diode, comprising:
a first electrode;
a second electrode, wherein the first electrode and the second electrode face each other; and
at least one emitting unit,
wherein the at least one emitting unit is disposed between the first and second electrodes, and comprises an emitting material layer,
wherein the emitting material layer comprises a first emitting material layer including a first host and a first dopant, and a first exciton energy control layer,
wherein the first exciton energy control layer is disposed between the first electrode and the first emitting material layer or disposed between the first emitting material layer and the second electrode, wherein the first exciton energy control layer comprises a first organic compound, wherein each of an excited state singlet energy level and an excited state triplet energy level of the first organic compound is lower than each of an excited state singlet energy level and an excited state triplet energy level of the first host, respectively, and wherein the first dopant comprises a delayed fluorescent material.

2. The organic light emitting diode of claim 1, wherein each of the excited state singlet energy level and the excited state triplet energy level of the first host is higher than each of an excited state singlet energy level and an excited state triplet energy level of the first dopant, respectively.

3. The organic light emitting diode of claim 1, wherein the first dopant comprises the first organic compound.

4. The organic light emitting diode of claim 1, wherein the first organic compound has the following structure of Chemical Formula 1:

Chemical Formula 1

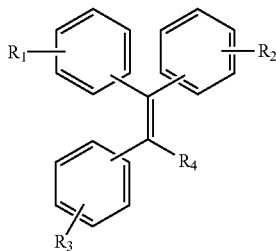

wherein each of $R_1$ to $R_3$ is independently protium, deuterium, tritium, $C_5$~$C_{30}$ aryl group unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group, or $C_4$~$C_{30}$ hetero aryl group unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group; and wherein $R_4$ is protium, deuterium, tritium or phenyl group unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group.

5. The organic light emitting diode of claim 1, wherein the first organic compound includes an organic compound having the following structure of Chemical Formula 2:

Chemical Formula 2

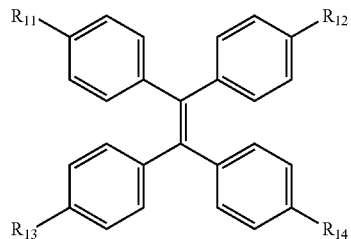

wherein each of $R_{11}$ to $R_{14}$ is independently protium, deuterium, tritium or aryl or hetero aryl group selected from the group consisting of phenyl, pyridyl, carbazolyl, acridinyl, phenazinyl, phenoxazinyl, dibenzofuranyl, dibenzothiophenyl, diazinyl and triazinyl, each of which is unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group, wherein at least two of $R_{11}$ to $R_{14}$ is the aryl or hetero aryl group, wherein at least one of $R_{11}$ to $R_{14}$ is pyridyl, diazinyl or triazinyl and other of $R_{11}$ to $R_{14}$ is phenyl, carbazolyl, acridinyl, phenazinyl, phenoxazinyl, dibenzofuranyl or dibenzothiophenyl.

6. The organic light emitting diode of claim 1, wherein the first organic compound has any one of the following structures of Chemical Formula 3:

Chemical Formula 3

Compound 1

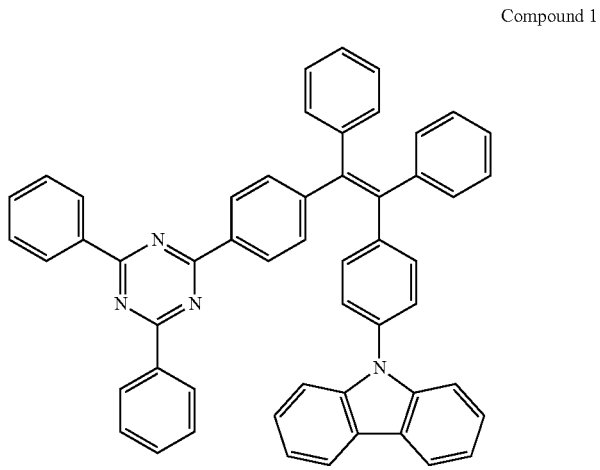

Compound 2

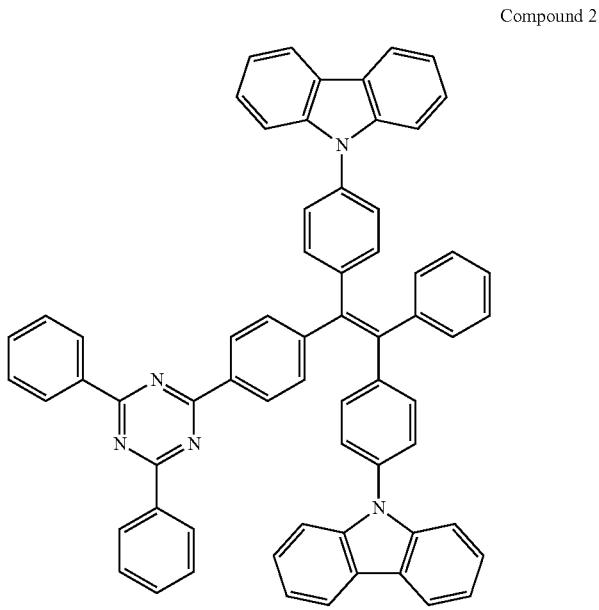

Compound 3
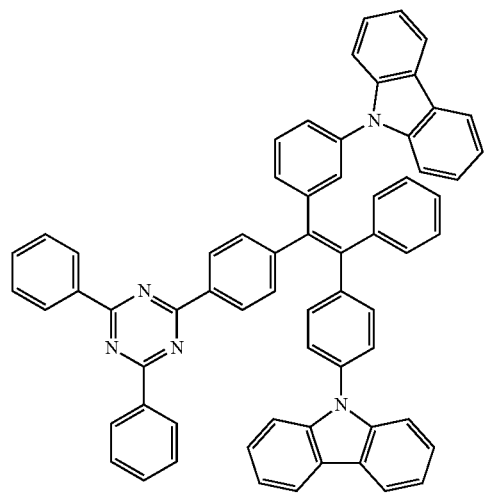
Compound 4
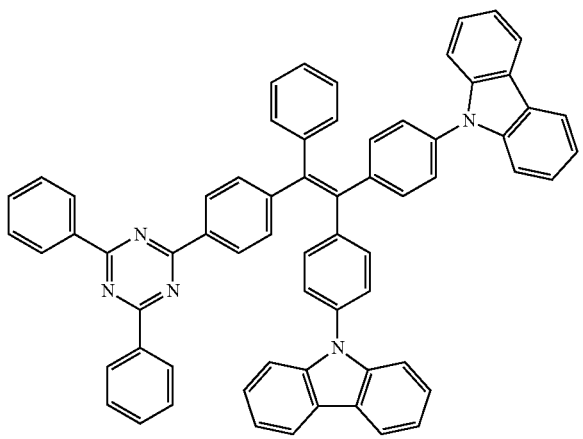
Compound 5
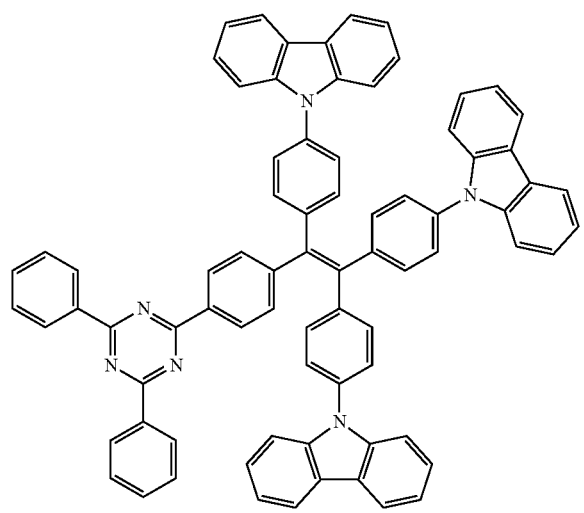
Compound 6
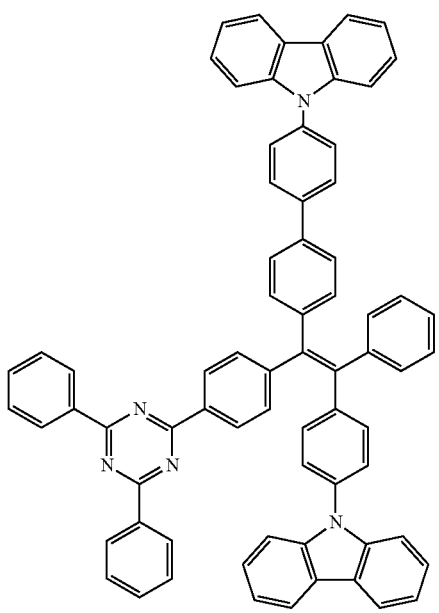

Compound 7
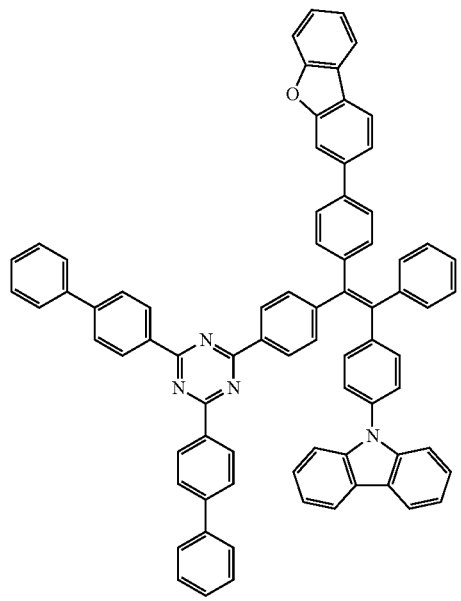
Compound 8
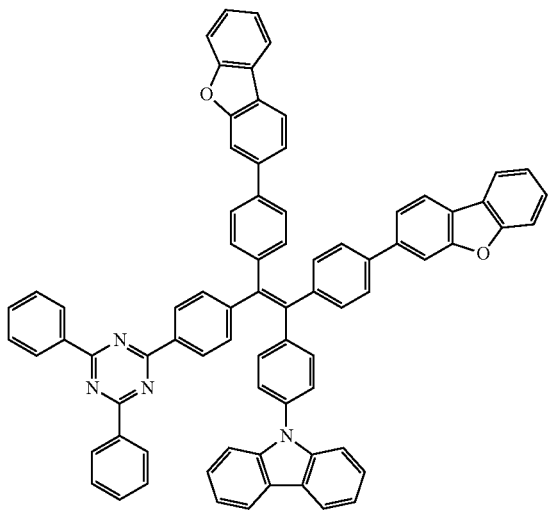
Compound 9
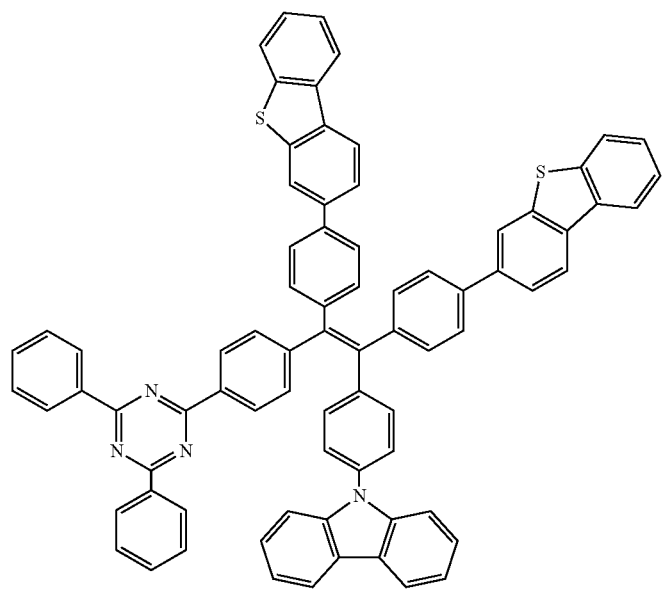

Compound 10
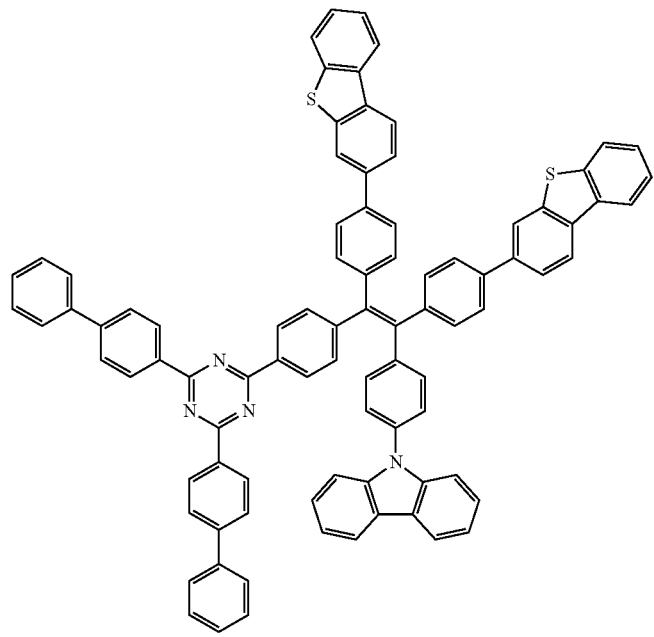
Compound 11
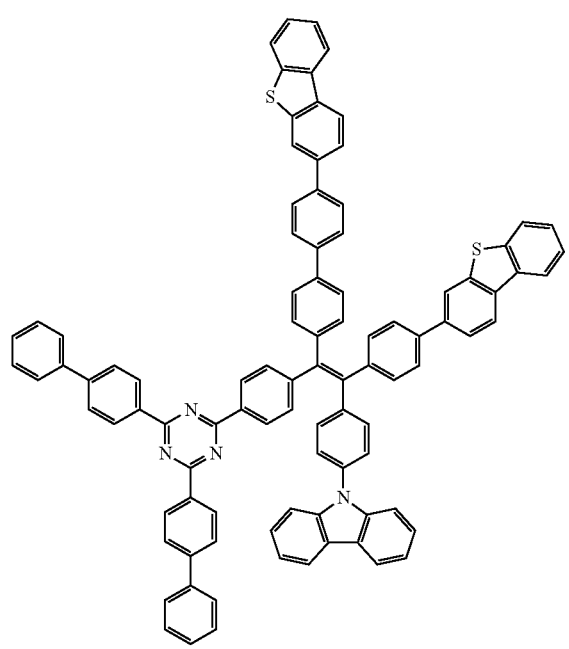

Compound 12

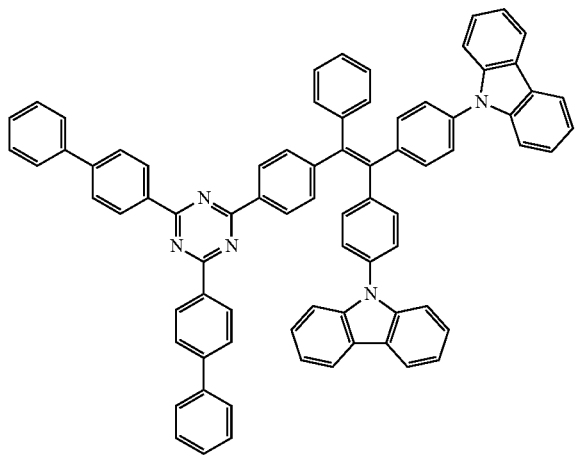

Compound 13

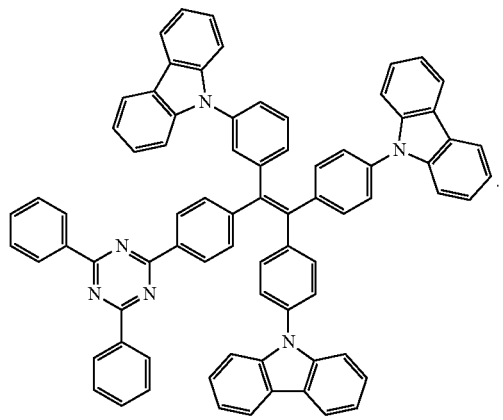

7. The organic light emitting diode of claim 1, wherein each of the first dopant and the first organic compound comprises a delayed fluorescent material.

8. The organic light emitting diode of claim 1, wherein the first emitting material layer further comprises a second dopant,
wherein an excited state triplet energy level of the first dopant is lower than the excited state triplet energy level of the first host, and
wherein an excited state singlet energy level of the first dopant is higher than an excited state singlet energy level of the second dopant.

9. The organic light emitting diode of claim 8, wherein the excited state singlet energy level of the first organic compound is higher than the excited state singlet energy level of the second dopant.

10. The organic light emitting diode of claim 1, wherein the emitting material layer further comprises a second emitting material layer disposed opposite to the first emitting material layer with respect to the first exciton energy control layer, wherein the second emitting material layer comprises a second host and a second dopant.

11. The organic light emitting diode of claim 10, wherein each of excited state singlet energy levels and excited state triplet energy levels of the first and second hosts is higher than each of the excited state singlet energy level and the excited state triplet energy level of the first organic compound, respectively.

12. The organic light emitting diode of claim 10, wherein each of the first and second dopant includes a delayed fluorescent material.

13. The organic light emitting diode of claim 10, wherein each of the excited state singlet energy level and the excited state triplet energy level of the first host is higher than each of an excited state singlet energy level and an excited state triplet energy level of the first dopant, respectively, and wherein each of an excited state singlet energy level and an excited state triplet energy level of the second host is higher than each of an excited state singlet energy level and an excited state triplet energy level of the second dopant, respectively.

14. The organic light emitting diode of claim 10, wherein an excited state singlet energy level of the first dopant is higher than an excited state singlet energy level of the second dopant.

15. The organic light emitting diode of claim 10, wherein the excited state singlet energy level of the first organic compound is higher than an excited state singlet energy level of the second dopant.

16. The organic light emitting diode of claim 10, wherein the second emitting material layer is disposed between the first exciton energy control layer and the second electrode, and wherein the emitting material layer further comprises a second exciton energy control layer disposed between the second emitting material layer and the second electrode.

17. The organic light emitting diode of claim 16, wherein the second exciton energy control layer includes a second organic compound, and wherein each of an excited state singlet energy level and an excited state triplet energy level of the second organic compound is lower than each of excited state singlet energy levels and excited state triplet energy levels of the first and second hosts, respectively.

18. The organic light emitting diode of claim 16, wherein the emitting material layer further comprises a third emitting material layer disposed between the second exciton energy control layer and the second electrode, and wherein the third emitting material layer includes a third host and a third dopant.

19. The organic light emitting diode of claim 18, wherein the second exciton energy control layer includes a second organic compound, and wherein each of an excited state singlet energy level and an excited state triplet energy level of the second organic compound is lower than each of excited state singlet energy levels and excited state triplet energy levels of the first to third hosts, respectively.

20. The organic light emitting diode of claim 18, wherein each of the first to third dopants includes a delayed fluorescent material.

21. The organic light emitting diode of claim 18, wherein the emitting material layer further comprises a third exciton energy control layer disposed between the third emitting material layer and the second electrode.

22. The organic light emitting diode of claim 21, wherein the third exciton energy control layer includes a third organic compound, and wherein each of an excited state singlet energy level and an excited state triplet energy level of the third organic compound is lower than each of excited state singlet energy levels and excited state triplet energy levels of the first to third hosts, respectively.

23. The organic light emitting diode of claim 21, wherein the emitting material layer further comprises a fourth emitting material layer disposed between the third exciton energy control layer and the second electrode, and wherein the fourth emitting material layer includes a fourth host and a fourth dopant.

24. The organic light emitting diode of claim 23, wherein the third exciton energy control layer includes a third organic compound, and wherein each of an excited state singlet energy level and an excited state triplet energy level of the third organic compound is lower than each of excited state singlet energy levels and excited state triplet energy levels of the first to fourth hosts, respectively.

25. The organic light emitting diode of claim 24, wherein each of the first to fourth dopants includes a delayed fluorescent material.

26. The organic light emitting diode of claim 10, wherein the first emitting material layer is disposed between the first electrode and the first exciton energy control layer, and wherein the emitting material layer further comprises a second exciton energy control layer disposed between the second emitting material layer and the second electrode.

27. The organic light emitting diode of claim 26, wherein the second exciton energy control layer includes a second organic compound, and wherein each of an excited state singlet energy level and an excited state triplet energy level of the second organic compound is lower than each of excited state singlet energy levels and excited state triplet energy levels of the first and second hosts, respectively.

28. The organic light emitting diode of claim 26, wherein the emitting material layer further comprises a third emitting material layer disposed between the second exciton energy control layer and the second electrode, wherein the third emitting material layer includes a third host and a third dopant.

29. The organic light emitting diode of claim 28, wherein the second exciton energy control layer includes a second organic compound, and wherein each of an excited state singlet energy level and an excited state triplet energy level of the second organic compound is lower than each of excited state singlet energy levels and excited state triplet energy levels of the first to third hosts, respectively.

30. The organic light emitting diode of claim 29, wherein each of excited state singlet energy levels of the first and second organic compounds is higher than each of excited state singlet energy levels of the second and third dopants, respectively.

31. The organic light emitting diode of claim 28, wherein an excited state singlet energy level of the first dopant is higher than excited state singlet energy levels of the second and third dopants.

32. The organic light emitting diode of claim 10, wherein the second emitting material layer is disposed between the first exciton energy control layer and the second electrode, and the emitting material layer further comprises a second exciton energy control layer disposed between the first electrode and the first emitting material layer, a third emitting material layer disposed between the first electrode and the second exciton energy control layer and including a third host and a third dopant, and a third exciton energy control layer disposed between the second emitting material layer and the second electrode.

33. The organic light emitting diode of claim 1, wherein the at least one emitting unit comprises a first emitting unit disposed between the first and second electrodes, wherein the first emitting unit comprises a lower emitting material layer; and a second emitting unit disposed between the first emitting unit and the second electrode, wherein the second emitting unit comprises an upper emitting material layer, and wherein at least one of the lower emitting material layer and the upper emitting material layer includes the first emitting material layer and the first exciton energy control layer, and further comprises a charge generation layer disposed between the first and second emitting units.

34. An organic light emitting device, comprising:
a substrate; and
the organic light emitting diode according to claim 1 over the substrate.

35. The organic light emitting device of claim 34, wherein the organic light emitting device is an organic light emitting display device or an organic light emitting illumination device.

36. The organic light emitting diode of claim 1, wherein the delayed fluorescent material is selected from:

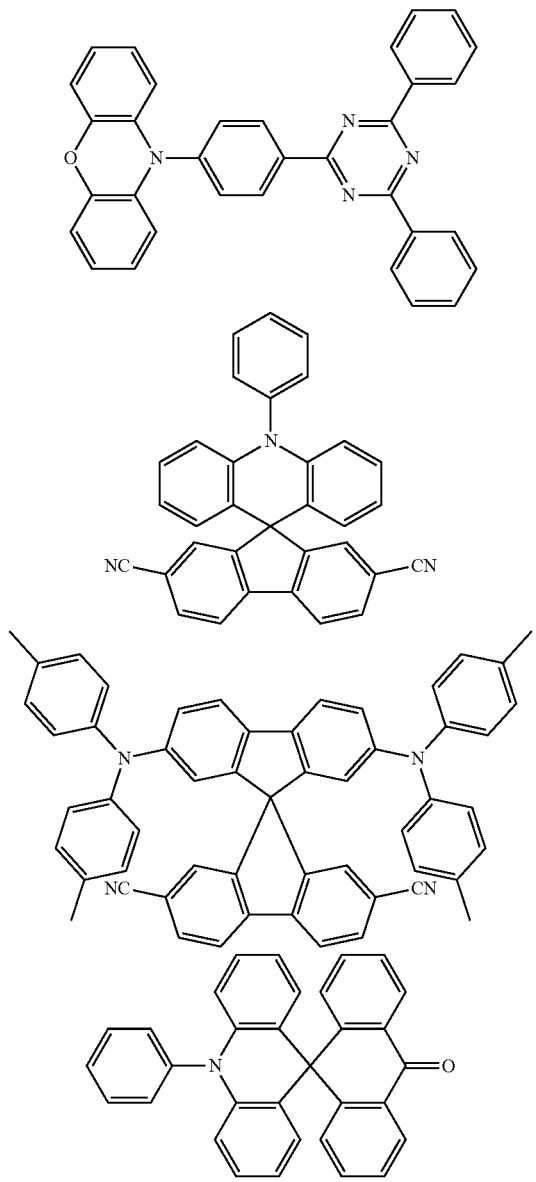

-continued
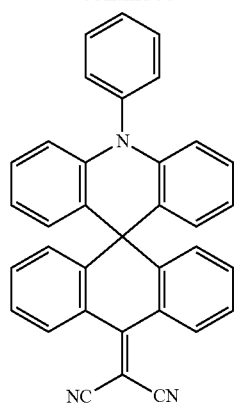
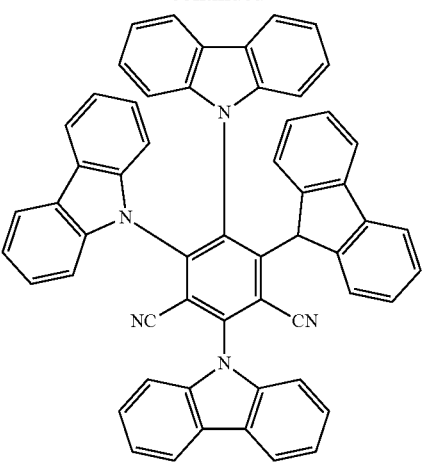
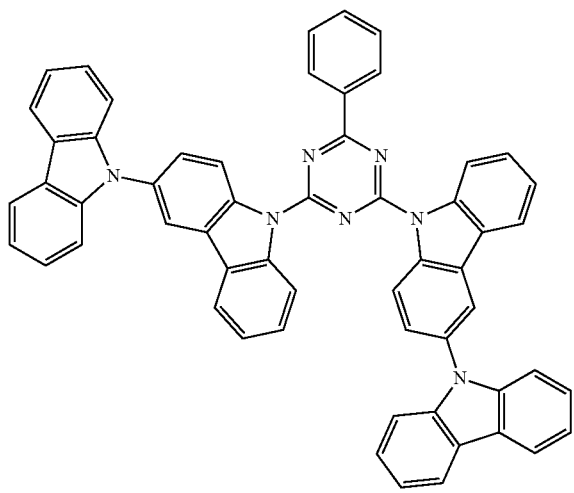
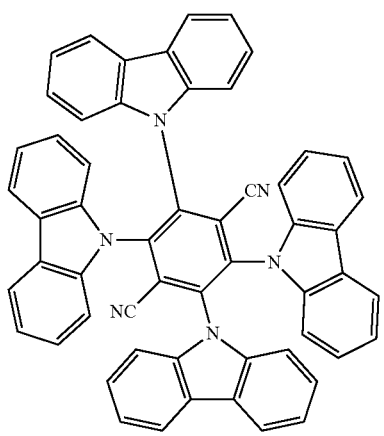
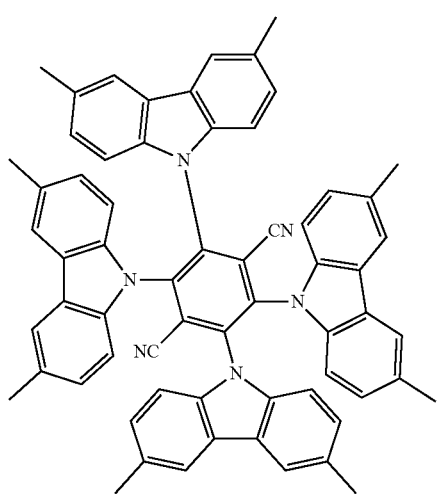
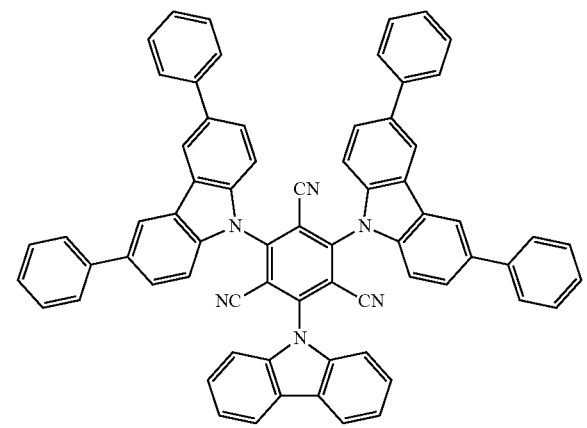

89
-continued
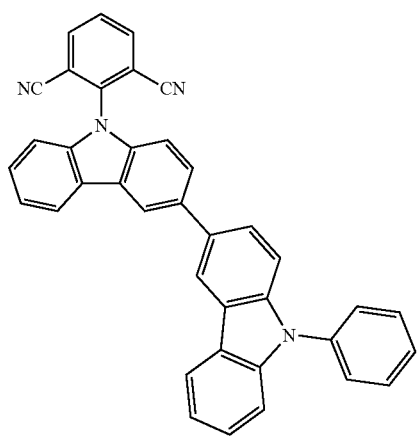
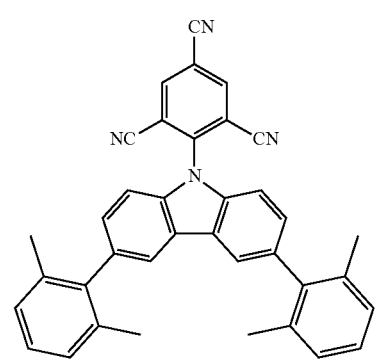
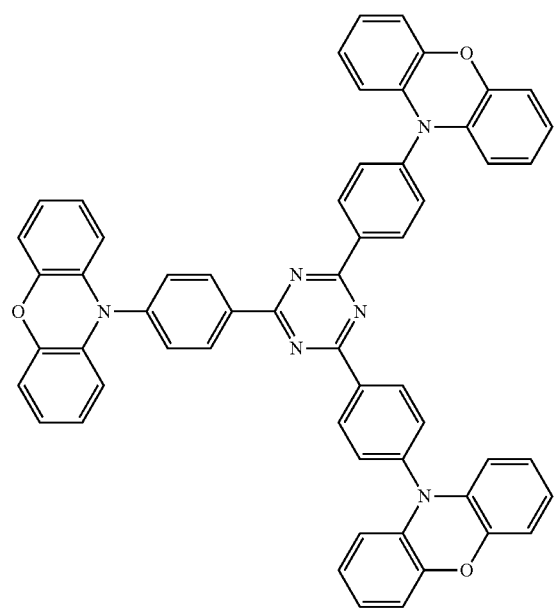
90
-continued
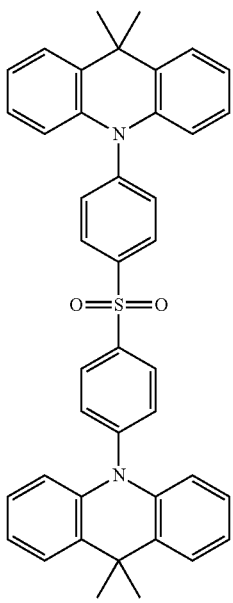
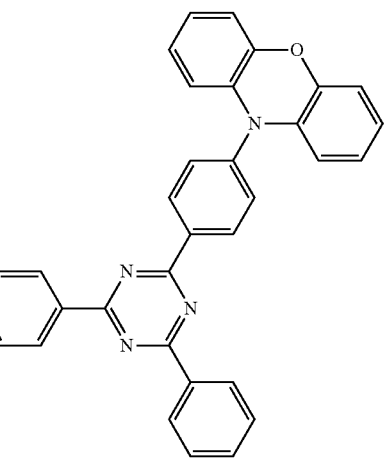
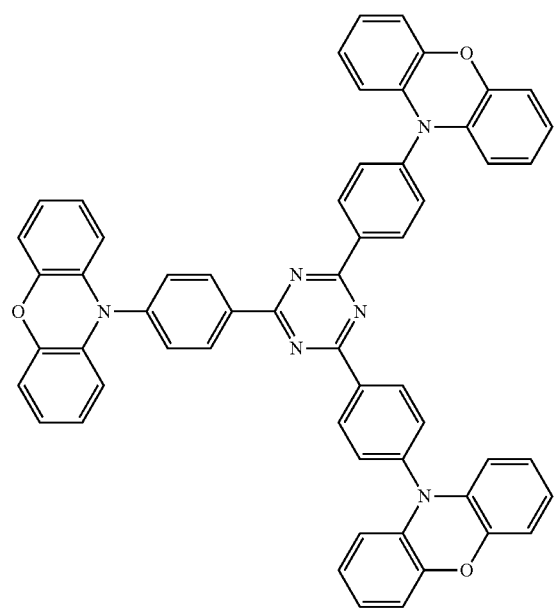

91
-continued
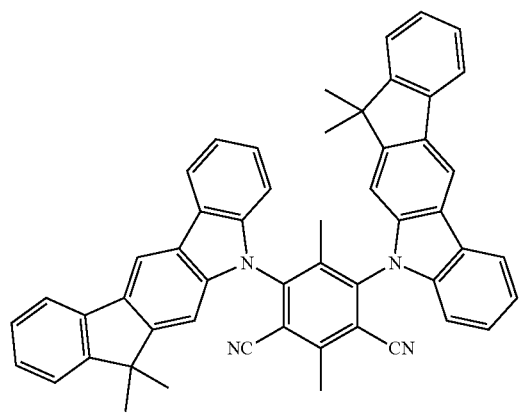
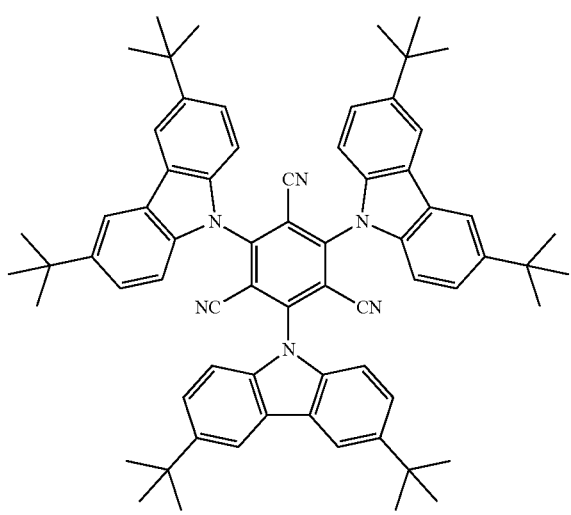
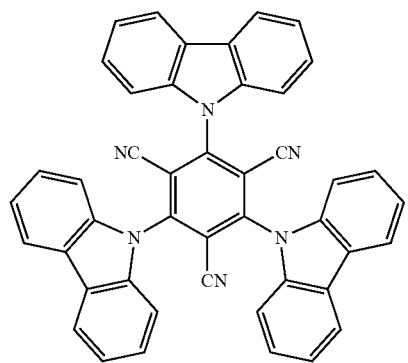
92
-continued
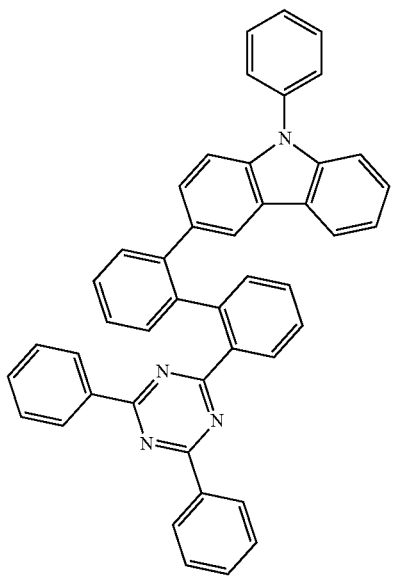
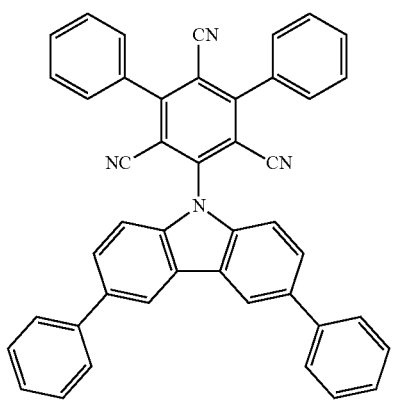
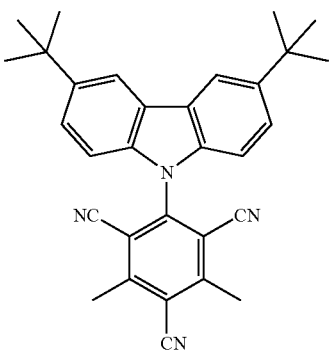

93
-continued
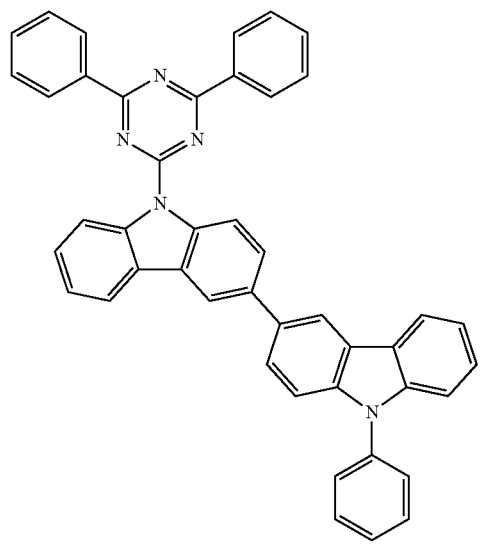
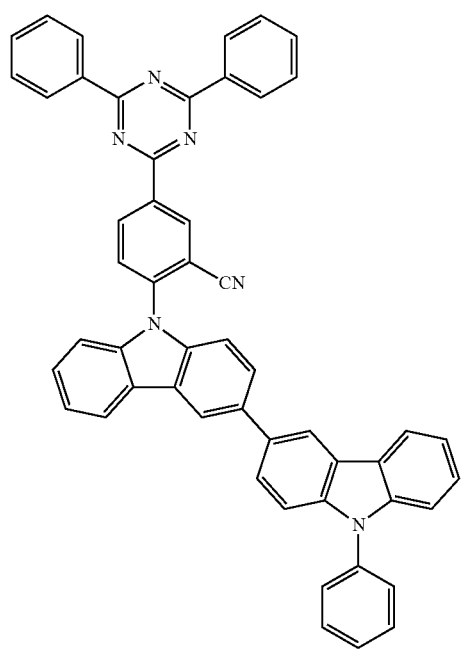
94
-continued
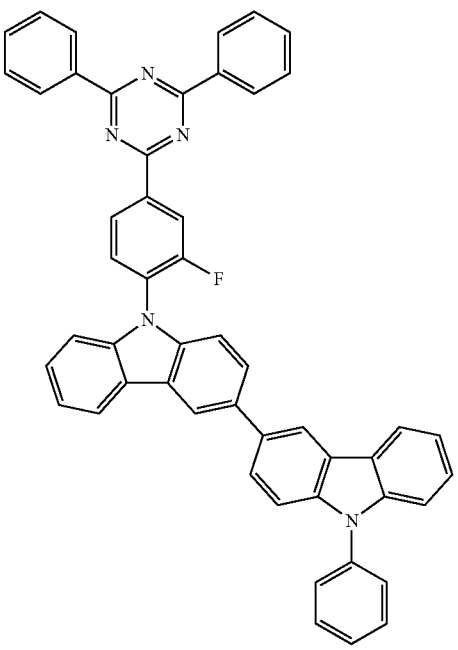
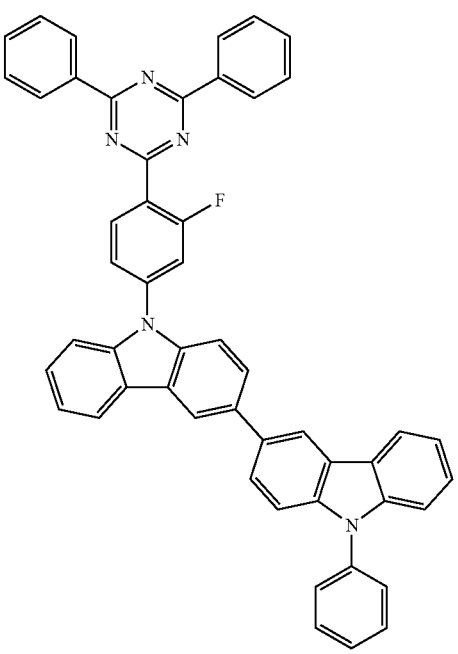

95
-continued
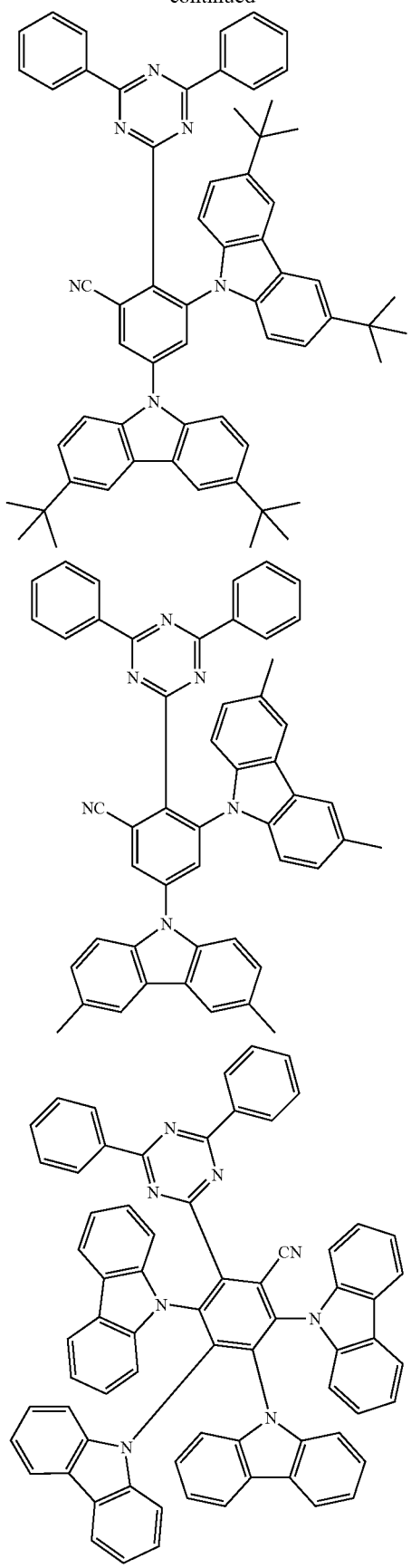
96
-continued
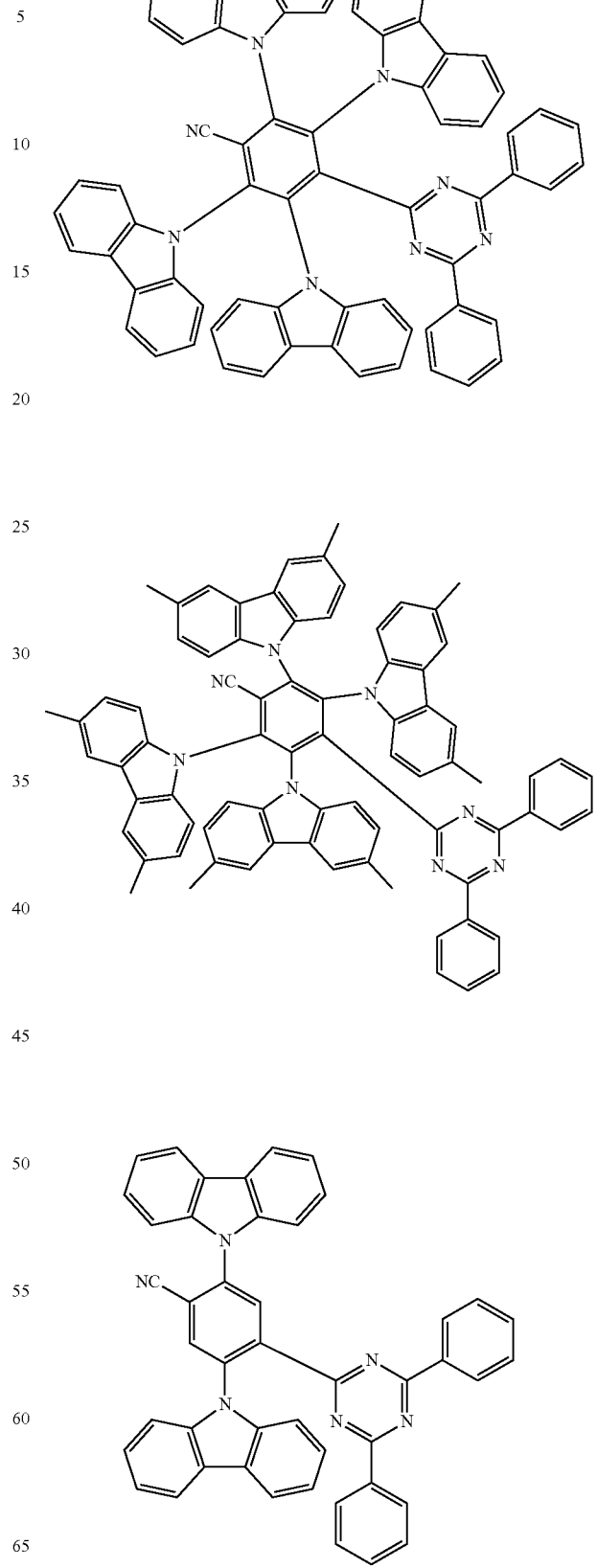

97
-continued
98
-continued
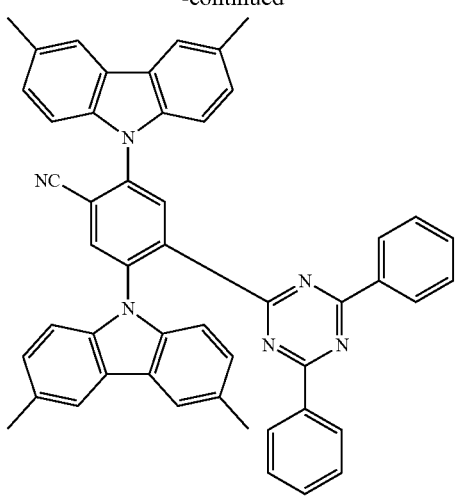
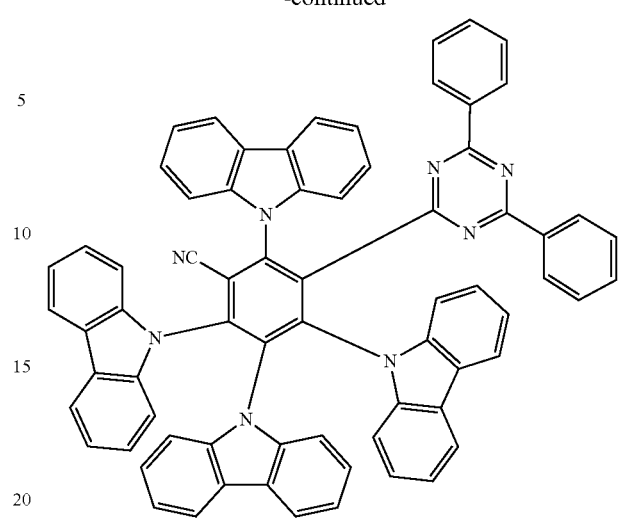
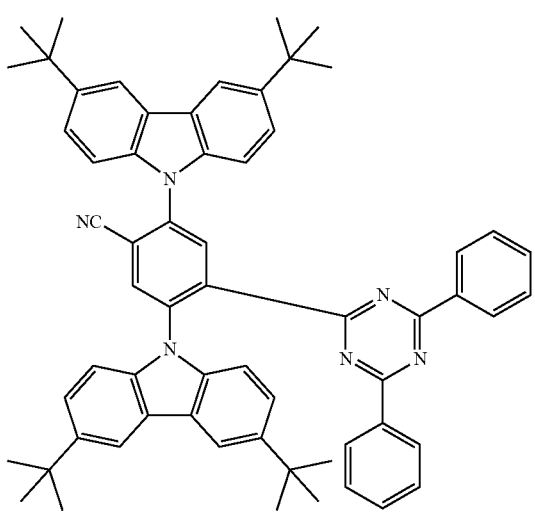
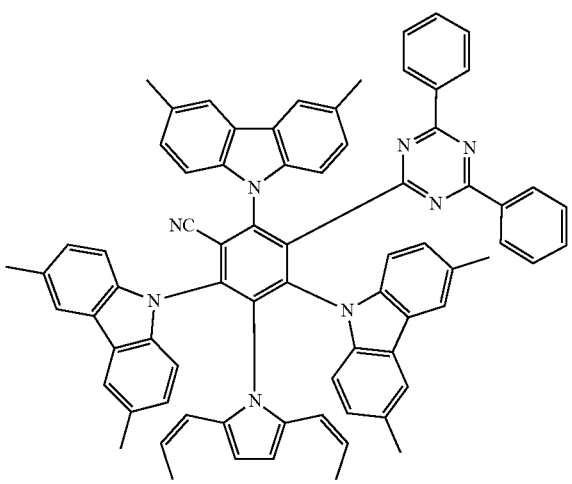
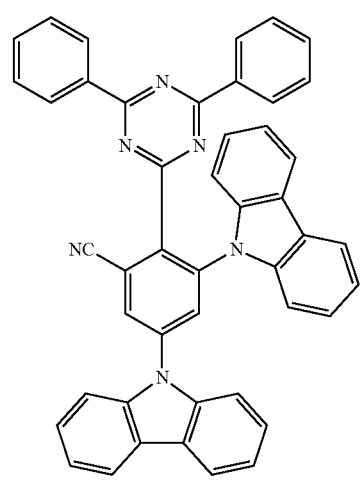
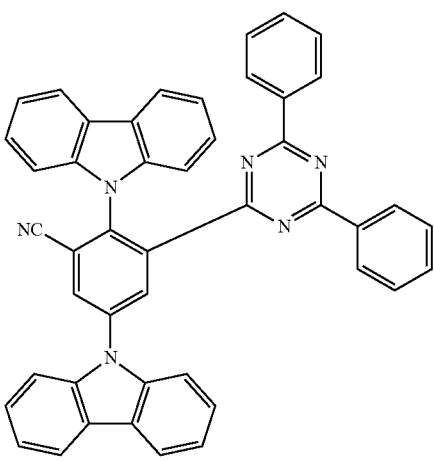

99
-continued
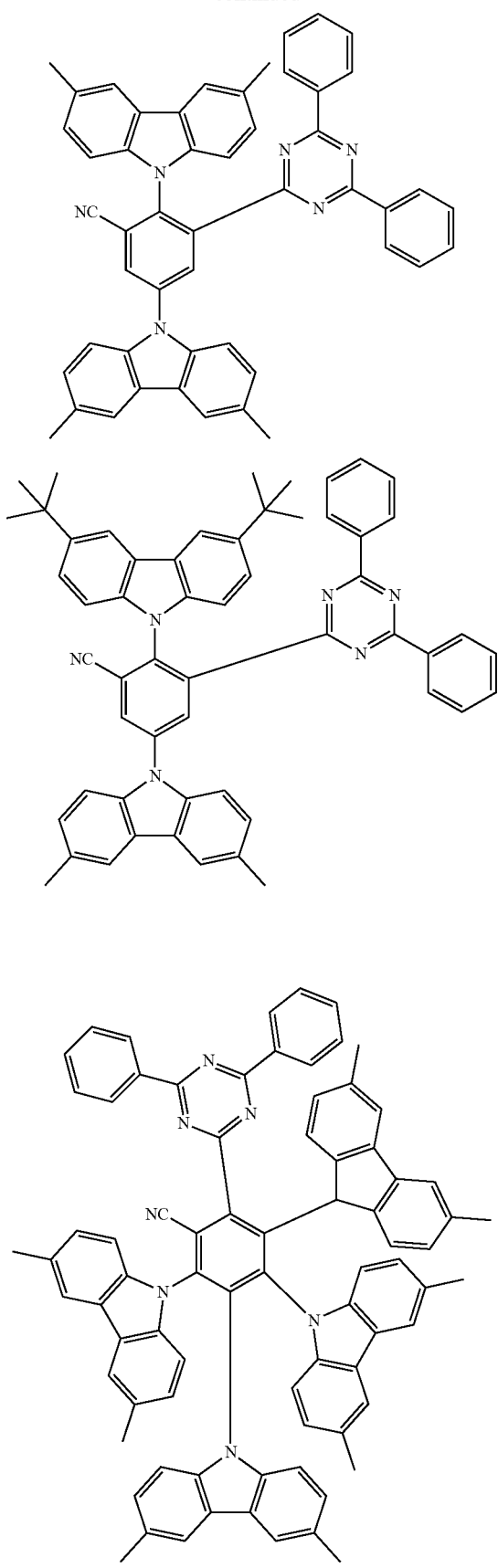
100
-continued
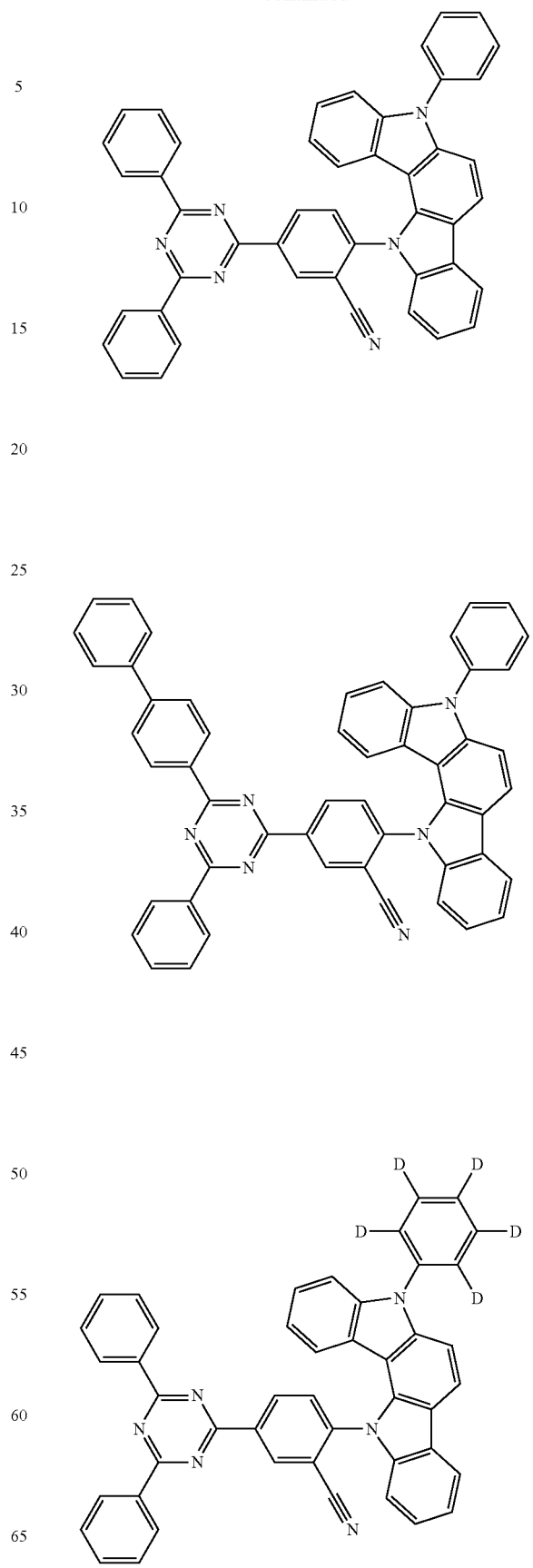

101
-continued
102
-continued
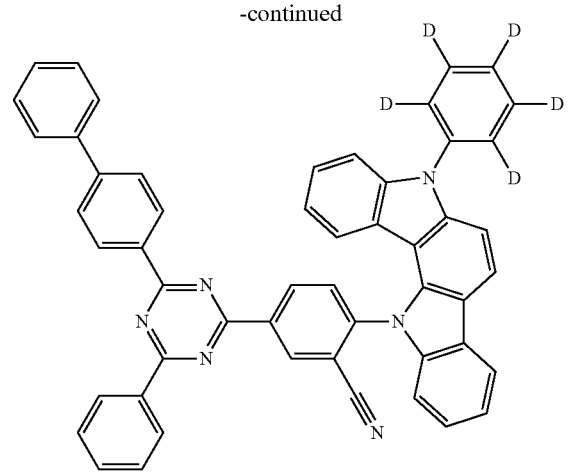
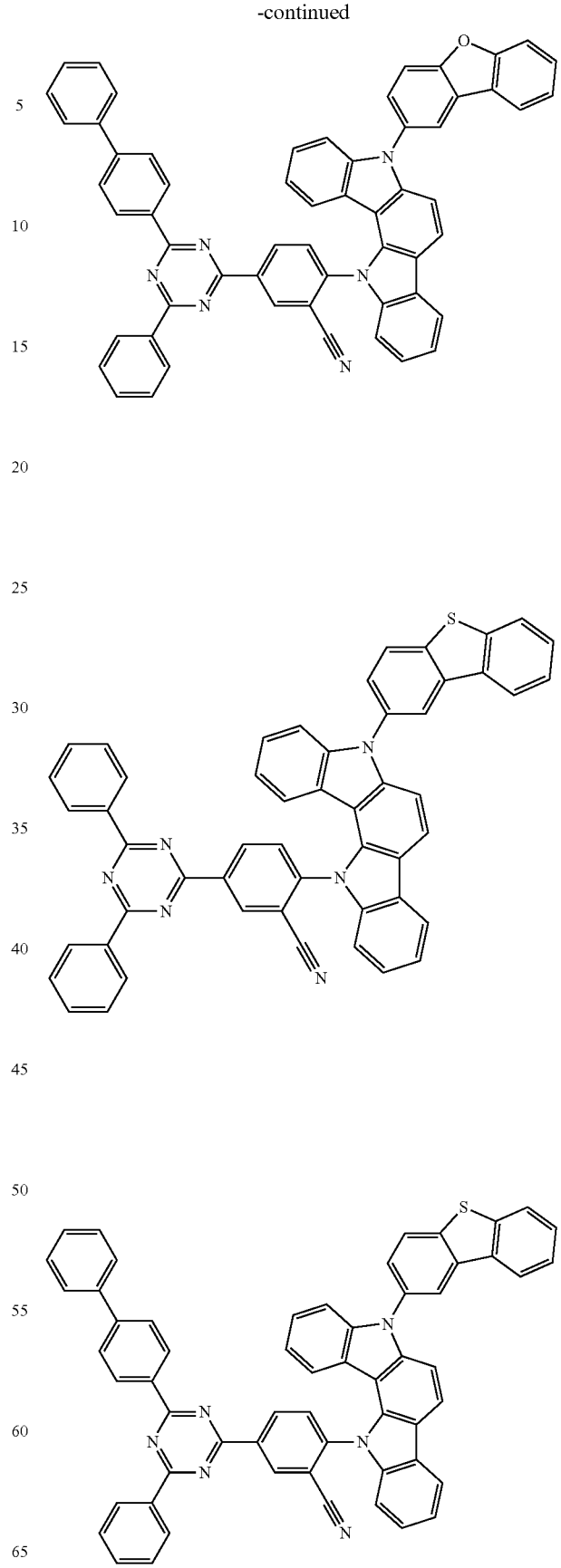

-continued

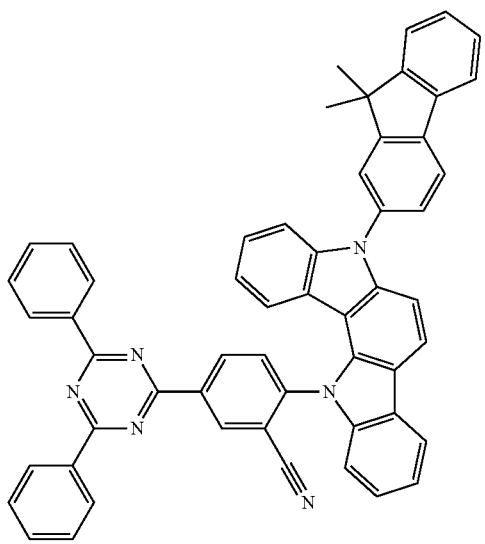

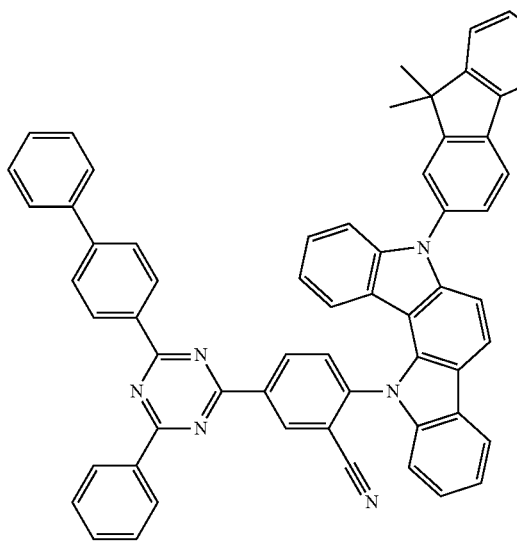

37. The organic light emitting diode of claim 1, wherein the first dopant is selected from the group consisting of 10-(4-(4,6-diphenyl-1,3,5-triazin-2-yl)phenyl)-9,9-dimethyl-9,10-dihydroacridine (DMAC-TRZ), 10,10'-(4,4'-sulfonylbis(4,1-phenylene))bis(9,9-dimethyl-9,10-dihydroacridine) (DMAC-DPS), 10-phenyl-10H,10'H-spiro[acridine-9,9'-anthracen]-10'-one (ACRSA), 3,6-dibenzoyl-4,5-di(1-methyl-9-phenyl-9H-carbazoyl)-2-ethynylbenzonitrile (Cz-VPN), 9,9',9''-(5-(4,6-diphenyl-1,3,5-triazin-2-yl)benzene-1,2,3-triyl) tris(9H-carbazole) (TcZTrz), 9,9'-(5-(4,6-diphenyl-1,3,5-triazin-2-yl)-1,3-phenylene)bis(9H-carbazole) (DczTrz), 9,9',9''',9''''-((6-phenyl-1,3,5-triazin-2,4-diyl)bis(benzene-5,3,1-triyl))tetrakis(9H-carbazole) (DDczTrz), bis(4-(9H-3,9'-bicarbazol-9-yl)phenyl)methanone (CC2BP), 9'-[4-(4,6-diphenyl-1,3,5-triazin-2-yl)phenyl]-3,3''',6,6''-tetraphenyl-9,3':6',9''-ter-9H-carbazole (BDPCC-TPTA), 9'-[4-(4,6-diphenyl-1,3,5-triazin-2-yl)phenyl]-9,3':6',9''-ter-9H-carbazole (BCC-TPTA), 9,9'-(4,4'-sulfonylbis(4,1-phenylene))bis(3,6-dimethoxy-9H-carbazole) (DMOC-DPS), 9-(4-(4,6-diphenyl-1,3,5-triazin-2-yl)phenyl)-3',6'-diphenyl-9H-3,9'-bicarbazole (DPCC-TPTA), 10-(4,6-diphenyl-1,3,5-triazin-2-yl)-10H-phenoxazine (Phen-TRZ), 9-(4-(4,6-diphenyl-1,3,5-triazin-2-yl)phenyl)-9H-carbazole (Cab-Ph-TRZ), 1,2,3,5-Tetrakis(3,6-carbazol-9-yl)-4,6-dicyanobenzene (4CzIPN), 2,3,4,6-tetra(9H-carbazol-9-yl)-5-fluorobenzonitrile (4CZFCN), 10-(4-(4,6-diphenyl-1,3,5-triazin-2-yl)phenyl)-10H-spiro[acridine-9,9'-xanthene], 10-(4-(4,6-diphenyl-1,3,5-triazin-2-yl)phenyl)-10H-spiro[acridine-9,9'-fluorene] (SpiroAC-TRZ) and combination thereof.

38. An organic light emitting diode, comprising:
a first electrode;
a second electrode, wherein the first electrode and the second electrode face each other; and
at least one emitting unit,
wherein the at least one emitting unit is disposed between the first and second electrodes, and comprises an emitting material layer,
wherein the emitting material layer comprises a first emitting material layer including a first host and a first dopant, and a first exciton energy control layer,
wherein the first exciton energy control layer is disposed between the first electrode and the first emitting material layer or disposed between the first emitting material layer and the second electrode,
wherein the first exciton energy control layer comprises a first organic compound, wherein each of an excited state singlet energy level and an excited state triplet energy level of the first organic compound is lower than each of an excited state singlet energy level and an excited state triplet energy level of the first host, respectively, and
wherein the first dopant comprises the first organic compound.

39. An organic light emitting diode, comprising:
a first electrode;
a second electrode, wherein the first electrode and the second electrode face each other; and
at least one emitting unit,
wherein the at least one emitting unit is disposed between the first and second electrodes, and comprises an emitting material layer,
wherein the emitting material layer comprises a first emitting material layer including a first host and a first dopant, and a first exciton energy control layer,
wherein the first exciton energy control layer is disposed between the first electrode and the first emitting material layer or disposed between the first emitting material layer and the second electrode,
wherein the first exciton energy control layer comprises a first organic compound, wherein each of an excited state singlet energy level and an excited state triplet energy level of the first organic compound is lower than each of an excited state singlet energy level and an excited state triplet energy level of the first host, respectively, and wherein the first organic compound has the following structure of Chemical Formula 1:

Chemical Formula 1

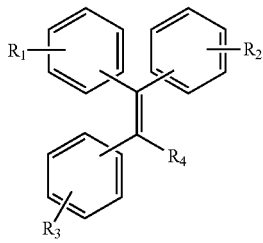

wherein each of $R_1$ to $R_3$ is independently protium, deuterium, tritium, $C_5$~$C_{30}$ aryl group unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group, or $C_4$~$C_{30}$ hetero aryl group unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group; and wherein $R_4$ is protium, deuterium, tritium or phenyl group unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group.

40. The organic light emitting diode of claim 39, wherein the first organic compound includes an organic compound having the following structure of Chemical Formula 2:

Chemical Formula 2

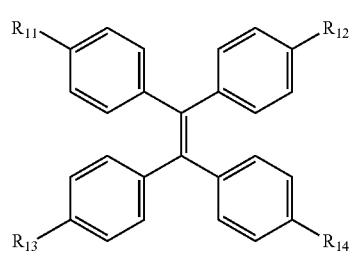

wherein each of $R_{11}$ to $R_{14}$ is independently protium, deuterium, tritium or aryl or hetero aryl group selected from the group consisting of phenyl, pyridyl, carbazolyl, acridinyl, phenazinyl, phenoxazinyl, dibenzofuranyl, dibenzothiophenyl, diazinyl and triazinyl, each of which is unsubstituted or substituted with cyano group, nitro group, halogen, $C_1$~$C_{10}$ alkyl group, $C_1$~$C_{10}$ alkyl halide group, $C_5$~$C_{30}$ aryl group or $C_4$~$C_{30}$ hetero aryl group, wherein at least two of $R_1$ to $R_{14}$ is the aryl or hetero aryl group, wherein at least one of Rn to $R_{14}$ is pyridyl, diazinyl or triazinyl and other of $R_1$ to $R_{14}$ is phenyl, carbazolyl, acridinyl, phenazinyl, phenoxazinyl, dibenzofuranyl or dibenzothiophenyl.

* * * * *